United States Patent
Banerjee et al.

(10) Patent No.: US 7,361,643 B2
(45) Date of Patent: Apr. 22, 2008

(54) METHODS FOR INHIBITING ANGIOGENESIS

(75) Inventors: Dipak K. Banerjee, Guaynabo, PR (US); Juan A. Martinez, Rio Piedras, PR (US)

(73) Assignee: University of Puerto Rico, San Juan, PR (US)

( * ) Notice: Subject to any disclaimer, the term of this patent is extended or adjusted under 35 U.S.C. 154(b) by 1143 days.

(21) Appl. No.: 09/779,447

(22) Filed: Feb. 9, 2001

(65) Prior Publication Data

US 2002/0160979 A1    Oct. 31, 2002

Related U.S. Application Data

(60) Provisional application No. 60/181,312, filed on Feb. 9, 2000.

(51) Int. Cl.
*A61K 31/7068* (2006.01)
(52) U.S. Cl. ..................................................... 514/50
(58) Field of Classification Search ................. 514/23, 514/25, 49, 62, 50
See application file for complete search history.

(56) References Cited

U.S. PATENT DOCUMENTS

| | | | |
|---|---|---|---|
| 5,382,514 A | 1/1995 | Passaniti et al. | |
| 5,629,340 A | 5/1997 | Kuwano et al. | |
| 5,760,028 A | 6/1998 | Jadhav et al. | |
| 5,760,029 A | 6/1998 | Jadhav et al. | |
| 5,766,591 A | 6/1998 | Brooks et al. | |
| 5,807,731 A | 9/1998 | Van Meir et al. | |
| 5,830,880 A | 11/1998 | Sedlacek et al. | |
| 5,837,682 A | 11/1998 | Folkman et al. | |
| 5,854,205 A | 12/1998 | O'Reilly et al. | |
| 5,932,611 A | 8/1999 | Wuthier et al. | |
| 5,945,403 A | 8/1999 | Folkman et al. | |
| 5,981,471 A | 11/1999 | Papathanassiu et al. | |
| 5,985,839 A | 11/1999 | Dupont et al. | |
| 5,994,309 A | 11/1999 | Mazar et al. | |
| 6,024,688 A | 2/2000 | Folkman et al. | |
| 6,051,230 A | 4/2000 | Thorpe et al. | |
| 6,096,730 A | 8/2000 | Collins et al. | |
| 6,114,355 A | 9/2000 | D'Amato | |
| 6,121,236 A | 9/2000 | Ben-Sasson | |
| 6,130,231 A | 10/2000 | Wityak et al. | |
| 6,146,824 A | 11/2000 | Bar-Shavit | |
| 6,150,407 A | 11/2000 | Tusé et al. | |
| 6,153,603 A | 11/2000 | Sirén | |
| 6,160,166 A | 12/2000 | Collins et al. | |

OTHER PUBLICATIONS

Presta et al., Cancer Research vol. 59, pp. 2417-2424.*
Banerjee et al., Indian J. of Biochem. and Biophysics, vol. 30(6), pp. 389-394, see abstract.*
Banerjee et al., Indian J. Biochem. and Biophysics, vol. 30(6), pp. 389-394, (1993).*
Exp. Cell Research, vol. 198, pp. 191-200 (1992), submitted in IDS filed Jul. 16, 2001.*
Cockerill et al., "Angiogenesis: Model and Modulators", *Int Rev Cytol*, 159: 113-160 (1995).
Folkman et al., "Angiogenesis", *J Biol Chem*, 267:10931-10934 (1992).
Beck et al., "Vascular Development: Cellular and Molecular Regulation", *FASEB J.*, 11:365-373 (1997).
Bussolino et al., "Molecular Mechanisms of Blood Vessel Formation", *TIBS*, 22:251-256 (1997).
Folkman et al., "Induction of Angiogenesis During the Transition from Hyperplasia to Neoplasia", *Nature*, 339: 58-61 (1989).
Friedlander et al., "Definition of Two Angiogenic Pathways by Distinct $\alpha_v$ Integrins", *Science*, 270:1500-1502 (1995).
Liotta et al., "Cancer Metastasis and Angiogenesis: an Imbalance of Positive and Negative Regulation", *Cell*, 64:327-336 (1991).
Saclarides et al., "Tumor Angiogenesis and Rectal Carcinoma", *Dis. Colon Rectum*, 37:921-926 (1994).
Shweiki et al., "Patterns of Expression of Vascular Endothelial Factor (VEGF) and VEGF Receptors in Mice Suggest a Role in Hormonally Regulated Angiogenesis", *J. Clin. Invest.*, 91:2235-2243 (1993).
Vartanian et al., "Correlation of Intratumoral Endothelial Cell Proliferation with Microvessel Density (Tumor Angiogenesis) and Tumor Cell Proliferation in Breast Carcinoma", *Am. J. Pathol.*, 144:1188-1194 (1994).
Folkman et al., "Angiogenic Factors", *Science*, 235:442-447 (1987).
Furcht, "Critical Factors Controlling Angiogenesis: Cell Products, Cell Matrix, and Growth Factors", *Lab. Invest.*, 55:505-509 (1986).
Denekamp, "Angiogenesis, Neovascular Proliferation and Vascular Pathophysiology as Targets for Cancer Therapy", *Br. J. Radiol.*, 66:181-196 (1993).
Nicolson, "Cancer Metastasis", *Sci. Am.*, 240:66-76 (1979).
Nagy et al., "Pathogenesis of Tumor Stroma Generation: a Critical Role for Leaky Blood Vessels and Fibrin Deposition", *Biochim Biophys. Acta*, 948:305-326 (1989).
Moscatelli et al., "Angiogenic Factors Stimulate Plasminogen Activator and Collagenase Production by Capillary Endothelial Cells", *J. Cell Biol.*, 91:201a (1981).

(Continued)

*Primary Examiner*—Shaojia Anna Jiang
*Assistant Examiner*—Ganapathy Krishnan
(74) *Attorney, Agent, or Firm*—Roberto J. Rios; Hoglund & Pamias, PSC

(57) ABSTRACT

A method for inhibiting angiogenesis, including: administering a nucleoside, such as tunicamycin, in an amount effective to inhibit angiogenesis, to a patient in need of such treatment. A method for inhibiting angiogenesis, including: administering a nucleoside, which comprises glucosamine, in an amount effective to inhibit angiogenesis, to a patient in need of such treatment; wherein the nucleoside is administered for a period of time, subsequently the administration of the nucleoside is suspended for a period of time of at least about 1 week, and subsequently the administration of the nucleoside is resumed.

3 Claims, 19 Drawing Sheets

OTHER PUBLICATIONS

Liotta et al., "The Significance of Hematogenous Tumor Cell Clumps in the Metastatic Process", *Cancer Res.*, 36:889-894 (1976).

Folkman, "Tumor Angiogenesis: Therapeutic Implications", *N. Engl. J. Med.*, 285:1182-1186 (1971).

Folkman, "Clinical Applications of Research on Angiogenesis", *N. Engl. J. Med.*, 333:1757-1763 (1995).

Harris et al., "Gene Therapy Through Signal Transduction Pathways and Angiogenic Growth Factors as Therapeutic Targets in Breast Cancer", *Cancer*, 74:1021-1025 (1994).

Ingber et al., "Synthetic Analogues of Fumagillin that Inhibit Angiogenesis and Suppress Tumor Growth", *Nature*, 348:555-557 (1990).

Hori et al., "Suppression of Solid Tumor Growth by Immunoneutralizing Monoclonal Antibody Against Human Basic Fibroblast Growth Factor", *Cancer Res.*, 51:6180-6184 (1991).

Kim et al., "Inhibition of Vascular Endothelial Growth Factor-induced Angiogenesis Suppresses Tumor Growth in vivo", *Nature*, 362:841-844 (1993).

Millauer et al., "Glioblastoma Growth Inhibited in vivo by a Dominant-negative Flk-1 Mutant", *Nature*, 367:576-579 (1994).

Brooks et al., "Integrin $\alpha v \beta 3$ Antagonists Promote Tumor Regression by Inducing Apoptosis of Angiogenic Blood Vessels", *Cell*, 79:1157-1164 (1994).

Rak et al., "Progressive Loss of Sensitivity to Endothelium-derived Growth Inhibitors Expressed by Human Melanoma Cells during Disease Progression", *J. Cell Physiol.*, 159:245-255 (1994).

Hamada et al., "Separable Growth and Migration Factors for Large-cell Lymphoma Cells Secreted by Microvascular Endothelial Cells Derived from Target Organs for Metastasis", *Br. J. Cancer*, 66:349-354 (1992).

Fox et al., "High Levels of uPA and pA-1 are Associated with Highly Angiogenic Breast Carcinomas", *J. Pathol.*, 170:388a (1993).

Polverini et al., "Induction of Neovascularization in vivo and Endothelial Proliferation in vitro by Tumor Associated Macrophages", *Lab. Invest.*, 51:635-642 (1984).

Frater-Schroder et al., "Tumor Necrosis Factor Type $\alpha$, a Potent Inhibitor of Endothelial Cell Growth in vitro, is Angiogenic in vivo", *Proc. Natl. Acad. Sci* (USA), 84:5277-5281 (1987).

Schreiber et al., "Transforming Growth Factor-$\alpha$: a More Potent Angiogenic Mediator than Epidermal Growth Factor", *Science*, 232:1250-1253 (1986).

Hockel et al., "Purified Monocyte-derived Angiogenic Substance (Angiotropin) Induces Controlled Angiogenesis Associated with Regulated Tissue Proliferation in Rabbit Skin", *J. Clin. Invest.*, 82:1075-1090 (1988).

Thornton et al., Human Endothelial Cells: Use of Heparin in Cloning and Long-term Serial Cultivation, *Science*, 222:623-625 (1983).

Dethlefsen et al., "Tumor Growth and Angiogenesis in Wild Type and Mast Cell Deficient Mice", *FASEB J.*, 4:A623 (1990).

Kandel et al., "Neovascularization is Associated with a Switch to the Export of bFGF in the Multistep Development of Fibrosarcoma", *Cell*, 66:1095-1104 (1991).

Nguyen et al., "Elevated Levels of the Angiogenic Peptide Basic Fibroblast Growth Factor in Urine of Bladder Cancer Patients", *J. Natl. Cancer Inst.*, 85:241-242 (1993).

Brown et al., "Increased Expression of Vascular Permeability Factor (Vascular Endothelial Growth Factor) and its Receptors in Kidney and Bladder Carcinomas", *Am J. Pathol.*, 143:1255-1262 (1993).

Goto et al., "Synergistic Effects of Vascular Endothelial Growth Factor and Basic Fibroblast Growth Factor on the Proliferation and Cord Formation of Bovine Capillary Endothelial Cells within Collagen Gels", *Lab. Invest.*, 69:508-517 (1993).

Leibovich et al., "Production of Angiogenic Activity by Human Monocytes Requires an L-arginine/nitric oxide-synthase-dependent Effector Mechanism", *Proc. Natl. Acad. Sci* (USA), 91:4190-4194 (1994).

Banerjee, "Microenvironment of Endothelial Cell Growth and Regulation of Protein N-glycosylation", *Indian J. Biochem. Biophys.*, 25:8-13 (1988).

Banerjee et al., "Biphasic Estrogen Response on Bovine Adrenal Medulla Capillary Endothelial Cell Adhesion, Proliferation and Tube Formation", *Mol. Cell Biochem.*, 177:97-105 (1997).

Bond et al., "Replacement of Residues of 8-22 of Angiogenin with 7-21 of RNase A Selectively Affects Protein Synthesis Inhibition and Angiogenesis", *Biochemistry*, 29:3341-3349 (1990).

Bouck et al., "Coordinate Control of Anchorage Independence, Actin Cytoskeleton and Angiogenesis by Human Chromosome 1 in Hamster-human Hybrids", *Cancer Res.*, 46:5101-5105 (1986).

Rastinejad et al., "Regulation of the Activity of a New Inhibitor of Angiogenesis by a Cancer Suppressor Gene", *Cell*, 56:345-355 (1989).

Zajchowski et al., "Suppression of Tumor-forming Ability and Related Traits in MCF—7 Human Breast Cancer Cells by Fusion with Immortal Mammary Epithelial Cells", *Proc. Natl. Acad. Sci* (USA), 87:2314-2318 (1990).

O'Reilly et al., "Angiostatin: A Novel Angiogenesis Inhibitor that Mediates the Suppression of Metastases by a Lewis Lung Carcinoma", *Cell*, 79:315-328 (1994).

Bergers et al., "Effects of Angiogenesis Inhibitors on Multistage Carcinogenesis in Mice", *Science*, 284:808-812 (1999).

Brooks et al., "Requirement of Vascular Integrin $\alpha_v \beta_3$ for Angiogenesis", *Science*, 264:569-571 (1994).

Hanahan et al., "Patterns and Emerging Mechanisms of the Angiogenic Switch During Tumorigenesis", *Cell*, 86:353-364 (1996).

Nguyen et al., "1-Deoxymannojirimycin Inhibits Capillary Tube Formation in vitro, Analysis of N-linked Oligosaccharides in Bovine Capillary Endothelial Cells", *J. Biol. Chem.*, 267:26157-26165 (1992).

Pili et al., "The $\alpha$-glucosidase I Inhibitor Castanospermine Alters Endothelial Cell Glycosylation, Prevents Angiogenesis, and Inhibits Tumor Growth", *Cancer Res.*, 55:2920-2926 (1995).

Banerjee et al., "Is Asparagine-Linked Protein Glycosylation an Obligatory Requirement for Angiogenesis?", *Indian J. Biochem. Biophys.*, 30:389-394 (1993).

Elbein, "Inhibitors of the Biosynthesis and Processing of N-linked Oligosaccharide Chains", *Ann. Rev. Biochem.*, 56:497-534 (1987).

Tiganis et al., "Functional and Morphological Changes Induced by Tunicamycin in Dividing and Confluent Endothelial Cells", *Exp. Cell Res.*, 198:191-200 (1992).

Chapman et al., "Structure of the Lipid-linked Oligosaccharides that Accumulate in Class E *thy-1*-negative Mutant Lymphomas", *Cell*, 17:509-515 (1979).

Banerjee et al., "Amphomycin: Effect of the Lipopeptide Antibiotic on the Glycosylation and Extraction of Dolichyl Monophosphate in Calf Brain Membranes", *Biochemistry*, 20:1561-1568 (1981).

Banerjee, "Amphomycin Inhibits Mannosylphosphoryldolichol Synthesis by Forming a Complex with Dolichylmonophosphate", *J. Biol. Chem.*, 264:2024-2028 (1989).

Banerjee, "A Recent Approach to the Study of Dolichyl Monophosphate Topology in the Rough Endoplasmic Reticulum", *Acta Biochimica Polonica*, 41:275-280 (1994).

Banerjee et al., "Endothelial Cells from Bovine Adrenal Medulla Develop Capillary-like Growth Patterns in Culture", *Proc. Natl. Acad. Sci. USA*, 82:4702-4706 (1985).

Banerjee et al., "Microvascular Endothelial Cells from Bovine Adrenal Medulla—A Model for in vitro Angiogenesis", *Angiogenesis: Models, Modulators and Clinical Applications*, pp. 7-18 (1998).

Kornfeld et al., "Assembly of Asparagine-Linked Oligosaccharides", *Annu Rev Biochem*, 54:631-664 (1985).

Heinemann et al., "Amphomycin, a New Antibiotic", *Antibiot. Chemother.*, 3:1239-1242 (1953).

Bodanszky et al., "Structure of the Peptide Antibiotic Amphomycin", *J. Am. Chem. Soc.*, 95:2352-2357 (1973).

Banerjee, "Amphomycin: A Tool to Study Protein N-glycosylation", *J. Biosci.*, 11:311-319 (1987).

Banerjee et al., "Monoclonal Antibody to Amphomycin. A Tool to Study the Topography of Dolichol Monophosphate in the Membrane", *Carbohyd. Res.*, 236:301-313 (1992).

Banerjee et al., "cAMP-Mediated Protein Phosphorylation of Microsomal Membranes Increases Mannosylphosphodolichol Synthase Activity", *Proc Natl Acad Sci* (USA), 84:6389-6393 (1987).

Elias et al., "Direct Arterial Vascularization of Estrogen-Induced Prolactin-Secreting Anterior Pituitary Tumors", *Proc Natl Acad Sci* (USA), 81:4549-4553 (1984).

Das et al., "β-adrenoreceptors of Multiple Affinities in a Clonal Capillary Endothelial Cell Line and its Functional Implication", *Mol. Cell. Biochem.*, 140:49-54 (1994).

Banerjee et al., "Protein Kinase Type I Regulates GDP-mannose:dolichylphosphate-O-β-D-mannosyltransferase in the ER", *FASEB J*, 9:1361a (1995).

Colussi et al., "Human and *Saccharomyces cerevisiae* Dolichol Phosphate Mannose Synthases Represent Two Class of the Enzyme, but both Function in *Schizosaccharomyces pombe*", *Proc Natl Acad Sci* (USA), 94: 7873-7878 (1997).

Orlean et al., "Cloning and Sequencing of the Yeast Gene for Dolichol Phosphate Mannose Synthase, an Essential Proteins", *J. Biol. Chem.*, 263:17499-17507 (1988).

Mazhari-Tabrizi et al., "Cloning and Functional Expression of the Glycosyltransferases from Parasitic Protozoans by Heterologous Complementation in Yeast: the Dolichol Phosphate Mannose Synthase from *Trypanosoma brucei brucei*", *Biochem. J.*, 316:853-858 (1996).

Banerjee, "Regulation of Mannosylphosphoryldolichol Synthase Activity by cAMP-dependent Protein Phosphorylation", *Highlights of Modern Biochemistry*, pp. 379-388 (1989).

Banerjee et al., "In vitro Phosphorylation of Recombinant Dol-P-Man Synthase from *S. cerevisiae* Enhances its Activity", *FASEB J.*, 12:A1363 (1998).

Carrasquillo et al., "Serine 141 is Essential for Dol-P-Man Synthase Activity in *S. cerevisiae*", *Glycobiology*, 8:93a (1997).

Walker et al., "A Functional Link Between N-linked Glycosylation and Apoptosis in Chinese Hamster Ovary Cells", *Biochem. Biophys. Res. Commun.*, 250:264-270 (1998).

Rosenwald et al., "Control of Carbohydrate Processing: Increased β1,6-branching in N-linked Carbohydrates of Lec9 CHO Mutants Appears to Arise from a Defect in Oligosaccharide-dolichol Synthesis", *Mol. Cell. Biol.*, 9:914-924 (1989).

Yue et al., "2-Methoxyestradiol, an Endogenous Estrogen Metabolite, Induces Apoptosis in Endothelial Cells and Inhibits Angiogenesis: Possible Role for Stress Activated Protein Kinase Signaling Pathway and Fas Expression", *Molecular Pharmacology*, vol. 51, pp. 951-962 (1997).

Guo et al., "Thrombospondin 1 and Type I Repeat Peptides of Thrombospondin 1 Specifcally Induce Apoptosis of Endothelial Cells", *Cancer Research*, 57:1735-1743 (1997).

Pahl, "Signal Transduction from the Endoplasmic Reticulum to the Cell Nucleus", *Physiol. Rev.*, 79:683-701 (1999).

Reddy et al., "Assembly, Sorting and Exit of Oligomeric Proteins from the Endoplasmic Reticulum", *BioEssays*, 20:546-554 (1998).

Wang et al., "Signals from the Stressed Endoplasmic Reticulum Induce C/EBP-homologous Protein (CHOP/GADD153)", *Mol. Cell. Biol.*, 16:4273-4280 (1996).

Wang et al., "Cloning of Mammalian Ire1 Reveals Diversity in the ER Stress Responses", *EMBO J.*, 17:5708-5717 (1998).

Harding et al., "Protein Translation and Folding are Coupled by an Endoplasmic-reticulum-resident Kinase", *Nature*, 397:271-274 (1999).

Brewer et al., "Mammalian Unfolded Protein Response Inhibits Cyclin D1 Translation and Cell-cycle Progression", *Proc. Natl. Acad. Sci* (USA), 96:8505-8610 (1999).

Nakagawa et al., "Caspase-12 Mediates Endoplasmic-reticulum-Specific Apoptosis and Cytotoxicity by Amyloid-β", *Nature*, 403:98-103 (2000).

Pouyssegur et al., "Induction of Two Transformation-sensitive Membrane Polypeptides in Normal Fibroblasts by a Block in Glycoprotein Synthesis or Glucose Deprivation", *Cell*, 11:941-947 (1977).

Shiu et al., "Glucose Depletion Accounts for the Induction of Two Transformation-sensitive Membrane Proteins in Rous Sarcoma Virus-transformed Chick Embryo Fibroblasts", *Proc. Natl. Acad. Sci.* (USA) 74:3840-3844 (1977).

Peluso et al., "Infection with Paramyxoviruses Stimulates Synthesis of Cellular Polypeptides that are also Stimulated in Cells Transformed by Rous Sarcoma Virus or Deprived of Glucose", *Proc. Natl. Acad. Sci.* (USA), 75:6120-6124 (1978).

Gething et al., "Protein Folding in the Cell", *Nature*, 355:33-45 (1992).

Pahl et al., "A Novel Signal Transduction Pathway from the Endoplasmic Reticulum to the Nucleas is Mediated ; by Transcription Factor NF-kappa B", *EMBO J.*, 14:2580-2588 (1995).

Watowich et al., "Complex Regulation of Heat Shock- and Glucose-responsive Genes in Human Cells", *Mol Cell Biol.*, 8:393-405 (1988).

Duksin et al., "Relationship of the Structure and Biological Activity of the Natural Homologues of Tunicamycin", *J. Biol. Chem.*, 257:3105-3109 (1982).

Maheshwari et al., "Interferon Treatment Inhibits Glycosylation of a Viral Protein", *Nature*, 287:454-456 (1980).

Martínez et al., "Tunicamycin Inhibits Capillary Endothelial Cell Proliferation by Inducing Apoptosis", *Angiogenesis: From the Molecular to Integrative Pharmacology*, abstract (2000).

Martínez et al., "N-glycosylation Inhibition on Endothelial Cell Proliferation and Viability", *FASEB J.*, 12:231a (1998).

Youdim et al., "Isolated Chromaffin Cells from Adrenal Medulla Contain Primarily Monoamine Oxidase B", *Science*, 224:619-621 (1984).

Youdim et al., "Steroid Regulation of Monoamine Oxidase Activity in the Adrenal Medulla", *FASEB J.*, 3:1753-1759 (1989).

Banerjee et al., "Expression of Blood Clotting Factor VIII:C Gene in Capillary Endothelial Cells", *FEBS Letts.*, 306:33-37 (1992).

Martínez et al., "Expression of $GLc_3Man_9GNAc_2$-PP-Dol is a Prerequisite for Capillary Endothelial Cell Proliferation", *Cell Molec. Biol.*, 45:137-152 (1999).

Cao et al., "Modified Method of Mammalian Cell Synchronization Improves Yield and Degree of Synchronization", *Exp. Cell Res.*, 193:405-410 (1991).

Millonig, "Advantages of a Phosphate Buffer for Osmium Tetroxide Solutions in Fixation", *J. Appl. Physics*, 32:1637 (1961).

Krishan, "Rapid Flow Cytofluorometric Analysis of Mammalian Cell Cycle by Propidium Iodide Staining", *J. Cell Biol.*, 66:188-193 (1975).

Fiorelli et al., "Cytokines from Activated T Cells Induce Normal Endothelial Cells to Acquire the Phenotypic and Functional Features of AIDS-Kaposi's Sarcoma Spindle Cells", *J. Clin. Invest.*, 95:1723-1734 (1995).

Granville et al., "Apoptosis: Molecular Aspects of Cell Death and Disease", *Lab. Invest.*, 78:893-913 (1998).

Martínez et al., "cAMP Blocks Apoptosis during Tunicamycin-induced Inhibition of Angiogenesis in virto", *FASEB Journal*, 13:600 (1999).

Martínez et al., "cAMP Rescues Unfolded Protein Response of Tunicamycin and Restores Cell-cycle Progression", *FASEB Journal*, 14:1308 (2000).

"OSI Pharmaceuticals Announces Initiation of Phase I Clinical Trial for Anti-Angiogenesis Agent", Press Release (2000).

Martínez et al., "Tunicamycin Inhibits Capillary Endothelial Cell Proliferation by Inducing Apoptosis", *Angiogenesis: From the Molecular to Integrative Pharmacology*, 197-208 (2000).

Martínez et al., "Tunicamycin Inhibits Angiogenesis by ER Stress", *Glycobiology*, 10:1131 (2000).

Banerjee et al., "Mannosylphosphodolichol Synthase Activity is Associated with a 32 kDa Phosphoprotein", *Bioscience Reports*, 19:169-177 (1999).

Boehringer Mannheim Corporation, Tunicamycin Data Sheet.

Dvorak et al., *The New England Journal of Medicine*, vol. 315, No. 26, pp. 1650-1659 (1986).

Baird et al., *Biochemical and Biophysical Research Communications*, vol. 126, No. 1, pp. 358-364 (1985).

Folkman et al., *American Journal of Pathology*, vol. 130, No. 2, pp. 393-400 (1988).

Smolin et al., *American Journal of Ophthalmology*, pp. 147-151 (1971).

Laniado-Schwartzman et al., *The Journal of Biological Chemistry*, vol. 269, No. 39, pp. 24321-24327 (1994).

Carlberg et al., *Carcinogenesis*, vol. 17, No. 12, pp. 2589-2596 (1996).

Chapman et al., *Ann. Rev. Cell Dev. Biol.*, 14, pp. 459-485 (1998).

Cai et al., *Journal of Cellular Physiology*, 177, pp. 282-288 (1998).

Klagsbrun et al., *Peptide Growth Factors and their Receptors II.*, Angiogenesis, Chapter 37, pp. 549-586 (1990).

Folkman, *Seminar in Cancer Biology*, vol. 3, pp. 65-71 (1992).

Mahadevan et al., *Rev. Oncologica*, vol. 29, pp. 97-103 (1990).

Weidner, *Seminars in Diagnostic Pathology*, vol. 10, No. 4, pp. 302-313 (1993).

Weidner, *Current Opinion in Obstetrics and Gynecology*, 7, pp. 4-9 (1995).

Weidner, *Seminars in Diagnostic Pathology*, vol. 12, No. 1, pp. 2-13 (1995).

Fidler et al., *Advances in Cancer Research*, The Biology of Cancer Invasion and Metastasis, vol. 28, pp. 149-250 (1978).

Weiss, *Fundamental Aspects of Metastasis*, Biophysical Aspects of the Metastatic Cascade, Chapter 3, pp. 51-70 (1976).

Bernstein et al., *Current Opinion in Oncology*, 6, pp. 106-113 (1994).

Folkman, *Thrombosis and Haemostasis*, Angiogenesis, 24, pp. 583-596 (1987).

Liotta et al., *Breast Cancer: Cellular and Molecular Biology*, pp. 223-238 (1988).

Kerbel et al., *Cancer Surveys*, Clonal Dominance of Primary Tumours by Metastatic Cells: Genetic Analysis and Biological Implications, vol. 7, No. 4, pp. 597-629 (1988).

Folkman, *Cancer Medicine*, Tumor Angiogenesis, Ch. 11, pp. 153-170 (1992).

Folkman, *Important Advances in Oncology*, Angiogenesis and Its Inhibitors, pp. 42-62 (1985).

Gross et al., *Proceedings of the American Association for Cancer Research*, vol. 31, p. 79 (1990).

Nicosia et al., *Clin. Expl. Metastasis*, vol. 4, No. 2, pp. 91-104 (1986).

Senger et al., *Cancer and Metastasis Reviews*, 12, pp. 303-324 (1993).

Kean, *Glycoconjugate Journal*, 13, pp. 675-680 (1996).

Zimmerman, *Yeast*, vol. 12, pp. 765-771 (1996).

Lee, *Current Opinion in Cell Biology*, vol. 4, pp. 267-273 (1992).

Tirasophon, *Genes & Development*, 12, pp. 1812-1824 (1998).

Majno et al., *Cells, Tissues, and Disease: Principle of General Pathology*, Chapter 4, pp. 123-173 (1996).

Struck et al., *The Biochemistry of Glycoproteins and Proteoglycans*, The Function of Saccharide-Lipids in Synthesis of Glycoproteins, Chapter 2, pp. 35-83 (1980).

Vindelov, *Virchows Arch. B Cell Path*, 24, pp. 227-242 (1977).

Sugino et al., "Stromal Invasion is Not Essential to Blood-borne Metastasis in Mouse Mammary Carcinoma", Scientific Program Booklet of the Pathological Society of Great Britain and Ireland, 170th Meeting, Abstract # 161 (1995).

Chang et al., *Experimental Neurology*, vol. 137, pp. 201-211 (1996).

Leibovich et al., *Nature*, vol. 329, pp. 630-632 (1987).

Banerjee, "Angiogenesis: Characterization of a Cellular Model", *Puerto Rico Hlth. Sci. J.*, 17:327-333, Jan. 1999.

Kessler et al., "Mast Cells and Tumor Angiogenesis", *Intern. J. Can.*, 18:703-709 (1976).

Nguyen et al., "A Role of Sialyl Lewis-X/A Glycoconjugates in Capillary Morphogenesis", *Nature*, 365:267-269 (1993).

\* cited by examiner

Fig. 2
32h 40h
Fig. 2A
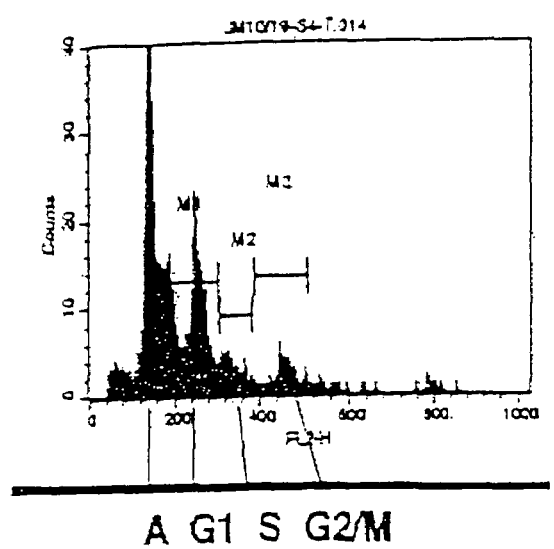
A G1 S G2/M
(M1) (M2) (M3)
Fig. 2B

Fig. 3
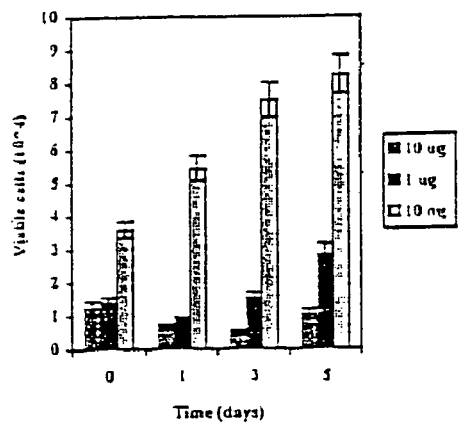
Fig. 3A
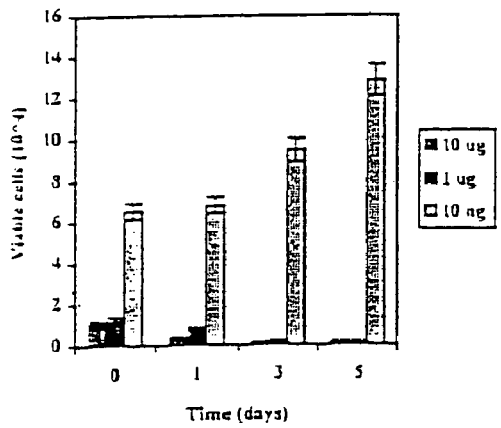
Fig. 3B

Fig. 4
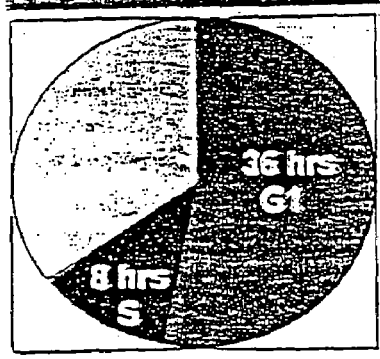
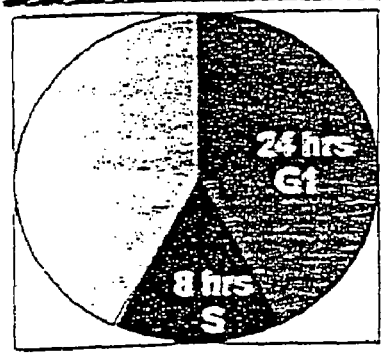
Fig. 4A
Fig. 4B

Fig. 6
Fig. 6A
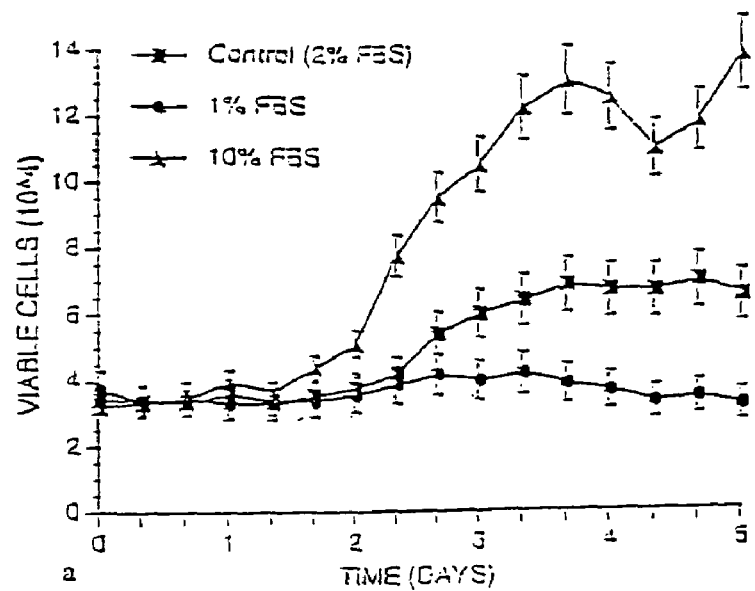
Fig. 6B
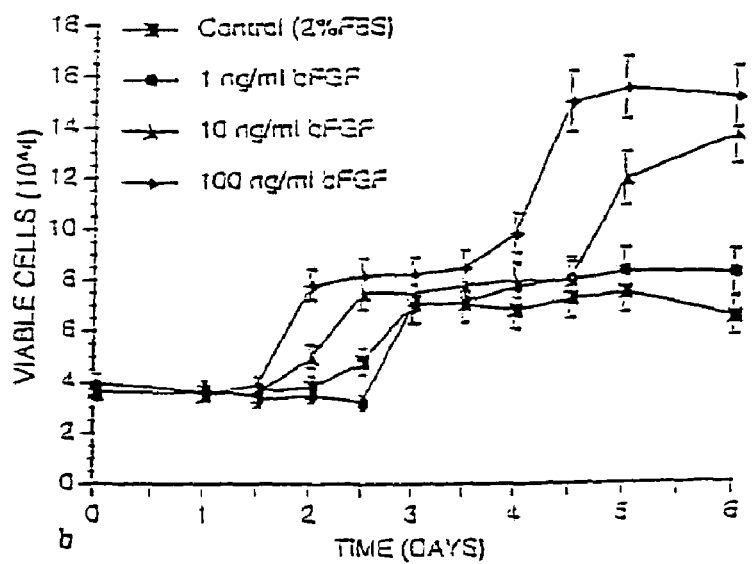

Fig. 7
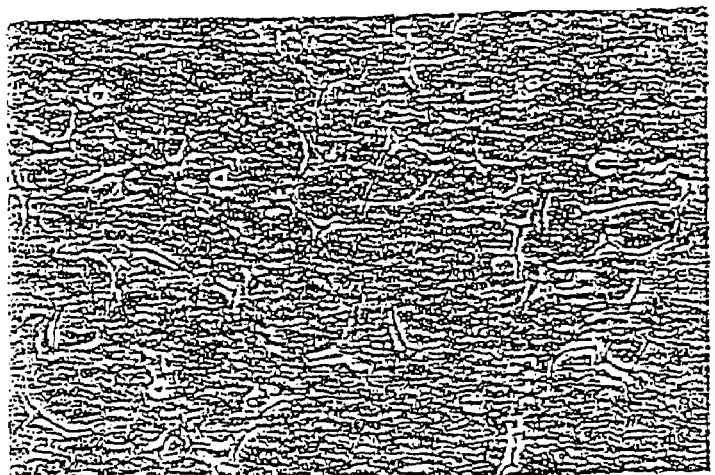
Fig. 7A
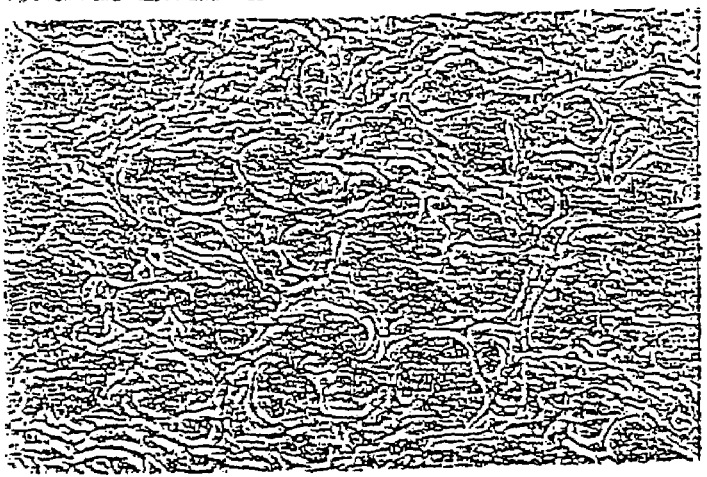
Fig. 7B
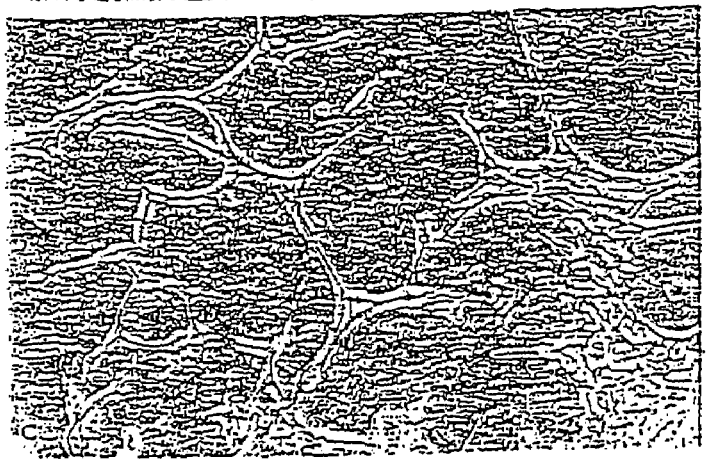
Fig. 7C

Fig. 7
Fig. 7F
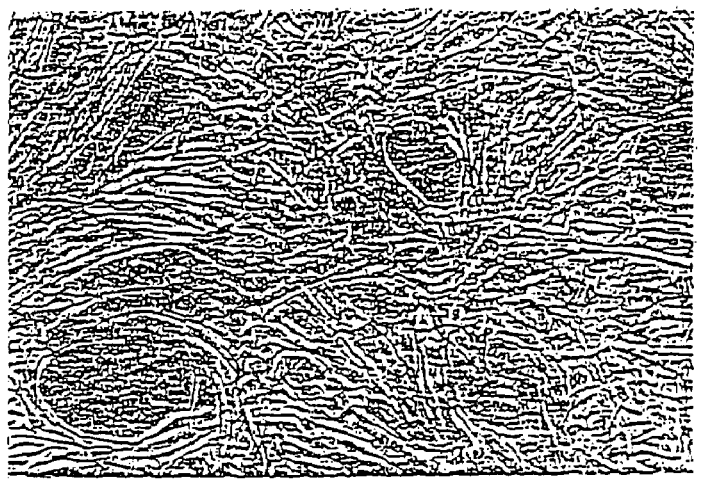
Fig. 7E
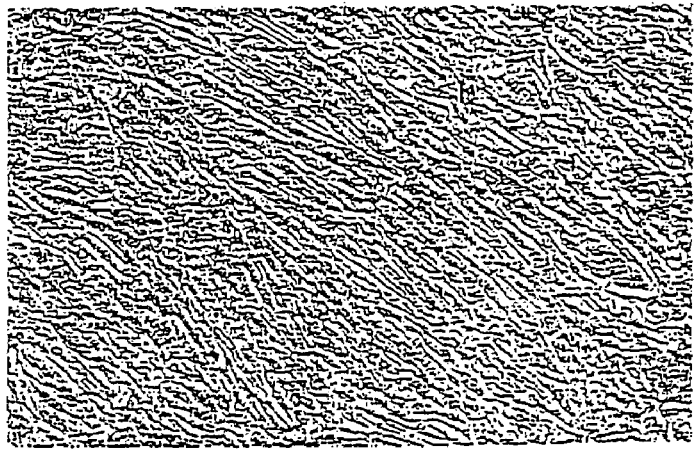
Fig. 7D
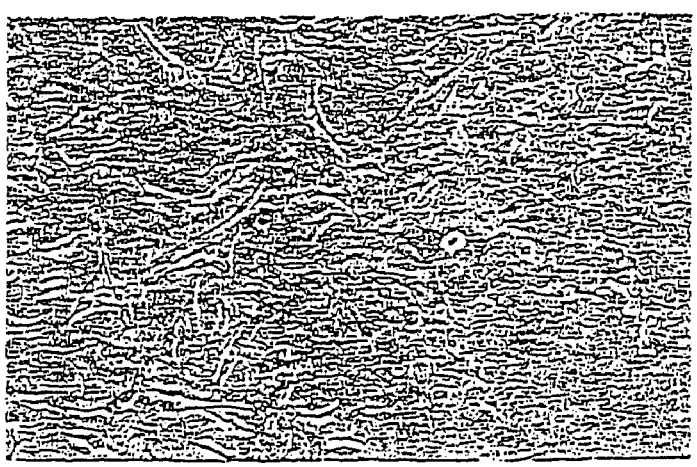

Fig. 9
Fig. 9A
Fig. 9B
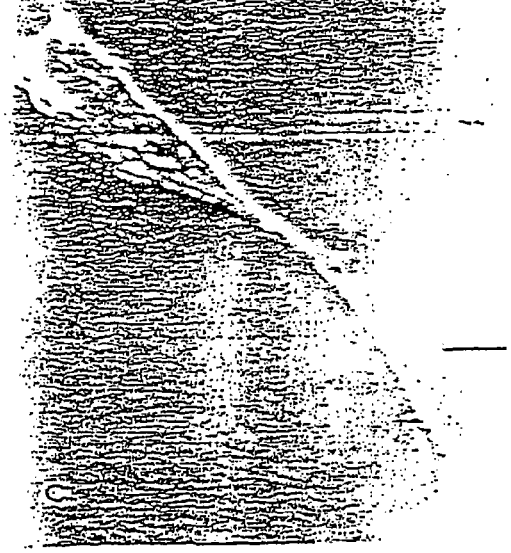
Fig. 9C

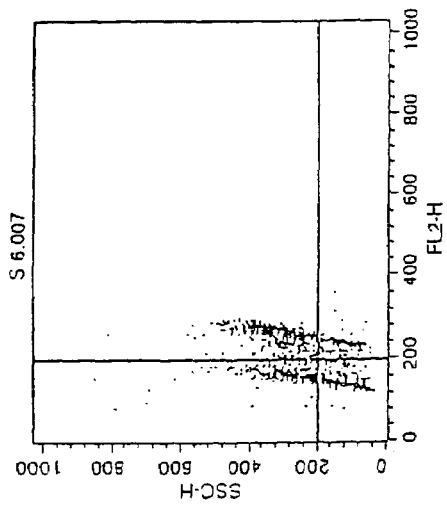
Fig. 10
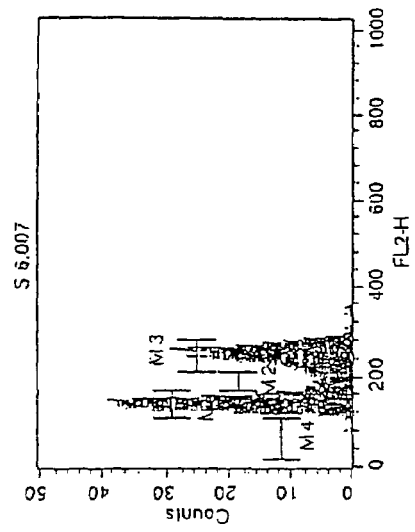
Fig. 10D
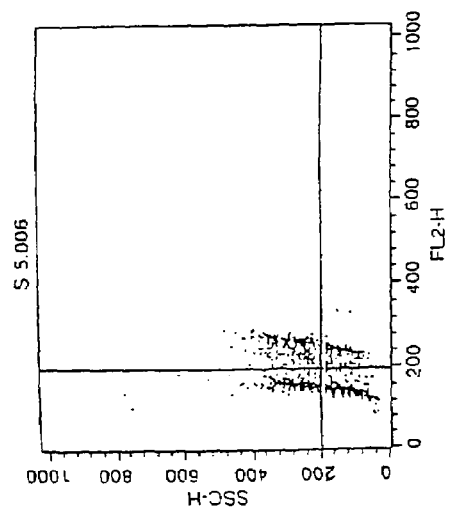
Fig. 10C
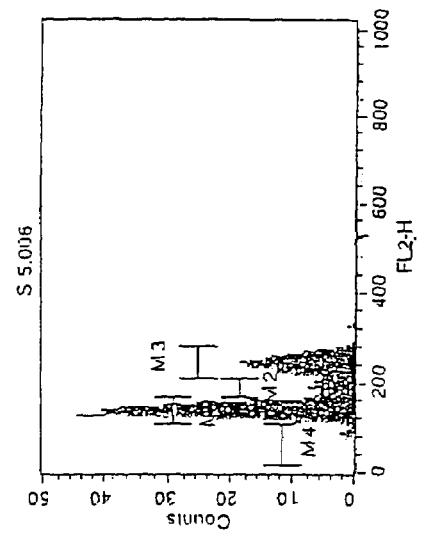

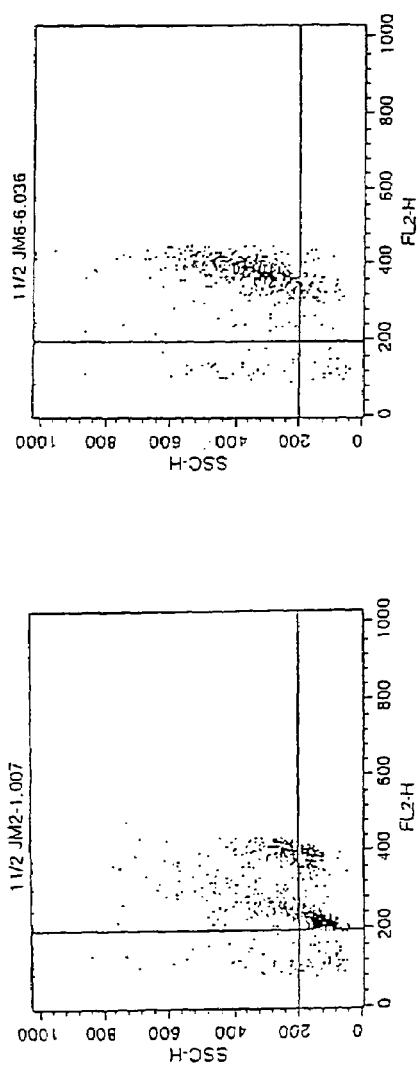
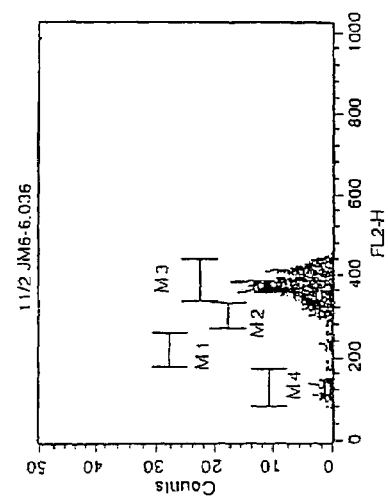
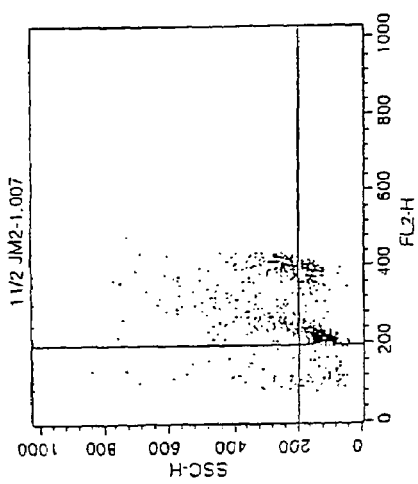
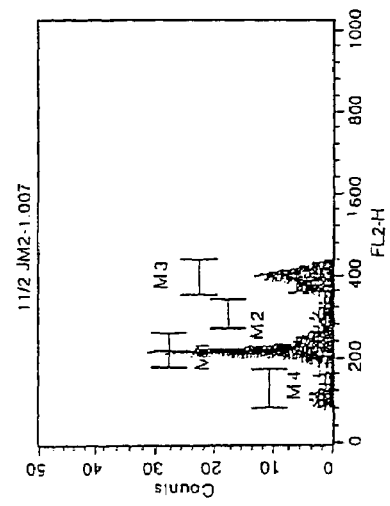
Fig. 11
Fig. 11A
Fig. 11B

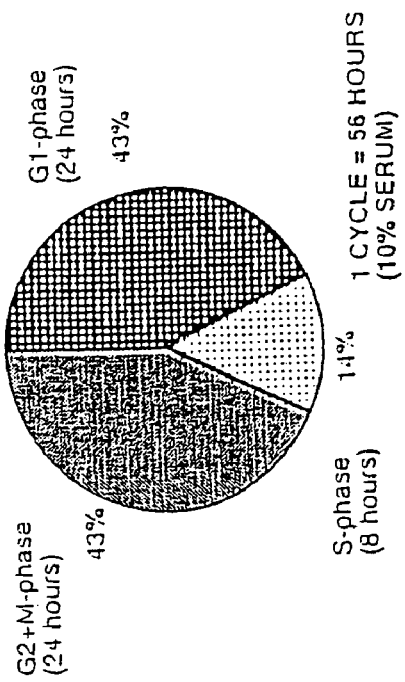
Fig. 11
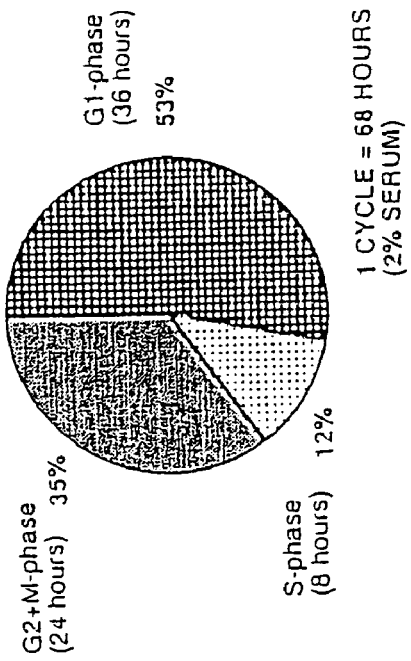
Fig. 11D
Fig. 11C

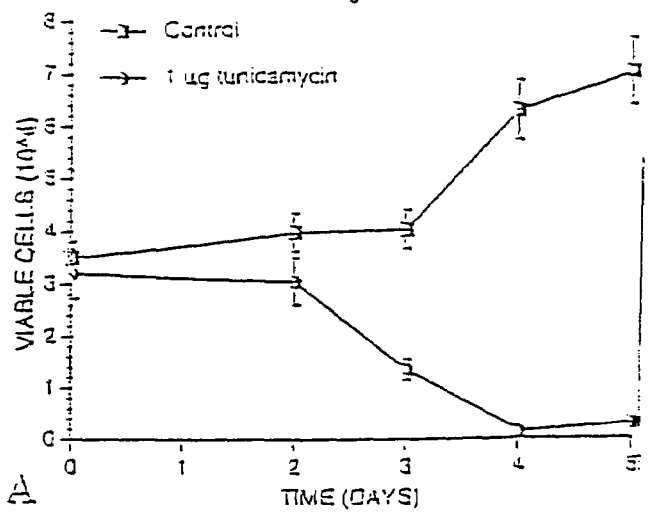
Fig. 13
Fig. 13A
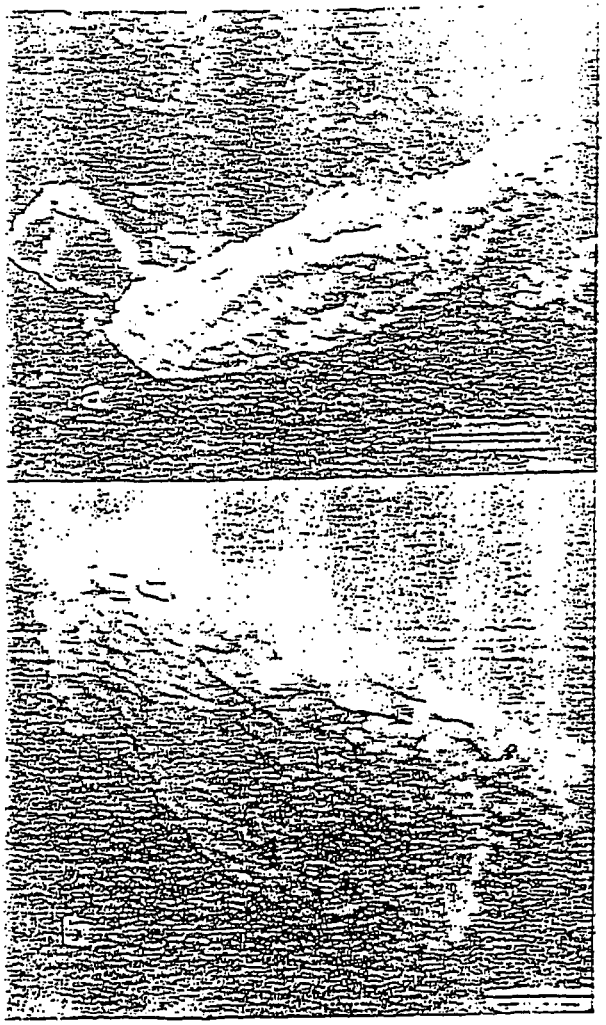
Fig. 13E
Fig. 13F

Fig. 13
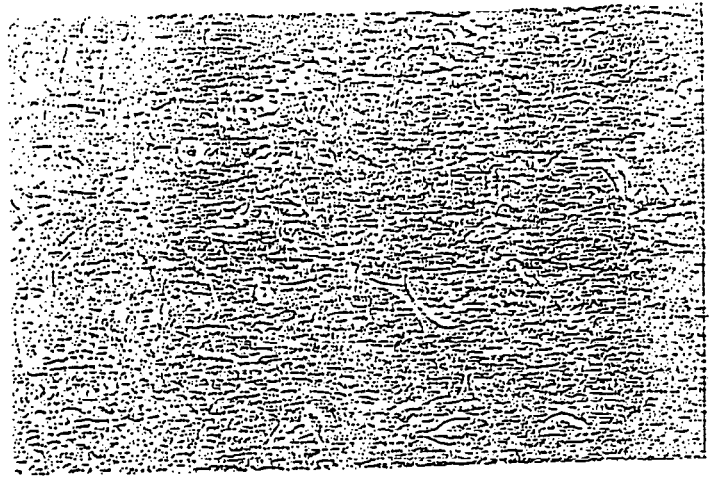
Fig. 13B
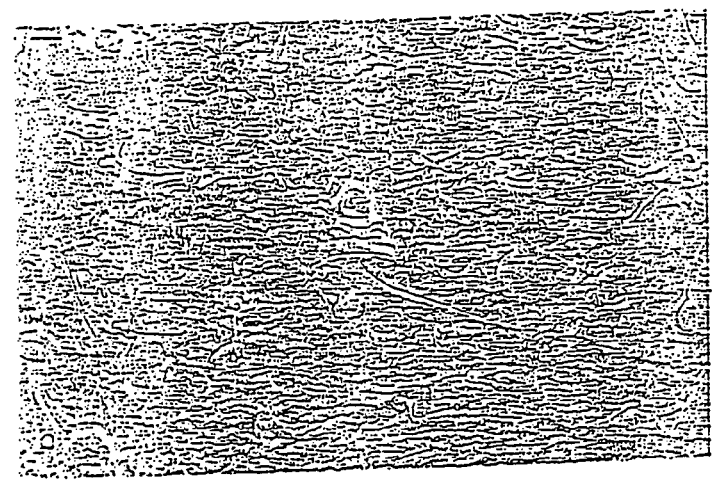
Fig. 13C
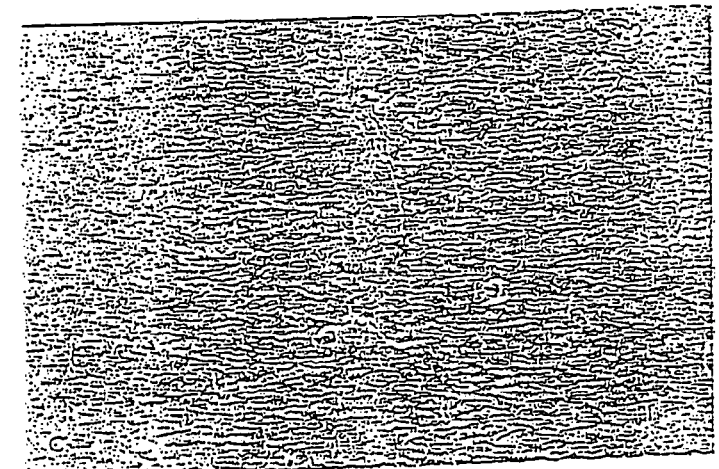
Fig. 13D

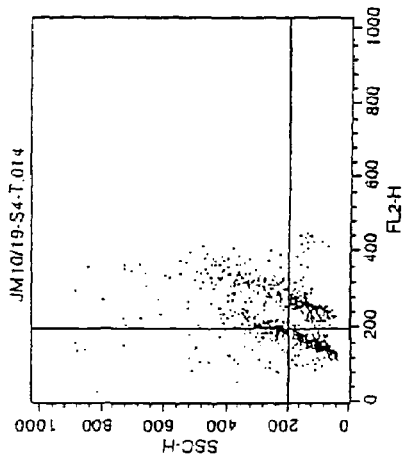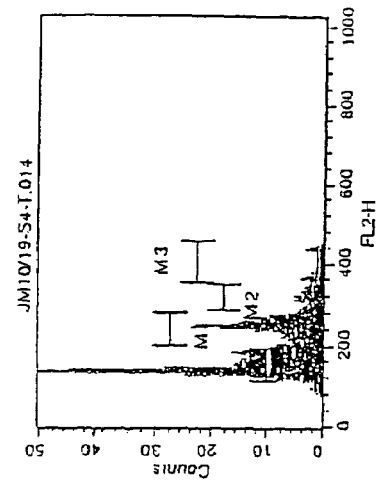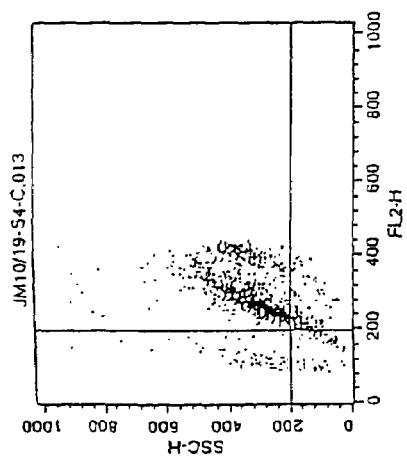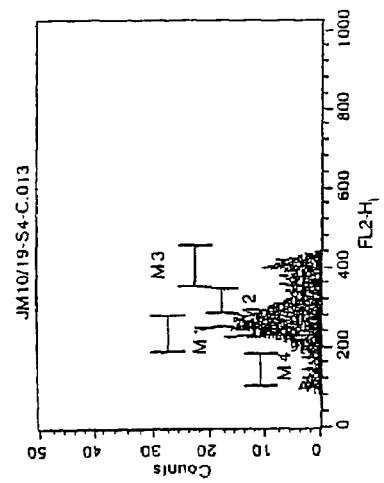
Fig. 13
Fig. 13G
Fig. 13H

METHODS FOR INHIBITING ANGIOGENESIS

CROSS-REFERENCE TO RELATED APPLICATIONS

The present application claims the priority under 35 U.S.C. §119(e) of U.S. Provisional Application No. 60/181,312, filed Feb. 9, 2000, the disclosure of which is expressly incorporated by reference herein in its entirety.

BACKGROUND OF THE INVENTION

1. Field of the Invention

The present invention relates to methods for inhibiting angiogenesis. Thus, the present invention relates to methods of inhibiting the growth of capillary endothelial cells which form new blood microvessels. Accordingly, the present invention is directed to treating disease states, e.g., tumors such as malignant and benign tumors, characterized by an abnormally high amount of angiogenesis.

2. Discussion of Background Information

Endothelial cell proliferation and differentiation into blood capillaries (i.e., angiogenesis) are essential for growth and development, wound healing, osteogenesis, etc. Endothelial cells in adult tissues are quiescent but rapid proliferation occurs for a limited period of time during menstruation, ovulation, reproduction, implantation, mammary gland changes during lactation, and wound healing, as discussed in COCKERILL et al., "Angiogenesis: Model and Modulators", *Int Rev Cytol,* 159: 113-160 (1995); and FOLKMAN et al., "Angiogenesis", *J Biol Chem,* 267:10931-10934 (1992), the disclosures of which are herein incorporated by reference in their entireties.

Angiogenesis involves the development of new and small blood vessels by budding and sprouting from larger, extant vessels, as disclosed in BECK et al., "Vascular Development: Cellular and Molecular Regulation", *FASEB J.,* 11:365-373 (1997); and BUSSOLINO et al., "Molecular Mechanisms of Blood Vessel Formation", *TIBS,* 22:251-256 (1997), the disclosures of which are herein incorporated by reference in their entireties. In normal physiological states, angiogenesis is a tightly regulated and self-limited process, as disclosed in COCKREILL et al. (1995), cited above; and KLAGSBRUN et al., "Angiogenesis", *Peptide Growth Factors and their Receptors II,* pp. 549-586 (1990), the disclosures of which are herein incorporated by reference in their entireties.

Abnormal or uncontrolled angiogenesis is a prominent feature in various disease states including diabetic retinopathy, arthritis, hemangiomas, psoriasis, etc. In addition, abnormal capillary growth is an important step during the transition from hyperplasia to neoplasia and metastasis, and is critical for the growth and maintenance of many types of benign and malignant tumors, as disclosed in FOLKMAN, "The Role of Angiogenesis in Tumor Growth", *Seminar in Cancer Biol.,* 3:65-71 (1992); FOLKMAN et al., "Induction of Angiogenesis During the Transition from Hyperplasia to Neoplasia", *Nature* 339: 58-61 (1989); FRIEDLANDER et al., "Definition of Two Angiogenic Pathways by Distinct $\alpha_v$ Integrins", *Science,* 270:1500-1502 (1995); LIOTTA et al., "Cancer Metastasis and Angiogenesis: an Imbalance of Positive and Negative Regulation", *Cell,* 64:327-336 (1991); SACLARIDES et al., "Tumor Angiogenesis and Rectal Carcinoma", *Dis. Colon Rectum,* 37:921-926 (1994); and SHWEIKI et al., "Patterns of Expression of Vascular Endothelial Factor (VEGF) and VEGF Receptors in Mice Suggest a Role in Hormonally Regulated Angiogenesis", *J. Clin. Invest.,* 91:2235-2243 (1993), the disclosures of which are herein incorporated by reference in their entireties.

Tumor growth is angiogenesis dependent. In breast carcinoma, intratumoral endothelial cells proliferate 45 times faster than endothelial cells in adjacent benign stroma, and the rate of tumor progression correlates with increased intratumoral microvascular density. Neovascularization supports tumor growth by allowing "perfusion" of nutrients, oxygen, and waste products through a crowded cell population. In addition, endothelial cells also release important "paracrine" growth factors for tumor cells.

It has been observed that in human breast carcinomas the intratumoral endothelial cell proliferation index (mean 2.7%) is 45-fold greater than that of the surrounding benign breast, as disclosed in VARTANIAN et al., "Correlation of Intratumoral Endothelial Cell Proliferation with Microvessel Density (Tumor Angiogenesis) and Tumor Cell Proliferation in Breast Carcinoma", *Am. J. Pathol.,* 144:1188-1194 (1994), the disclosure of which is herein incorporated by reference in its entirety. The value of 2.7% however is unexpectedly low, especially given the much higher intratumoral microvascular density compared to adjacent benign stroma. This has suggested that a significant component of the angiogenic process is due to endothelial cell migration, capillary budding, establishment of capillary loops, and/or neovascular remodeling, as disclosed FOLKMAN et al., "Angiogenic Factors", *Science,* 235:442-447 (1987); FURCHT, "Critical Factors Controlling Angiogenesis: Cell Products, Cell Matrix, and Growth Factors", *Lab. Invest.,* 55:505-509 (1986); DENEKAMP, "Angiogenesis, Neovascular Proliferation and Vascular Pathophysiology as Targets for Cancer Therapy", *Br. J. Radiol.,* 66:181-196 (1993); and MAHADEVAN et al., "Metastasis and Angiogenesis", *Rev. Oncol.,* 3:97-103 (1990), the disclosures of which are herein incorporated by reference in their entireties.

The association between intratumoral microvascular density and the incidence of metastases (a process by which a cancer cell leaves a primary tumor and migrates through the blood or lymph system to a new tissue or organ, where a secondary tumor grows) has been reported for invasive breast carcinoma as well as for melanoma, prostrate carcinoma, testicular carcinoma, ovarian carcinoma, rectal carcinoma, bladder carcinoma, central nervous system tumors, multiple myeloma, non-small-cell lung carcinomas, and squamous carcinoma, as disclosed in WEIDNER, "Tumor Angiogenesis: Review of Current Applications in Tumor Prognostication", *Semin. Diagn. Pathol.,* 10:302-313 (1993); WEIDNER, "Prognostic Factors in Breast Carcinoma", *Curr. Obstet. Gynedcol.,* 7:4-9 (1995); and WEIDNER, "Malignant Breast Lesions that Mimic Benign Tumors", *Semin. Diagn. Pathol.,* 12:2-13 (1995), the disclosures of which are herein incorporated by reference in their entireties. Invasive breast carcinoma from patients with metastases has a mean microvessel count of 101 per 200× filed (s.d=49.3, range 16-220), whereas without metastases the corresponding value is 45 per 200×filed (s.d=21.1, range 15-100). Univariate analysis has revealed these differences are statistically significant (p=0.003).

To metastasize, a tumor cell must successfully negotiate a series of obstacles. For example, tumor cells must gain access to the vasculature from the primary tumor, survive the circulation, escape immune surveillance, localize in the microvasculature of the target organ, escape from the vasculature into the target organ, and induce angiogenesis, as disclosed in FIDLER et al., "The Biology of Cancer Invasion and Metastasis", *Adv. Cancer Res.,* 28:149-250 (1978);

NICOLSON, "Cancer Metastasis", *Sci. Am.*, 240:66-76 (1979); WEISS, "Biophysical Aspects of the Metastatic Cascade", *Fundamental Aspects of Metastasis*, pp. 51-70 (1976); BERNSTEIN et al., "Molecular Mediators of Interactions with Extracellular Matrix Components in Metastasis and Angiogenesis", *Curr. Opin. Oncol.*, 6:106-113 (1994); NAGY et al., "Pathogenesis of Tumor Stroma Generation: a Critical Role for Leaky Blood Vessels and Fibrin Deposition", *Biochim Biophys. Acta*, 948:305-326 (1989); MOSCATELLI et al., "Angiogenic Factors Stimulate Plasminogen Activator and Collagenase Production by Capillary Endothelial Cells", *J. Cell Biol.*, 91:201a (1981); FOLKMAN, "Angiogenesis", *Thrombosis and Haemostasis*, 24:583-596 (1987); LIOTTA et al., *Breast Cancer: Cellular and Molecular Biology*, pp. 223-238 (1988); LIOTTA et al., "The Significance of Hematogenous Tumor Cell Clumps in the Metastatic Process", *Cancer Res.*, 36:889-894 (1976); KERBEL et al., "Clonal Dominance of Primary Tumors by Metastatic Cells: Genetic Analysis and Biological Implications", *Cancer Surv.*, 7:597-629 (1988); FOLKMAN, "Tumor Angiogenesis", *Canc. Med.* (Chapter 11) (1992); and SUGINO et al., "Stromal Invasion is Not Essential to Blood-borne Metastasis in Mouse Mammary Carcinoma", *Scientific Program Booklet of the Pathological Society of Great Britain and Ireland*, 170$^{th}$ Meeting, Abstract # 161 (1995), the disclosures of which are herein incorporated by reference in their entireties. Tumor growth is angiogenesis dependent, as disclosed in FOLKMAN, "Tumor Angiogenesis: Therapeutic Implications", *N. Engl. J. Med.*, 285:1182-1186 (1971), the disclosure of which is herein incorporated by reference in its entirety. In addition, tumor cells and blood vessels compose an integrated ecosystem in which endothelial cells could be "switched" from a resting state to a rapidly growing state by a diffusible signal from tumor cells or associated inflammatory cells.

The direct evidence, supporting that tumor growth is angiogenesis dependent, is that various methods of inhibiting angiogenesis, which are not cytostatic to tumor cells in vitro, inhibit tumor growth in vivo, as disclosed in FOLKMAN, "Angiogenesis and its Inhibition", *Important Advances in Oncology*, pp. 42-62 (1985); FOLKMAN, "Clinical Applications of Research on Angiogenesis", *N. Engl. J. Med.*, 333:1757-1763 (1995); HARRIS et al., "Gene Therapy Through Signal Transduction Pathways and Angiogenic Growth Factors as Therapeutic Targets in Breast Cancer", *Cancer*, 74:1021-1025 (1994); INGBER et al., "Synthetic Analogues of Fumagillin that Inhibit Angiogenesis and Suppress Tumor Growth", *Nature*, 348:555-557 (1990); GROSS et al., "Modulation of Solid Tumor Grown in vivo by bFGF", *Proc. Am. Assoc. Cancer Res.*, 31:79 (#469) (1990); HORI et al., "Suppression of Solid Tumor Growth by Immunoneutralizing Monoclonal Antibody Against Human Basic Fibroblast Growth Factor", *Cancer Res.*, 51:6180-6184 (1991); KIM et al., "Inhibition of Vascular Endothelial Growth Factor-induced Angiogenesis Suppresses Tumor Growth in vivo", *Nature*, 362:841-844 (1993); MILLAUER et al., "Glioblastoma Growth Inhibited in vivo by a Dominant-negative Flk-1 Mutant", *Nature*, 367:576-579 (1994); BROOKS, "Integrin αvβ3 Antagonists Promote Tumor Regression by Inducing Apoptosis of Angiogenic Blood Vessels", *Cell*, 79:1157-1164 (1994); and NICOSIA et al., "Interactions Between Newly Formed Endothelial Channels and Carcinoma Cells in Plasma Clot Culture", *Clin. Exp. Metastasis*, 4:91-104 (1986), the disclosures of which are herein incorporated by reference in their entireties.

Tumor neovascularization allows growth because the new vessels allow exchange of nutrients, oxygen and waste products by a crowded cell population for which simple diffusion of these substances across its outer surfaces is no longer adequate. In addition to this "perfusion effect", endothelial cells also release important "paracrine" growth factors for tumor cells (e.g., bFGF/FGF-2, IGF-2, PDGF, and colony stimulating factors), as disclosed in NICOSIA (1986), cited above; RAK et al., "Progressive Loss of Sensitivity to Endothelium-derived Growth Inhibitors Expressed by Human Melanoma Cells during Disease Progression", *J. Cell Physiol.*, 159:245-255 (1994); and HAMADA et al., "Separable Growth and Migration Factors for Large-cell Lymphoma Cells Secreted by Microvascular Endothelial Cells Derived from Target Organs for Metastasis", *Br. J. Cancer*, 66:349-354 (1992). Also, the invasive chemotactic behavior of endothelial cells at the tips of growing capillaries is facilitated by their secretion of collagenases, urokinases, and plasminogen activator, as disclosed in FOX et al., "High Levels of uPA and pA-1 are Associated with Highly Angiogenic Breast Carcinomas", *J. Pathol.*, 170:388a (1993); and MOSCATELLI et al., "Angiogenic Factors Stimulate Plasminogen Activator and Collagenase Production by Capillary Endothelial Cells", *J Cell Biol.*, 91:201a (1981), the disclosures of which are herein incorporated by reference in their entireties. These degradative enzymes facilitate spreading of tumor cells into and through the adjacent fibrin-gel matrix and connective tissue stroma. Indeed, elevated levels of urokinase-type plasminogen activator (uPA) and plasminogen activator inhibitor-1 (PA-1) in breast carcinoma have been shown to be independent predictors of poor prognosis. A significant association of uPA and PA-1 with intratumoral microvascular density however, has led to the conclusion that the poor prognosis in breast carcinomas associated with elevated uPA and PA-1 may be due to an interaction between endothelial and tumor cells using the uPA enzyme system, as disclosed in FOX et al. (1993), cited above, the disclosure of which is herein incorporated by reference in its entirety. Thus, the additive impact of the "perfusion and paracrine" tumor effects, plus the endothelial-cell derived invasion-associated enzymes, all contribute to a phase of rapid tumor growth and signal a "switch" to a potentially lethal angiogenesis phenotype.

The process of tumor neovascularization shares many features with normal wound healing, as disclosed in DVORAK, "Tumors: Wounds that do not Heal. Similarities between Tumor Stroma Generation and Wound Healing", *N. Engl. J. Med.*, 315:1650-1659 (1986), the disclosure of which is herein incorporated by reference in its entirety, and is likely mediated by similar and specific angiogenic molecules (e.g., VEGF), which are released by the tumor cells and/or host immune cells into the stroma or possibly mobilized from a bound inactive state within the tumor stroma (e.g., FGF-1), as disclosed in FOLKMAN et al. (1987); FOLKMAN (1995); and MOSCATELLI et al. (1981), all cited above, the disclosures of which are herein incorporated by reference in their entireties. In addition to tumor cells, inflammatory cells may also be important in tumor angiogenesis. Stimulated macrophage can secrete angiogenic factors, such as TGFα, angiotropin, TNFα, and bFGF/FGF-2, as disclosed in FOLKMAN (1995), cited above; POLVERINI et al., "Induction of Neovascularization in vivo and Endothelial Proliferation in vitro by Tumor Associated Macrophages", *Lab. Invest.*, 51:635-642 (1984); BAIRD et al., "Immunoreactive Fibroblast Growth Factor in Cells of Peritoneal Exudate Suggests its Identity with Macrophage-derived Growth Factor", *Biochem. Biophys. Res. Commun.*, 126:358-364 (1985); FRATER-SCHRODER et al., "Tumor Necrosis Factor Type a, a Potent Inhibitor of Endothelial Cell Growth in vitro, is Angiogenic in vivo", *Proc. Natl. Acad. Sci (USA)*, 84:5277-5281 (1987); LEIBOVICH et al., "Macrophage-induced Angiogenesis Mediated by Tumour Necrosis Factor-α", *Nature*, 329:630-632 (1987); SCHREIBER et al., "Transforming Growth Factor-alpha: a More Potent Angiogenic Mediator than Epidermal Growth Factor", *Science*, 232:1250-1253 (1986); HOCKEL et al., "Purified Monocyte-derived Angiogenic Substance (Angiotropin) Induces Controlled Angiogenesis Associated with Regulated Tissue Proliferation in Rabbit Skin", *J. Clin. Invest.*, 82:1075-1090 (1988); and FOLKMAN et al., "A Heparin-binding Angiogenic Protein—Basic Fibroblast Growth Factor—is Stored within Basement Membrane", *Am. J. Pathol.*, 130:393-400 (1988), the disclosures of which are herein incorporated by reference in their entireties.

Clearly, many tumors have associated macrophages, which may amplify tumor angiogenesis, especially when activated by high intratumoral lactate levels caused by tumor hypoxia, as disclosed in FOLKMAN (1988), cited above, the disclosure of which is herein incorporated by reference in its entirety. Also, some human tumors are infiltrated by mast cells, as disclosed in SMOLIN, "Lymphatic Drainage from Vascularized Rabbit Cornea", *Am J. Opthalmol.*, 72:147-151 (1971); and KESSLER et al., "Mast Cells and Tumor Angiogenesis", *Intern. J. Can.*, 18:703-709 (1976), the disclosures of which are herein incorporated by reference in their entireties. Mast cells are rich in heparin, a substance known to mobilize bFGF/FGF-2 from the extracellular matrix, protect it from degradation, and potentiates its angiogenic effects, as disclosed in THORNTON et al., "Human Endothelial Cells: Use of Heparin in Cloning and Long-term Serial Cultivation, *Science*, 222:623-625 (1983), the disclosure of which is herein incorporated by reference in its entirety. Furthermore, when tumors are implanted in mast cell deficient mice (W/W$^v$), angiogenesis and tumor growth are inhibited to less than 60% of that observed in mice having normal mast cells numbers, as disclosed in DETHLEFSEN et al., "Tumor Growth and Angiogenesis in Wild Type and Mast Cell Deficient Mice", *FASEB J.*, 4:A623 (1990), the disclosure of which is herein incorporated by reference in its entirety. Tumor angiogenesis and tumor growth however have increased when these mast cell deficient mice are injected with exogenous mast cells along with the original bolus of tumor cells. Finally, stimulated tumor-infiltrating lymphocytes may also play a role in tumor angiogenesis by secreting cytokines that activate other inflammatory cell types, and/or chemo-attractants for other immune cells.

Angiogenesis is a complex biochemical process, and it is often difficult to study the molecular mechanism in vivo due to interference by a multitude of factors. The exact molecular details of angiogenesis (normal or abnormal) are not fully understood. It is known, however, that the sequence of events of angiogenesis involve DNA synthesis and vascular remodeling. Angiogenesis occurs in stages that orchestrate a network of cooperative interactions which include: (I) the initiation phase, characterized by increased cell membrane permeability; (ii) progression, constituted by the production of proteolytic enzymes that degrade the extracellular matrix and promote endothelial cell migration, and the entry of cells into either a proliferative or an apoptotic response; (iii) differentiation into new vessels; and (iv) the stabilization and maturation of vessels by mediator molecules that recruit mesenchymal cells to vessel walls, as discussed in COCK-ERILL et al. (1995); KLAGSBRUN et al. (1990); and SHWEIKI et al. (1993), all cited above, the disclosures of which are herein incorporated by reference in their entireties.

The sequence of events of angiogenesis include (i) growth of endothelial cells from small venules lacking a muscle wall; (ii) secretion of collagenases and degradation of basement membranes and connective-tissue stroma; (iii) movement of endothelial cells toward the source of the angiogenic stimulus; (iv) proliferation of endothelial cells; (v) elongation of the endothelial sprout; (vi) joining of one sprout with another to form a capillary loop; (vii) formation of a cytoplasmic vacuole with subsequent complete lumen formation and blood flow; and (viii) deposition of a new basement membrane, as disclosed in BECK et al. (1997); and BUSSOLINO et al. (1997), both cited above, the disclosures of which are herein incorporated by reference in their entireties.

Although the exact molecular mechanisms of the angiogenic process (normal or abnormal) are currently not fully understood, it is known that inducers of angiogenesis can act directly on endothelial cells, or indirectly, via accessory cells (monocytes, mastocytes, T cells and so on).

Although the list of factor(s) and/or cell(s) causing tumor angiogenesis remains incomplete, the current leading candidates for this role include bFGF/FGF-2 and VEGF, as disclosed in KANDEL et al., "Neovascularization is Associated with a Switch to the Export of bFGF in the Multi-step Development of Fibrosarcoma", *Cell*, 66:1095-1104 (1991); NGUYEN et al., "Elevated Levels of the Angiogenic Peptide Basic Fibroblast Growth Factor in Urine of Bladder Cancer Patients", *J. Natl. Cancer Inst.*, 85:241-242 (1993); and HORI et al., "Suppression of Solid Tumor Growth by Immunoneutralizing Monoclonal Antibody Against Human Basic Fibroblast Growth Factor", *Cancer Res.*, 51:6180-6184 (1991), the disclosures of which are herein incorporated by reference in their entireties. Other possible angiogenic factors include: FGF-1, TGFα, TGFβ, platelet-derived endothelial cell growth factor (PD-ECGF), vascular permeability factor (VPF), folliculostellate-derived growth factor (FSDGF), granulocyte colony stimulating factor, placental growth factor, interleukin-8, hepatocyte growth factor, angiotropin, angiogenin, and TNFα, as disclosed in FOLKMAN et al. (1995); FOLKMAN (1995); and MOSCATELLI (1981), all cited above, the disclosures of which are herein incorporated by reference in their entireties. The amino acid sequences of VEGF, VPF, and FSDGF are nearly identical and likely represent the same substrate. In fact, VEGF is often designated VPF/VEGF. It has been shown in a variety of solid tumor types that tumor cells express high levels of VEGF protein and mRNA. In contrast, tumor endothelial cells express VEGF protein but not VEGF mRNA. Yet, the same endothelial cells express high levels of mRNA for the VEGF receptors Flt-1 and KDR, indicating that the endothelial-cell staining likely reflects binding of VEGF protein secreted by adjacent tumor cells. Moreover, VEGF has shown to induce in endothelial cells expression of plasminogen activator, plasminogen activator inhibitor, interstitial collagenase, and procoagulant activity, as disclosed in BROWN et al., "Increased Expression of Vascular Permeability Factor (Vascular Endothelial Growth Factor) and its Receptors in Kidney and Bladder Carcinomas", *Am J. Pathol.*, 143:1255-1262 (1993), the disclosure of which is herein incorporated by reference in its entirety. VEGF promotes extravasation of plasma fibrinogen, leading to fibrin deposition within the tumor matrix, a process that promotes the ingrowth of macrophages, fibroblasts, and endothelial cells, as disclosed in SENGER et al., "Vascular Permeability Factor (VPF, VEGF) in Tumor Biology", *Can Met Rev.*, 12:303-324 (1993), the disclosure of which is herein incorporated by reference in its entirety. In addition, it has been suggested that VEGF and bFGF/FGF-2 act in a synergistic manner to cause tumor angiogenesis, as disclosed in GOTO et al., "Synergistic Effects of Vascular Endothelial Growth Factor and Basic Fibroblast Growth Factor on the Proliferation and Cord Formation of Bovine Capillary Endothelial Cells within Collagen Gels", *Lab. Invest.*, 69:508-517 (1993), the disclosure of which is herein incorporated by reference in its entirety.

Various low molecular weight, non-peptide angiogenic factors have also been reported. These include 1-butyryl-glycerol, prostaglandins E1 and E2 (PEG1 and PEG2), nicotinamide, adenosine, nitric oxide, hyaluronic acid degradation products, an arachidonic acid metabolites named 12(R)-hydroxyeicosatrienoic acid (12[R]-HETrE), 8Br-cAMP, estrogens (17β-estradiol), as disclosed in FOLKMAN et al. (1987), cited above; FOLKMAN (1995), cited above; LEIBOVICH et al., "Production of Angiogenic Activity by Human Monocytes Requires an L-arginine/nitric oxide-synthase-dependent Effector Mechanism", *Proc. Natl. Acad. Sci (USA)*, 91:4190-4194 (1994); LANIADO-SCHWARTZMAN et al., "Activation of Nuclear Factor κβ and Oncogene Expression by 12(R)-hydroxyeicosatrienoic acid, an Angiogenic Factor in Microvessel Endothelial Cells", *J. Biol. Chem.*, 269:24321-24327 (1994); BANERJEE, "Microenvironment of Endothelial Cell Growth and Regulation of Protein N-glycosylation", *Indian J. Biochem. Biophys.*, 25:8-13 (1988); and BANERJEE et al., "Biphasic Estrogen Response on Bovine Adrenal Medulla Capillary Endothelial Cell Adhesion, Proliferation and Tube Formation", *Mol. Cell Biochem.*, 177:97-105 (1997). When endothelial cells are stimulated by 12(r)-HETrE, the proto-oncogenes c-myc, c-jun, and c-fos are activated, as disclosed in LANIADO-SCHWARTZMAN et al. (1988), cited above, the disclosure of which is incorporated herein by reference in its entirety.

Inactivation of a suppressor gene resulting in loss of an angiogenic suppressor substance may allow tumor angiogenesis to proceed. Indeed, the switch to active angiogenesis and the rate of the angiogenic process are likely the net effect of both stimulatory and inhibitory factors. For example, it has been shown that inactivation of a suppressor gene during carcinogenesis results in increased angiogenesis that parallels increased tumorigenicity, as disclosed in BOND et al., "Replacement of Residues of 8-22 of Angiogenin with 7-21 of RNASE-A Selectively Affects Protein-synthesis Inhibition and Angiogenesis", *Biochemistry*, 29:3341-3349 (1990); and BOUCK et al., "Coordinate Control of Anchorage Independence, Actin Cytoskeleton and Angiogenesis by Human Chromosome 1 in Hamster-human Hybrids", *Cancer Res.*, 46:5101-5105 (1986), the disclosures of which are herein incorporated by reference in their entireties. During this process there is a 10-fold decrease in the secretion of an angiogenesis inhibitor 140 kDa glycoprotein, thrombospondin, as disclosed in RASTINEJAD et al., "Regulation of the Activity of a New Inhibitor of Angiogenesis by a Cancer Suppressor Gene", *Cell*, 56:345-355 (1989), the disclosure of which is herein incorporated by reference in its entirety.

Somatic hybrid cells produced by fusion of MCF-7 human breast carcinoma cells with normal immortalized human mammary epithelial cells are suppressed in their ability to form tumors in nude mice, as disclosed in ZAJCHOWSKI et al., "Suppression of Tumor-forming Ability and Related Traits in MCF-7 Human Breast Cancer Cells by Fusion with Immortal Mammary Epithelial Cells", *Proc. Natl. Acad. Sci (USA)*, 87:2314-2318 (1990), the disclosure of which is herein incorporated by reference in its entirety. The hybrids has among other traits of their normal parent cells, the ability to increase the expression of the angiogenesis inhibitor thrombospondin.

A "switch" to the angiogenic phenotype by fibroblasts cultured from Li-Fraumeni patients coincides with loss of the wild-type allele of the p53 tumor suppressor gene and reduced expression of thrombospondin-1. A novel angiogenesis inhibitor, "angiostatin" is released by the primary tumor mass of a Lewis lung carcinoma. When the primary tumor is present, metastatic tumor growth is suppressed by "angiostatin"; but, after primary tumor removal, the metastases neovascularize and grow. The "angiostatin" activity co-purifies with a 38 kDa plasminogen fragment, as disclosed in O'REILLY et al., "Angiostatin: A Novel Angiogenesis Inhibitor that Mediates the Suppression of Metastases by a Lewis Lung Carcinoma", *Cell*, 79:315-328 (1994), the disclosure of which is herein incorporated by reference in its entirety. Similarly, endostatin a 20 kDa C-terminal fragment of collagen XVIII prevents the angiogenic switch in pre-malignant lesions, intervening in the rapid expansion of small tumors, or inducing the regression of a large end-stage cancers, as disclosed in O'REILLY et al. (1994), cited above; and BERGERS et al., "Effects of Angiogenesis Inhibitors on Multistage Carcinogenesis in Mice", *Science*, 284:808-812 (1999), the disclosures of which are herein incorporated by reference in their entireties. Other negative regulators of endothelial proliferation include: platelet factor 4, tissue inhibitors of metalloproteinases, a 16 kDa fragment of prolactin, bFGF/FGF-2 soluble receptor, and TGFβ, as disclosed in FOLKMAN (1995), cited above, the disclosure of which is herein incorporated by reference in its entirety.

Many asparagine-linked glycoproteins such as selectins, VEGFs, integrins and their receptors have been claimed to be involved during angiogenesis. Several directly angiogenic and relatively specific growth factors have been isolated: Vascular endothelial growth factor A (VEGF-A), VEGF-B, VEGF-C and placental growth factor (PlGF) are among the best characterized. These glycoproteins display high amino acid similarity in the platelet-derived growth factor (PDGF) domain. Another class of angiogenic polypeptides includes molecules with a broad range of target cells activating either a complete (migration and proliferation) or incomplete (only migration) angiogenic process in vitro.

Vascular endothelial growth factor (VEGF) induces angiogenesis, as disclosed in KIM et al., "Inhibition of Vascular Endothelial Growth Factor-induced Angiogenesis Suppresses Tumor Growth in vivo", *Nature*, 362:841-844 (1993), the disclosure of which is herein incorporated by reference in its entirety. Treatment of mice previously injected with human rhabdomyosarcoma, glioblastoma multiforme, or leiomyosarcoma cell lines with a monoclonal antibody specific for VEGF has decreased the density of tumor vessels, and inhibited the tumor growth. The antibody however, has no effect on the growth rate of tumor cells in vitro. Infection of tumor endothelial cells in vivo with a retrovirus construct encoding a dominant-negative, non-functional mutant VEGF receptor (flk-1) also markedly has suppressed the tumor growth, MILLAUER et al., "Glioblastoma Growth Inhibited in vivo by a Dominant-negative Flk-1 Mutant", *Nature*, 367:576-579 (1994), the disclosure of which is herein incorporated by reference in its entirety.

Regarding integrins and their receptors, stimulation of some types of integrin receptors leads to angiogenesis. There are two distinct pathways that induce angiogenesis mediated by different types of integrins of the vitronectin receptor family, $\alpha_v\beta$ integrins: (1) one pathway is triggered by basic fibroblast growth factor (bFGF/FGF-2) and tumor necrosis factor $\alpha$ (TNF $\alpha$), and requires interaction with integrins $\alpha_v\beta_3$; and (2) the other is via VEGF-A and is integrin $\alpha_v\beta_5$-dependent, as discussed in FRIEDLANDER et al. (1995), cited above; and BROOKS et al., "Requirement of Vascular Integrin $\alpha v\beta 3$ for Angiogenesis", *Science*, 264: 569-571 (1994), the disclosures of which are herein incorporated by reference in their entireties.

Recent reports indicate that induction of angiogenesis by tumor or cytokine promotes vascular cell entry into the cell cycle and expression of $\alpha_v\beta_3$ integrin. It has also suggested that a single intra-vascular injection of antagonists of $\alpha_v\beta_3$ integrin (i.e., either a cyclic peptide or monoclonal antibody) disrupts ongoing angiogenesis on the chicken chorioallantoic membrane (CAM). Integrin antagonists induce apoptosis (i.e., programmed cell death) of the proliferative angiogenic vascular cells leaving preexisting quiescent blood vessels unaffected, as disclosed in BROOKS et al., "Integrin $\alpha v\beta 3$ Antagonists Promote Tumor Regression by Inducing Apoptosis of Angiogenic Blood Vessels", *Cell*, 79:1157-1164 (1994), the disclosure of which is herein incorporated by reference in its entirety.

It is also becoming evident that there are different classes of endogenous inhibitors of endothelial cell growth and motility that work in concert with inducer molecules to control angiogenesis. Reducing the concentration of inhibitor or increasing that of inducer results in an angiogenic switch, as discussed in HANAHAN et al., "Patterns and Emerging Mechanisms of the Angiogenic Switch During Tumorigenesis", *Cell*, 86:353-364 (1996), the disclosure of which is herein incorporated by reference in its entirety.

Processing of glycan chains to a "high-mannose" type or to a "complex" type has also been mentioned as being relevant to endothelial cell proliferation and differentiation, as disclosed in NGUYEN et al., "1-Deoxymannojirimycin Inhibits Capillary Tube Formation in vitro, Analysis of N-linked Oligosaccharides in Bovine Capillary Endothelial Cells", *J. Biol. Chem.*, 267:26157-26165 (1992); and PILI et al., "The α-glucosidase I Inhibitor Castanospermine Alters Endothelial Cell Glycosylation, Prevents Angiogenesis, and Inhibits Tumor Growth", *Cancer Res.*, 55:2920-2926 (1995), the disclosures of which are herein incorporated by reference in their entireties. It has been suggested across the cell types that N-linked glycoproteins are important determinants of a number of cellular functions including endothelial cell proliferation, as discussed in BANERJEE (1988), cited above; BANERJEE et al., "Is Asparagine-Linked Protein Glycosylation an Obligatory Requirement for Angiogenesis?", *Indian J. Biochem. Biophys.*, 30:389-394 (1993); NGUYEN et al. (1992), cited above; NGUYEN et al., "A Role of Sialyl Lewis-X/A Glycoconjugates in Capillary Morphogenesis", *Nature*, 365:267-269 (1993); and PILI et al. (1995), cited above, the disclosures of which are herein incorporated by reference in their entireties.

NGUYEN et al. (1992), cited above, the disclosure of which is herein incorporated by reference in its entirety, discloses that 1-deoxymannonojirimycin, an N-glycan processing inhibitor, inhibits "hybrid" and "complex" type oligosaccharides to block capillary tube formation and tumor growth. The structure of 1-deoxymannonojirimycin is disclosed on page 516 of ELBEIN, "Inhibitors of the Biosynthesis and Processing of N-linked Oligosaccharide Chains", *Ann. Rev. Biochem.*, 56:497-534 (1987), the disclosure of which is herein incorporated by reference in its entirety.

PILI et al. (1995), cited above, the disclosure of which is herein incorporated by reference in its entirety, discloses that castanospermine, an N-glycan processing inhibitor, inhibits "hybrid" and "complex" type oligosaccharides to block capillary tube formation and tumor growth. The structure of castanospermine is disclosed on page 516 of ELBEIN (1987), cited above, the disclosure of which is herein incorporated by reference in its entirety.

Studies have claimed that tunicamycin, a specific inhibitor of N-linked protein glycosylation has profound effects on the surface morphology, ultrastructure, and functional properties of a primary culture of bovine aortic endothelial cells and endothelial cell monolayers, as discussed in TIGANIS et al., "Functional and Morphological Changes Induced by Tunicamycin in Dividing and Confluent Endothelial Cells", *Exp. Cell Res.*, 198:191-200 (1992), the disclosure of which is herein incorporated by reference in its entirety. TIGANIS et al. involves an examination of the effect of tunicamycin on dividing and confluent cells. TIGANIS et al. discloses that since a feature of tunicamycin toxicity in animals is impaired permeability of brain microvessels, an important question is whether tunicamycin has a direct effect on microvessels in vivo and if so whether glycoprotein components of the tight junctions (zonula occludens) are specifically altered. The study in TIGANIS et al. involves bovine aortic cells and the endothelial lining of blood vessels.

Glycoproteins need continuous expression of $Glc_3Man_9GlcNAc_2$-PP-Dol as a pre-requisite for their structural modification. In the dolichol pathway during formation of $Glc_3Man_9GlcNAc_2$-PP-Dol, the enzyme, Dol-P-Man synthase, is an essential intermediate in the elongation of $Man_5GlcNAc_2$-PP-Dol to $Man_9GlcNAc_2$-PP-Dol, and an allosteric activator of GlcNAc-1-phosphate transferase, as disclosed in CHAPMAN et al., "Structure of the Lipid-linked Oligosaccharides that Accumulate in Class B thy-1-negative Mutant Lymphomas", *Cell*, 17:509-515 (1979); BANERJEE et al., "Amphomycin: Effect of the Lipopeptide Antibiotic on the Glycosylation and Extraction of Dolichyl Monophosphate in Calf Brain Membranes", *Biochemistry*, 20:1561-1568 (1981); and KEAN, "Site of Stimulation by Mannosyl-P-dolichol of GlcNAc-lipid Formation by Microsomes of Embryonic Chick Retina", *Glycoconjugate J.*, 13:675-680 (1996), the disclosures of which are herein incorporated by reference in their entireties.

As discussed in more detail below, involvement of the dolichol-linked glycan chain in capillary endothelial cell proliferation has been documented in studies on environmental insult due to $CO_2$ depletion, and tying up the available dolichylmonophosphate (Dol-P) with amphomycin, as discussed in BANERJEE (1988), cited above; BANERJEE, "Amphomycin Inhibits Mannosylphosphoryldolichol Synthesis by Forming a Complex with Dolichylmonophosphate", *J. Biol. Chem.*, 264:2024-2028 (1989); and BANERJEE, "A Recent Approach to the Study of Dolichyl Monophosphate Topology in the Rough Endoplasmic Reticulum", *Acta Biochimica Polonica*, 41:275-280 (1994), the disclosures of which are herein incorporated by reference in their entireties.

Regarding the relationship between the dolichol-pathway and the growth and proliferation of the capillary endothelial cells, it is noted that during somatic cell division or under the influence of angiogenic stimulus, the cell duplicates essentially all its contents including the available asparagine-linked glycoproteins. To give a few examples, many inducers of angiogenesis such as VEGF, bFGF/FGF-2, PlGF, vascular cell adhesion molecule-1, soluble E-selectin, fibronectin, laminin, thrombospondin and many of their receptors, e.g., integrins, sialyl Lewis X as well as the capillary endothelial cell marker Factor VIII:C are asparagine-linked glycoproteins and carry N-glycan chains as a part of their structures. Building of $Glc_3Man_9GlcNAc_2$-PP-Dol oligosaccharide chain on the dolichol backbone through a pyrophosphate bridge in the ER membrane is a prerequisite for the asparagine residues present in the consensus sequence Asn-X-Ser/Thr to be N-glycosylated. To address a cooperation between the protein N-glycosylation pathway and the endothelial cell growth and proliferation, cells have been (1) placed under environmental stress by $CO_2$ depletion; (2) treated with amphomycin; and (3) stimulated with a β-agonist, isoproterenol, obtaining the following results:

Regarding $CO_2$ depletion, N-glycosylation of proteins is increased nearly 3.5-fold, and the $K_m$ for Dol-P-Man synthase is decreased by ~50% when capillary endothelial cells (an established cell line from the microvasculature of bovine adrenal medulla) were cultured in the absence of $CO_2$, as disclosed in BANERJEE et al., "Endothelial Cells from Bovine Adrenal Medulla Develop Capillary-like Growth Patterns in Culture", Proc. Natl. Acad. Sci. USA, 82:4702-4706 (1985); BANERJEE et al., "Microvascular Endothelial Cells from Bovine Adrenal Medulla—A Model for in vitro Angiogenesis", Angiogenesis: Models, Modulators and Clinical Applications, pp. 7-18 (1998); and BANERJEE (1998), cited above, the disclosures of which are herein incorporated by reference in their entireties.

Using a non-transformed capillary endothelial cell line from bovine adrenal medulla, cells were cultured in air (i.e., the absence of 5% (v/v) $CO_2$) and showed decreased cell adhesion, did not proliferate, and died within 24 hours of culturing, as disclosed in BANERJEE (1988), cited above, the disclosure of which is herein incorporated by reference in its entirety. Interestingly, supplementation of media with 10 mM Hepes-$NaHCO_3$, pH 7.4, improved the cell attachment as disclosed in BANERJEE (1988), cited above, the disclosure of which is herein incorporated by reference in its entirety. It has also been shown that under these experimental conditions protein glycosylation was also increased by 4.3-fold, as discussed in BANERJEE (1988), cited above, the disclosure of which is herein incorporated by reference in its entirety. Analysis of Dol-P-Man synthase, a "key" glycosyltransferase in the Dol-P pathway, as discussed in KORNFELD et al., "Assembly of Asparagine-Linked Oligosaccharides", Annu Rev Biochem, 54:631-664 (1985), the disclosure of which is herein incorporated by reference in its entirety, suggested that the $K_m$ for GDP-mannose was reduced by ~32% in $CO_2$-deprived cells without a significant change in the $V_{max}$, but the ratio of [$^3$H]-mannose to [$^{14}$C]-leucine (a protein N-glycosylation index) was increased to 4.3, compared to those cultured normally, as discussed in BANERJEE (1988), cited above, the disclosure of which is herein incorporated by reference in its entirety.

As to treatment with amphomycin, studies with amphomycin indicated that inhibition of $Glc_3Man_9GlcNAc_2$-PP-Dol (OSL) biosynthesis inhibited the endothelial cell proliferation, as disclosed in BANERJEE et al. (1993), cited above, the disclosure of which is herein incorporated by reference in its entirety. Amphomycin is an undecapeptide from Streptomyces canus whose N-terminus is blocked due to a fatty acid substitution, as disclosed in HEINEMANN et al., "Amphomycin, a New Antibiotic", Antibiot. Chemother., 3:1239-1242 (1953); and BODANSZKY et al., "Structure of the Peptide Antibiotic Amphomycin", J. Am. Chem. Soc., 95:2352-2357 (1973), the disclosures of which are herein incorporated by reference in their entireties. Amphomycin inhibits endothelial cell proliferation in a dose-dependent manner, as discussed in BANERJEE et al. (1993), cited above, the disclosure of which is herein incorporated by reference in its entirety. The binding of amphomycin to Dol-P in the presence of $Ca^{2+}$ blocks OSL assembly by interfering with the synthesis of Dol-PP-GlcNAc, Dol-P-Man, and Dol-P-Glc, respectively, as disclosed in BANERJEE (1989), cited above; BANERJEE, "A Recent Approach to the Study of Dolichyl Monophosphate Topology in the Rough Endoplasmic Reticulum", Acta Biochimica Polonica, 41:275-280 (1994); BANERJEE, "Amphomycin: A Tool to Study Protein N-glycosylation", J. Biosci., 11:311-319 (1987); and BANERJEE et al., "Monoclonal Antibody to Amphomycin. A Tool to Study the Topography of Dolichol Monophosphate in the Membrane", Carbohyd. Res., 236:301-313 (1992), the disclosures of which are herein incorporated by reference in their entireties. Thus, amphomycin is a lipopeptide which binds to Dol-P in a $Ca^{2+}$-dependent manner and inhibits the synthesis of Dol-P-Man, Dol-P-Glc and Dol-PP-GlcNAc and consequently $Glc_3Man_9GlcNAc_2$-PP-Dol, as discussed in BANERJEE, "Amphomycin Inhibits Mannosylphosphoryldolichol Synthesis by Forming a Complex with Dolichylmonophosphate", J. Biol. Chem., 264:2024-2028 (1989); and BANERJEE et al. (1981), cited above, the disclosures of which are herein incorporated by reference in their entireties.

In view of the above, the observations of (1) lowering of $K_m$ for GDP-mannose for Dol-P-Man synthase activity in the ER membranes in cells grown in the absence of environmental $CO_2$ but supplemented with 100 mM Hepes-$HCO_3$ buffer, pH 7.4, as discussed in BANERJEE (1988), cited above, the disclosure of which is herein incorporated by reference in its entirety; and (2) retardation of cellular proliferation in the presence of amphomycin, as discussed in BANERJEE et al. (1993), cited above, the disclosure of which is herein incorporated by reference in its entirety, establish that $Glc_3Man_9GlcNAc_2$-PP-Dol (OSL) is essential for normal growth and proliferation of capillary endothelial cells.

Regarding treatment with isoproterenol, it was proposed that stimulating eukaryotic cells with a β-agonist, isoproterenol, increased protein N-glycosylation by activating the dolichol-pathway, as disclosed in BANERJEE, "cAMP-Mediated Protein Phosphorylation of Microsomal Membranes Increases Mannosylphosphodolichol Synthase Activity", Proc Natl Acad Sci (USA), 84:6389-6393 (1987), the disclosure of which is herein incorporated by reference in its entirety. Addition of either isoproterenol, or cholera toxin, or prostaglandin $E_1$, or 8Br-cAMP in the media enhanced the capillary endothelial cell proliferation by reducing the cell doubling time by 20-55 hours. cAMP did not change the cell morphology but accelerated lumen formation, as disclosed in ELIAS et al., "Direct Arterial Vascularization of Estrogen-Induced Prolactin Secreting Anterior Pituitary Tumors", Proc Natl Acad Sci (USA), 81:4549-4553 (1984); and DAS et al., "β-adrenoreceptors of Multiple Affinities in a Clonal Capillary Endothelial Cell Line and its Functional Implication", Mol. Cell. Biochem., 140:49-54 (1994), the disclosures of which are herein incorporated by reference in their entireties. Pre-treatment of cells with either $β_1$-antagonist, atenolol, or a $β_2$-antagonist, ICI-118,551, reduced protein N-glycosylation substantially. Increased protein N-glycosylation was not due to an increase in the Dol-P pool but due to an activation of Dol-P-Man synthase by cAMP-dependent protein kinase (PKA) mediated protein phosphorylation event. This activation process of Dol-P-Man synthase was further confirmed by analyzing the PKA-deficient somatic cell mutants, as disclosed in BANERJEE et al., "Protein Kinase Type I Regulates GDP-mannose:dolichylphosphate-O-β-D-mannosyl Transferase in the ER", *FASEB J*, 9:1361a (1995), the disclosure of which is herein incorporated by reference in its entirety.

BANERJEE et al. (1993), cited above, discloses that tunicamycin, a GlcNAc-1P transferase inhibitor, reduced glycosylation in control cells and in isoproterenol-treated cells. In particular, BANERJEE et al. (1993) discloses that increased protein N-glycosylation by isoproterenol in the presence of exogenous dolichol monophosphate and its reduction by tunicamycin (an inhibitor of GlcNAc-1P transferase) strongly supported the view that the response was mediated through the dolichol pathway and was not due to a simple change in the dolichol monophosphate pool.

In addition, the gene for Dol-P-Man synthase has now been cloned from six different species including *S. cerevisiae*, as disclosed in COLUSSI et al., "Human and *Saccharomyces cerevisiae* Dolichol Phosphate Mannose Synthases Represent Two Class of the Enzyme, but both Function in *Schizosaccharomyces pombe*", *Proc Natl Acad Sci (USA)*, 94: 7873-7878 (1997). It has been shown that Dol-P-Man synthase in *S. cerevisiae* is a structural gene and its mutation is lethal. The Dol-P-Man synthase gene carries a cAMP-dependent protein phosphorylation consensus sequence and its activity is regulated by cAMP-dependent protein kinase-mediated protein phosphorylation signal, as disclosed in ORLEAN et al., "Cloning and Sequencing of the Yeast Gene for Dolichol Phosphate Mannose Synthase, an Essential Proteins", *J. Biol. Chem.*, 263:17499-17507 (1988); MAZHARI-TABRIZI et al, "Cloning and Functional Expression of Glycosyl Transferases from Parasitic Protozoans by Heterologous Complementation in Yeast: the Dolichol Phosphate Mannose Synthase from *Trypanosoma brucei*", *Biochem. J.*, 316:853-858 (1996); ZIMMERMAN et al., "The Isolation of a Dol-P-Man Synthase from *Ustilago maydis* that Functions in *Saceharomyces cerevisiae*", *Yeast*, 12:765-771 (1996); COLUSSI et al. (1997), cited above; BANERJEE et al. (1987), cited above; and BANERJEE, "Regulation of Mannosylphosphoryldolichol Synthase Activity by cAMP-dependent Protein Phosphorylation", *Highlights of Modern Biochemistry, pp.* 379-388 (1989), the disclosures of which are herein incorporated by reference in their entireties. In particular, the sequence data reyealed that the Dol-P-Man synthase gene from all species contains one consensus phosphorylation sequence in an area equivalent to Ser-141 in *S. cerevisiae*.

Using a purified recombinant Dol-P-Man synthase from yeast, it has been shown that in vitro phosphorylation of the Dol-P-Man synthase by the catalytic subunit of PKA activated the Dol-P-Man synthase activity by several fold, as disclosed in BANERJEE et al., "In vitro Phosphorylation of Recombinant Dol-P-Man Synthase from *S. cerevisiea* Enhances its Activity", *FASEB J*, 12:A1363 (1998), the disclosure of which is herein incorporated by reference in its entirety. The increase was due to an increase in $V_{max}$ and not due to an increase in $K_m$ for GDP-mannose. Furthermore, autoradiography of the [$^{32}$P]Dol-P-Man synthase with an anti-DPMS antibody as well as the western blot with an anti-phosphoserine antibody confirmed the phosphorylation of the Dol-P-Man synthase. In a recent study, Ser-141 was replaced with alanine in the dpml gene from *S. cerevisiea* by PCR site-directed mutagenesis with the result being a significant loss of DPMS activity in the protein expressed in *E. coli*, as disclosed in CARRASQUILLO et al., "Serine 141 is Essential for Dol-P-Man Synthase Activity in *S. cereviseia*", *Glycobiology*, 8:93a (1998), the disclosure of which is herein incorporated by reference in its entirety.

The induction of apoptosis by tunicamycin has been found in (1) Chinese hamster ovary (CHO) cell glycosylation mutants Lec9, as discussed in WALKER et al., "A Functional Link Between N-linked Glycosylation and Apoptosis in Chinese Hamster Ovary Cells", *Biochem. Biophys. Res. Commun.*, 250:264-270 (1998), the disclosure of which is herein incorporated by reference in its entirety; (2) SV40-transformed fibroblasts line 90VAVI, as discussed in CARLBERG et al., "Short Exposures to Tunicamycin Induce Apoptosis in SV-40 Transformed but not in Normal Human Fibroblasts", *Carcinogenesis*, 17(12):2589-2596 (1996), the disclosure of which is herein incorporated by reference in its entirety; and (3) sympathetic neurons, as discussed in CHANG et al., "Specific Toxicity of Tunicamycin in Induction of Programmed Cell Death of Sympathetic Neurons", *Exp. Neurol.*, 137(2):210-211 (1996), the disclosure of which is herein incorporated by reference in its entirety. In addition, WALKER et al. (1998), cited above, also suggested that one endogenous signal for triggering apoptosis is due to specific alterations in the N-glycosylation pathway. The Lec9 cell mutants used in WALKER et al. (1998), cited above, exhibit altered N-linked glycan structure, underglycosylation of proteins, ca.40-fold less synthesis of $Glc_3Man_9GlcNAc_2$-PP-Dol and ca.2-fold less synthesis of $Man_5GlcNAc_2$-PP-Dol than parental cells, as discussed in ROSENWALD et al., "Control of Carbohydrate Processing. Increased β1,6-branching in the N-linked Carbohydrates of Lec9 CHO Mutants Appears to Arise from a Defect in Oligosaccharide-dolichol Synthesis", *Mol. Cell. Biol.*, 9:914-924 (1989), the disclosure of which is herein incorporated by reference in its entirety. Therefore, a predisposed condition for apoptosis may exist in Lec9 mutants which upon treatment with 0.2 µg/ml of tunicamycin has been accelerated.

A synthetic analogue of fumagillin, a naturally secreted antibiotic of *Aspergillus fumigatus fresenius* inhibits endothelial cell proliferation in vitro and tumor-induced angiogenesis in vivo, as disclosed in INGBER et al., "Synthetic Analogues of Fuagillin that Inhibit Angiogenesis and Suppress Tumor Growth", *Nature*, 348:555-557 (1990), the disclosure of which is herein incorporated by reference in its entirety, and consequently suppresses the tumor growth. Infusions of basic fibroblast growth factor (bFGF/FGF-2) after implanting a human colon carcinoma cell line in mice not only has increased the tumor size by two-fold but also has caused an increase in the density and branching of tumor blood vessels, GROSS et al., "Modulation of Solid Tumor Grown in vivo by bFGF", *Proc. Am. Assoc. Cancer Res.*, 31:79 (#469) (1990), the disclosure of which is herein incorporated by reference in its entirety. Cells lacking receptors for bFGF/FGF-2 are unresponsive to bFGF/FGF-2 in vitro, and also use of a specific antibody to bFGF/FGF-2 cause ~70% inhibition of growth of a mouse tumor, as disclosed in HORI et al., "Suppression of Solid Tumor Growth by Immunoneutralizing Monoclonal Antibody Against Human Basic Fibroblast Growth Factor", *Cancer Res.*, 51:6180-6184 (1991), the disclosure of which is herein incorporated by reference in its entirety.

Clinically, angiogenesis can be used as a prognostic marker or a therapeutic target for breast cancer. As a prognostic marker, the quantification of angiogenesis has become a useful technique to predict survival, the likelihood of in situ cancer progressing, a tumor response to therapy, and presence of bone marrow micrometastases. Quantification is performed by the mean tumor microvessel density by immunohistochemistry from the most vascular field of the tumor. However, not all studies has shown a correlation between the variables mentioned above. The discrepancy is most probably due to differences in methodology. Due to these limitations, other methods to quantitate angiogenesis have been investigated. Different substances, like angiogenic factors, proteases, and adhesion molecules had been measured in tumors and blood samples from breast cancer patients. These substances include VEGF, FGF-1 & 2, transforming growth factor D1, placental growth factor, TSP, and pleiotrophin. Only VEGF has shown a consistent correlation with relapse.

Furthermore, the following documents discuss angiogenesis. U.S. Pat. No. 5,766,591 to BROOKS et al., the disclosure of which is herein incorporated by reference in its entirety, discloses inhibiting angiogenesis $\alpha_v\beta_3$ antagonists such as polypeptides, monoclonal antibodies, and $\alpha\beta_3$-specific mimetics which have the capacity to interfere with $\alpha_v\beta_3$ function. BROOKS et al. discloses that inhibition of $\alpha_v\beta_3$ results in induction of apoptosis in the neovasculature cells bearing $\alpha_v\beta_3$. BROOKS et al. discloses that cells enter the S and G2/M phase.

U.S. Pat. No. 5,760,028 to JADHAV et al., U.S. Pat. No. 5,760,029 to JADHAV et al., and U.S. Pat. No. 6,130,231 to WITYAK et al., the disclosures of which are herein incorporated by reference in their entireties, disclose several heterocyclic compounds which are $\alpha_v\beta_3$ antagonists which can be used to inhibit angiogenesis.

U.S. Pat. No. 6,096,730 to COLLINS et al. and U.S. Pat. No. 6,160,166 to COLLINS et al., the disclosures of which are herein incorporated by reference in their entireties, disclose phosphonic acid agents which inhibit angiogenesis by inducing programmed cell death (apoptosis) in human microvascular endothelial cells. COLLINS et al. also discloses suramin which arrests cells in S and G2/M phases.

U.S. Pat. No. 6,146,824 to BAR-SHAVIT, the disclosure of which is herein incorporated by reference in its entirety, discloses that a thrombin derived peptide inhibits angiogenesis and induces apoptosis.

U.S. Pat. No. 6,150,407 to TUSÉ et al., the disclosure of which is herein incorporated by reference in its entirety, discloses aromatic compounds which inhibit angiogenesis by mitotic arrest and apoptosis.

YUE et al., "2-Methoxyestradiol, an Endogenous Estrogen Metabolite, Induces Apoptosis in Endothelial Cells and Inhibits Angiogenesis: Possible Role for Stress Activated Protein Kinase Signaling Pathway and Fas Expression", *Molecular Pharmacology*, Vol.51, pp. 951-962 (1997), the disclosure of which is herein incorporated by reference, discloses that 2-methoxyestradiol induces apoptosis in endothelial cells and inhibits angiogenesis.

GUO et al., "Thrombospondin 1 and Type I Repeat Peptides of Thrombospondin 1 Specifically Induce Apoptosis of Endothelial Cells", Cancer Research, 57:1735-1743 (1997), the disclosure of which is herein incorporated by reference in its entirety, discloses that thrombospondin 1 and type I repeat peptides of thrombospondin 1 induce apoptosis of endothelial cells.

U.S. Pat. No. 5,382,514 to PASSANITI et al., the disclosure of which is herein incorporated by reference in its entirety, discloses that IL-1, a peptide, regulates endothelial cell growth via autocrine mechanisms which may lead to programmed cell death (apoptosis).

U.S. Pat. No. 5,994,309 to MAZAR et al., the disclosure of which is herein incorporated by reference, discloses a peptide compound that inhibits angiogenesis, with treated animals having signs of apoptosis.

U.S. Pat. No. 5,854,205 to O'REILLY et al., the disclosure of which is herein incorporated by reference in its entirety, discloses that endostatin protein inhibits angiogenesis.

U.S. Pat. No. 5,837,682 to FOLKMAN et al., U.S. Pat. No. 5,945,403 to FOLKMAN et al., U.S. Pat. No. 6,024,688 to FOLKMAN et al., the disclosures of which are herein incorporated by reference in their entireties, disclose inhibiting angiogenesis with angiostatin fragments which are peptides. Angiostatin is known to arrest cells in G1 phase.

U.S. Pat. No. 6,114,355 to D'AMATO, the disclosure of which is herein incorporated by reference, discloses that thalidomide inhibits angiogenesis. D'AMATO also discloses 2-methoxyestradiol which affects the S phase of cells.

U.S. Pat. No. 5,985,839 to DUPONT et al., the disclosure of which is herein incorporated by reference in its entirety, discloses inhibiting angiogenesis with shark cartilage extracts.

U.S. Pat. No. 5,830,880 to SEDLACEK et al., the disclosure of which is herein incorporated by reference in its entirety, discloses gene therapy for tumors which involves, e.g., DNA for a protein which inhibits angiogenesis.

U.S. Pat. No. 4,670,394 to POLLARD et al., the disclosure of which is herein incorporated by reference, discloses blood clotting Factor VIII:C.

Glycosylation is a means of diversifying a protein without recourse to the genome, and it has the potential to both respond and reflect environmental changes. The endoplasmic reticulum (ER) is one of the largest cell organelles, its membrane constituting over one-half of the total membrane in a cell. The ER lumen, the internal space, comprises over 10% of the cell volume. The vast structure has two essential functions. (1) Proteins destined for transport to other organelles, secretion, or expression on the cell surface are synthesized on the ER surface. During translation, they are translocated into the ER lumen through a pore in the ER membrane. Inside the organelle, they are folded, sometimes with the aid of chaperon proteins, and become glycosylated. A quality control mechanism ensures that only correctly folded proteins exit the ER. Incorrectly folded proteins are retained and ultimately degraded. (2) Synthesis of lipids and cholesterol takes place on the cytoplasmic side of the membrane, as disclosed in O'REILLY et al., "Angiostatin: A Novel Angiogenesis Inhibitor that Mediates the Suppression of Metastases by a Lewis Lung Carcinoma", *Cell*, 79:315-328 (1994); BERGERS et al., "Effects of Angiogenesis Inhibitors on Multistage Carcinogenesis in Mice, *Science*, 284:808-812 (1999); and PAHL, "Signal Transduction from the Endoplasmic Reticulum to the Cell Nucleus", *Physiol. Rev.*, 79:683-701 (1999), the disclosures of which are herein incorporated by reference in their entireties.

Various conditions can interfere with ER function an these are collectively called ER stress. ER stress can arise from a disturbance in protein folding, leading to an accumulation of un-or mis-folded proteins in the organelle. Cells respond to the accumulation of unfolded proteins by increasing the transcription of genes encoding ER resident proteins. The information that the capacity of the ER chaperons has been exceeded originates in the ER lumen and is transmitted to the nucleus by an intracellular signaling pathway, the unfolded protein response (UPR). This signaling pathway utilizes several novel mechanisms, including translational attenuation and a regulated mRNA splicing step, as disclosed in PAHL (1999), cited above; REDDY et al., "Assembly, Sorting and Exit of Oligomeric Proteins from the Endoplasmic Reticulum", *Bio Essays,* 20:546-554 (1998); and CHAPMAN et al., "Intracellular Signaling from the Endoplasmic Reticulum to the Nucleus", *Annu. Rev. Dev. Biol.,* 14:459-485 (1998), the disclosures of which are herein incorporated by reference in their entirety.

Activation of mammalian UPR is characterized in part by increased transcription of at least seven genes encoding ER molecular chaperons. These are Bip/GRP78, as disclosed in LEE, "Mammalian Stress Response: Induction of the Glucose-regulated Protein Family", *Curr. Opin. Cell Biol.,* 4:267-273 (1992), the disclosure of which is herein incorporated by reference in its entirety, as well as induction of C/EBP homologous protein (CHOP), a transcription factor also known as growth arrest and DNA damage gene product-153 or GADD153, as disclosed in WANG et al., "Signals from the Stressed Endoplasmic Reticulum Induce C/EBP-homologous Protein (CHOP/GADD153)", *Mol. Cell. Biol.,* 16:4273-4280 (1996); and WANG et al., "Cloning of Mammalian Ire1 Reveals Diversity in the ER Stress Responses", *EMBO J.,* 17:5708-5717 (1998), the disclosures of which are herein incorporated by reference in their entireties. Three ER transmembrane signaling proteins that are thought to be the proximal effectors of the UPR are Ern1 and 2, PERK, as disclosed in WANG et al., "Cloning of Mammalian Ire1 Reveals Diversity in the ER Stress Responses", *EMBO J.,* 17:5708-5717 (1988); TIRASOPHON et al., "A Stress Response Pathway from the Endoplasmic Reticulum to the Nucleus Requires a Novel Bifunctional Protein Kinase/Endoribonuclease (Ire1p) in Mammalian Cells", *Genes Dev.,* 12:1812-1824 (1998); and HARDING et al., "Protein Translation and Folding are Coupled by an Endoplasmic-reticulum-resident Kinase", *Nature,* 397:271-274 (1999), the disclosures of which are herein incorporated by reference in their entireties.

In principle, the mechanism underlying UPR-induced ER-stress condition could indirectly impede cell-cycle progression by interfering with the proper maturation of growth factor receptors or other modulators of mitogenic signaling, as disclosed in CAI et al., "Down-Regulation of Epidermal Growth Factor Receptor-Signaling Pathway by Binding of GRP78/BiP to the Receptor Under Glucose-Starved Stress Conditions", *Journal of Cellular Physiology,* 177:282-288 (1998), the disclosure of which is herein incorporated by reference in its entirety. Alternatively, ER stress may directly induce checkpoint response that prevents cells from completing their cell division cycle under conditions that compromise the proper folding and assembly of proteins response, as disclosed in BREWER et al., "Mammalian Unfolded Protein Response Inhibits Cyclin D1 Translation and Cell-cycle Progression", *Proc. Natl. Acad. Sci (USA),* 96:8505-8610 (1999); and NAKAGAWA et al., "Caspase-12 Mediates Endoplasmic-reticulum-Specific Apoptosis and Cytotoxicity by Amyloid-β", *Nature,* 403:98-103 (2000), the disclosures of which are herein incorporated by reference in their entireties. Since the late 1970s there has been a clear link between sugar metabolism and the UPR, as disclosed in POUYSSEGUR et al., "Induction of Two Transformation-sensitive Membrane Polypeptides in Normal Fibroblasts by a Block in Glycoprotein Synthesis or Glucose Deprivation", *Cell,* 11:941-947 (1977); SHIU et al., "Glucose Depletion Accounts for the Induction of Two Transformation-sensitive Membrane Proteins in Rous Sarcoma Virus-transformed Chick Embryo Fibroblasts", *Proc. Natl. Acad. Sci. (USA)* 74:3840-3844 (1977); and PELUSO et al., "Infection with Paramyxoviruses Stimulates Synthesis of Cellular Polypeptides that are also Stimulated in Cells Transformed by Rous Sarcoma Virus or Deprived of Glucose", *Proc. Natl. Acad. Sci. (USA),* 75:6120-6124 (1978); GETHING et al., "Protein Folding in the Cell", *Nature,* 355:33-45 (1992); PAHL et al., "A Novel Signal Transduction Pathway from the Endoplasmic Reticulum to the Nucleus is Mediated by Transcription Factor NF-kappa B", *EMBO J.,* 14:2580-2588 (1995); and WATOWICH et al., "Complex Regulation of Heat Shock- and Glucose-responsive Genes in Human Cells", *Mol Cell Biol.,* 8:393-405 (1988), the disclosures of which are herein incorporated by reference in their entireties.

The parallel advances in the mechanisms of angiogenesis have produced a plethora of target molecules and corresponding potential drugs. There are two recognized approaches to target the angiogenesis process in the clinic: vascular targeting and anti-angiogenesis. These approaches are complementary. The first, attacks the endothelial cells directly, inducing either necrosis or apoptosis. The effect is immediate. The latter affects the growth of new vessels. The different mechanisms of vascular targeting and anti-angiogenesis suggest that they may be used synergistically in the future. For small micrometastases without established vasculature, inhibition of new vessels formation will be a major target. On the other hand, larger metastases with established vessels would be effectively managed by vascular destruction initially, followed by preventing regrowth of vessels by anti-angiogenic factors. Anti-angiogenic agents have shown to demonstrate synergy with radiotherapy and many conventional anti-cancer drugs, including tamoxifen.

Irrespective of the significant progress made in recent years in the understanding of the development of the vasculature, and discovering and/or better characterizing many factors critical to vascular development and regulation, very little is known about the molecular events that trigger the withdrawal of the endothelial cell from the cell-cycle, that subsequently regulate their differentiation to form new vessels, or that finally switch off the process. It is, however, increasingly becoming clear that it is not the number of vessels, but their biological properties that determine the progress of a solid tumor.

SUMMARY OF THE INVENTION

The present invention is directed to methods of inhibiting angiogenesis, i.e., the growth of capillary endothelial cells which form new blood microvessels. As a result, the present invention is directed methods of treating disease states, e.g., tumors such as malignant and benign tumors, characterized by an abnormally high amount of angiogenesis.

In one aspect, the present invention is directed to a method for inhibiting angiogenesis, comprising: administering a nucleoside in an amount effective to inhibit angiogenesis, to a patient in need of such treatment.

In another aspect, the present invention is directed to a method for inhibiting angiogenesis, comprising: administering a nucleoside, which comprises glucosamine, in an amount effective to inhibit angiogenesis, to a patient in need of such treatment; wherein the nucleoside is administered for a period of time, subsequently the administration of the nucleoside is suspended for a period of time of at least about 1 week, and subsequently the administration of the nucleoside is resumed.

In still another aspect, the present invention is directed to a method for inhibiting angiogenesis, comprising: administering a nucleoside in an amount effective to inhibit angio genesis, to a patient in need of such treatment; wherein the nucleoside is represented by the following formula (I):

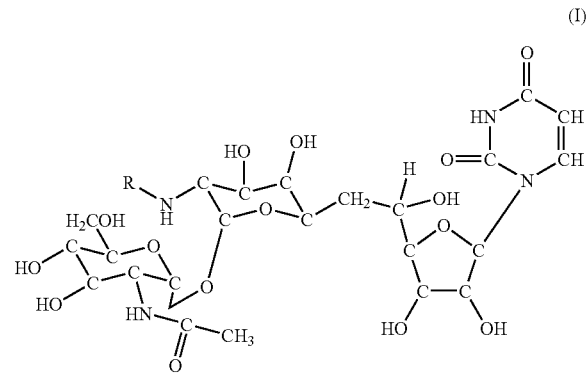

(I)

where R may be:

$(CH_3)_2$—CH—$(CH_2)_n$—CH=CH—(CO)—
  where: n maybe 1-12
    α β unsaturated may be trans or cis;

$CH_3$—$(CH_2)_w$—CH=CH—(CO)—
  where: w maybe 1-12
    α β unsaturated may be trans or cis;

$C_xH_{2x+1}$—CH=CH—(CO)—
  where: x may be 1-30
    α β unsaturated may be trans or cis;

$(CH_3)_2$—CH—$(CH_2)_y$—(CO)—
  where: y may be 1-12
    α β unsaturated may be trans or cis; or $CH_3$—$(CH_2)_z$—(CO)—
  where: z may be 1-12
    α β unsaturated may be trans or cis;

wherein the nucleoside is administered for a period of time, subsequently the administration of the nucleoside is suspended for a period of time of at least about 1 week, and subsequently the administration of the nucleoside is resumed.

In yet another aspect, the present invention is directed to a method for inhibiting angiogenesis, comprising: administering tunicamycin in an amount effective to inhibit angiogenesis, to a patient in need of such treatment; wherein the tunicamycin is administered for a period of about 1 week to 6 months at a daily dosage of about 5 to 20 mg/kg of body weight, subsequently the administration of the tunicamycin is suspended for a period of about 1 week to 6 months, and subsequently the tunicamycin is administered for a period of about 1 week to 6 months at a daily dosage of about 5 to 20 mg/kg of body weight.

In another aspect, the present invention is directed to a method for inhibiting angiogenesis, comprising: administering an N-glycosylation inhibitor, which is not amphomycin, in an amount effective to inhibit angiogenesis, to a patient in need of such treatment.

In a further aspect, the present invention is directed to a method for inhibiting angiogenesis, comprising: administering an agent which induces ER stress in capillary endothelial cells in an amount effective to inhibit angiogenesis, to a patient in need of such treatment.

In another aspect, the present invention is directed to a method for inhibiting angiogenesis, comprising: administering an agent, which induces unfolded protein response, in an amount effective to inhibit angiogenesis, to a patient in need of such treatment.

In yet another aspect, the present invention is directed to a method for inhibiting angiogenesis, comprising: administering an agent which inhibits the dolichol pathway in an amount effective to inhibit angiogenesis, to a patient in need of such treatment, wherein the agent is not amphomycin.

In still another aspect, the present invention is directed to a method for inhibiting angiogenesis, comprising: administering a $Glc_3Man_9GlcNAc_2$-PP-Dol biosynthesis inhibitor, which is not amphomycin, in an amount effective to inhibit angiogenesis, to a patient in need of such treatment.

In a further aspect, the present invention is directed to a method for inhibiting angiogenesis, comprising: administering GlcNAc-1P transferase inhibitor in an amount effective to inhibit angiogenesis, to a patient in need of such treatment.

In still another aspect, the present invention is directed to a method for inhibiting angiogenesis, comprising: administering an agent which reduces Dol-P-Man synthase activity in vivo in an amount effective to inhibit angiogenesis, to a patient in need of such treatment.

In yet another aspect, the present invention is directed to a method for inhibiting angiogenesis, comprising: administering a non-peptide, which arrests the cell cycle of capillary endothelial cells in G1 phase, in an amount effective to inhibit angiogenesis, to a patient in need of such treatment.

In still another aspect, the present invention is directed to a method for inhibiting angiogenesis, comprising: administering a non-peptide, which induces apoptosis in capillary endothelial cells, in an amount effective to inhibit angiogenesis, to a patient in need of such treatment.

In another aspect, the present invention is directed to a method for inhibiting angiogenesis, comprising: inducing accumulation of immunopositive Factor VIII:C in capillary endothelial cells to inhibit angiogenesis in a patient in need of such treatment.

In a further aspect, the present invention is directed to a method for inhibiting angiogenesis, comprising: administering an agent, which inhibits the dolichol pathway, in an amount effective to inhibit angiogenesis, to a patient in need of such treatment, wherein the agent is cell permeable.

In another aspect, the present invention is directed to a method for inhibiting angiogenesis, comprising: administering a $Glc_3Man_9GlcNAc_2$-PP-Dol biosynthesis inhibitor, which is cell permeable, in an amount effective to inhibit angiogenesis, to a patient in need of such treatment.

In still another aspect, the present invention is directed to a method for inhibiting angiogenesis, comprising: administering an agent which is cell permeable in an amount effective to inhibit angiogenesis, to a patient in need of such treatment to induce apoptosis in capillary endothelial cells.

In still another aspect, the present invention is directed to a method for inhibiting angiogenesis, comprising: administering a cell permeable agent in an amount effective to inhibit angiogenesis, to a patient in need of such treatment to reduce intratumoral microvascular density.

In one aspect, the nucleoside comprises glucosamine.

In another aspect, the nucleoside comprises N-acetylated glucosamine.

In still another aspect, the nucleoside comprises a pyrimidine nucleoside.

In yet another aspect, the agent comprises at least one of tunicamycin and functional derivatives thereof.

In a further aspect, the agent comprises at least one of tunicamycin homologues $A_1, A_2, B_1, B_2, C_1, C_2, D_1,$ and $D_2$.

In another aspect, the agent is administered for a period of time, subsequently the administration of the agent is suspended for a period of time of at least about 1 week, and subsequently the administration of the agent is resumed.

In yet another aspect, the agent is administered for a period of about 1 week to 6 months.

In another aspect, the agent is administered for a period of about 1 week to 6 months, subsequently the administration of the agent is suspended for a period of about 1 week to 1 year, and subsequently the agent is administered for a period of about 1 week to 6 months.

In yet another aspect, the agent is administered daily in a dosage of about 5 to 20 mg/kg of body weight.

In still another aspect, the agent is administered for a period of about 1 week to 6 months at a daily dosage of about 5 to 20 mg/kg of body weight, subsequently the administration of the agent is suspended for a period of about 1 week to 6 months, and subsequently the agent is administered for a period of about 1 week to 6 months at a daily dosage of about 5 to 20 mg/kg of body weight.

In yet another aspect, the patient in need of such treatment has at least one of diabetic retinopathy, atherosclerotic plaques, scleroderma, hypertrophic scarring, vascular adhesions, angiofibroma, trachoma and corneal graft neovascularization, neovascular glaucoma, thrombosis, restenosis, osteoporosis, macular degeneration, arthritis, hemangiomas, psoriasis, and a tumor.

In another aspect, the agent is cell permeable.

In still another aspect, the agent is freely diffusible into cells.

BRIEF DESCRIPTION OF THE DRAWINGS

The present invention is further described in the detailed description which follows, in reference to the noted plurality of non-limiting drawings, wherein:

FIG. 1A shows 4 days in culture at 2% (v/v) heat-inactivated fetal bovine serum (×1,700; –10 μm). FIG. 1B shows 4 days in culture at 10% (v/v) heat-inactivated fetal bovine serum (×700; –10 μm). FIG. 1C shows 7 days in culture at 2% (v/v) heat-inactivated fetal bovine serum (×1,100; –10 μm). FIG. 1D shows 4 days in culture at 2% (v/v) heat-inactivated fetal bovine serum (×1,700; –10 μm). FIG. 1E shows 4 days in culture at 2% (v/v) heat-inactivated fetal bovine serum containing 1 μg/ml tunicamycin (×1,700; –10 μm).

FIGS. 2A-2B show the effect of tunicamycin on the induction of apoptosis. Cells were treated with 1 μg/ml of tunicamycin for 32 hours in minimal essential medium with Earle's salt (EMEM) containing 2% (v/v) heat-inactivated fetal bovine serum. FIG. 2A shows DNA laddering; M=50 bp ladder, T=tunicamycin, C=control. FIG. 2B shows flow cytometry; A=apoptosis; M1 ≈G1, M2≈S, M3≈G2/M.

FIGS. 3A-3B show the recovery of endothelial cells after treatment with tunicamycin. FIG. 3A shows 48 hour exposure. FIG. 3B shows 72 hours exposure FIGS. 4A-4B are pie charts depicting the distribution of the tunicamycin sensitive cell clone in G1, S and G2+M phases during proliferation in EMEM containing 2% (v/v) heat-inactivated fetal bovine serum. FIG. 4A shows the parental line BAMEC. FIG. 4B shows the tunicamycin sensitive clone JMEC.

FIGS. 6A-6B show the effect of heat-inactivated fetal bovine serum and bFGF/FGF-2 on proliferation of capillary endothelial cells. Cells were synchronized as described in the Examples. FIG. 6A shows cells that were exposed to 1% (v/v) (●), 2% (v/v) (■), or 10% (v/v) (▲) heat-inactivated fetal bovine serum in EMEM and cultured at 37° C. in the presence of 5% (v/v) $CO_2$/95% (v/v) air. Cells were removed after every 8 hours, trypsinized, and counted in a hemacytometer. It was monitored for 5 days. Each point represents the mean±SEM from six determinations (n=6). FIG. 6B shows cells that were exposed to bFGF/FGF-2 1 ng/ml (●), 10 ng/ml (▲), 100 ng/ml (♦) and processed in the same manner as the cells of FIG. 6A. Medium with 2% (v/v) heat-inactivated fetal bovine serum (■) as a control. Each point represents the mean±SEM from three determinations (n=3).

FIGS. 7A-7F show light microscopy of capillary endothelial cells cultured for different lengths of time. Cells were synchronized as described in the Examples and cultured in 2% (v/v) (FIGS. 7A-7C), or 10% (v/v) (FIGS. 7D-7F) heat-inactivated fetal bovine serum in EMEM. FIG. 7A shows day 0 (synchronized culture), FIG. 7B shows day 3, FIG. 7C shows day 5; FIG. 7D shows day 3, FIG. 7E day 5, and FIG. 7F shows day 10. Cells were photographed in a Nikon Alphashot inverted microscope with a magnification of 140×.

FIGS. 9A-9C show scanning electron microscopy of capillary endothelial cells cultured for different lengths of time. Synchronized cultures in Thermanox coverslips were placed in 2% or 10% (v/v) heat-inactivated fetal bovine serum containing EMEM. Cells were withdrawn at different times and processed for microscopy as described in the Examples. FIG. 9A shows 4 days in culture at 2% (v/v) heat-inactivated fetal bovine serum (–10 μm; magnification 1,700×), FIG. 9B shows 4 days in culture at 10% (v/v) heat-inactivated fetal bovine serum (–10 μm; magnification 700×), FIG. 9C shows 7 days in culture at 2% (v/v) heat-inactivated fetal bovine serum (–10 μm; magnification 1,100×).

FIG. 10A shows degree of synchronization (0 hour), FIG. 10B shows 32 hours, FIG. 10C shows 40 hours, and FIG. 10D shows 48 hours.

FIG. 11 shows the effect of heat-inactivated fetal bovine serum concentrations on the cell cycle. Synchronized cultures of capillary endothelial cells were grown in 2% (v/v), or 10% (v/v) heat-inactivated fetal bovine serum containing EMEM. FIGS. 11A and 11B show cells that were processed for flow cytometry as mentioned earlier after culturing for 48 hours. FIG. 11A shows cells grown in 2% (v/v) heat-inactivated fetal bovine serum. FIG. 11B shows cells grown in 10% (v/v) heat-inactivated fetal bovine serum. Histograms represents distribution of 2,000 cells. Cell cycle gates were the same as in FIG. 10. FIGS. 11C and 11D are pie charts depicting cells spent in G1, S and G2+M phases during proliferation. FIG. 11C is for cells grown in 2% (v/v) heat-inactivated fetal bovine serum. FIG. 11D is for cells grown in 10% (v/v) heat-inactivated fetal bovine serum.

FIGS. 13A-13H show the effect of tunicamycin on capillary endothelial cell growth and proliferation, and induction of apoptosis. Growth curve: FIG. 13A shows synchronized cultures treated with 1 μg/ml of tunicamycin in a medium containing 2% (v/v) heat-inactivated fetal bovine serum. At different times cells were removed and counted in a hemacytometer. Each determination represents the mean±SEM from six determination (n=6), where (●) tunicamycin, and (■) control. Light microscopy: Synchronized cells were cultured in EMEM with 2% (v/v) heat-inactivated fetal bovine serum alone or 2% (v/v) heat-inactivated fetal bovine serum plus 1 μg/ml of tunicamycin. FIG. 13B shows control, cells were cultured for 48 hours; FIG. 13C shows tunicamycin treated, cells were cultured for 32 hours; FIG. 13D shows tunicamycin treated, cells were cultured for 48 hours. Scanning electron microscopy: FIG. 13E shows control, cells were cultured for 96 hours in 2% (v/v) heat-inactivated fetal bovine serum containing EMEM alone. FIG. 13F shows tunicamycin treated, cells were cultured for 96 hours in the same media containing 1 μg/ml of tunicamycin. Flow cytometry: Synchronized cells were exposed to 1 μg/ml of tunicamycin for 32 hours in EMEM containing 2% (v/v) heat-inactivated fetal bovine serum and analyzed by flow cytometry. Controls had only the vehicle. FIG. 13G shows the histogram from a control culture. FIG. 13H shows the histogram from cells cultured in the presence of 1 μg/ml of tunicamycin. Histograms represent distribution of 3,000 cells. Cell cycle gates were: M1=G0/G1, M2=S, M3=G2+M, and M4=apoptosis.

DETAILED DESCRIPTION OF THE INVENTION

Figure 1:
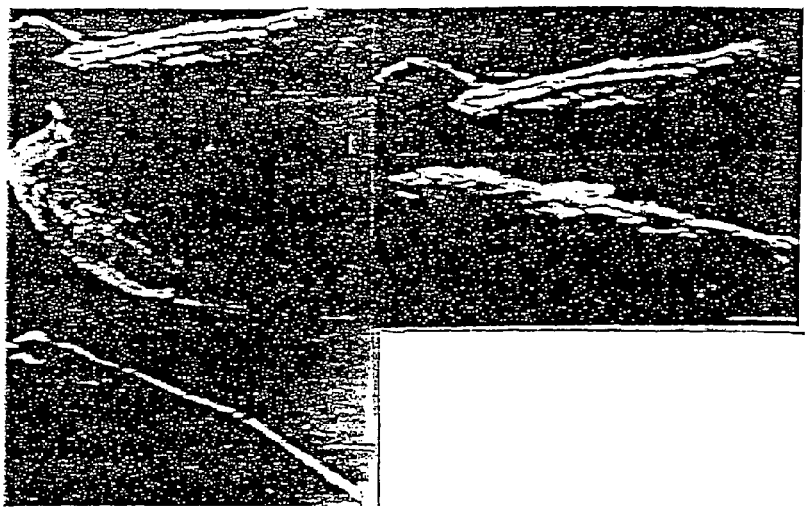
FIGS. 1A-1E show the results from scanning electron microscopy of capillary endothelial cells before and after treatment with tunicamycin.

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description taken with the figures making apparent to those skilled in the art how the several forms of the invention may be embodied in practice.

All percent measurements in this application, unless otherwise stated, are measured by weight based upon 100% of a given sample weight. Thus, for example, 30% represents 30 weight parts out of every 100 weight parts of the sample.

Unless otherwise stated, a reference to a compound or component, includes the compound or component by itself, as well as in combination with other compounds or components, such as mixtures of compounds.

Before further discussion, a definition of the following terms will aid in the understanding of the present invention.

"angiogenesis": growth of capillary endothelial cells to form new blood microvessels "cell permeable": capable of permeating into cells, e.g., by diffusion through cell pores and/or by transporters "freely diffusible into cells": capable of passively diffusing into cells through cell pores "unfolded protein response": intracellular signaling pathway which originates in endoplasmic reticulum (ER) lumen and transmits information to the nucleus, and which is initiated as a result of exceeding the capacity of ER chaperones to transfer unglycosylated glycoproteins to the ER lumen "ER stress": impairment of function of ER "immunopositive Factor VIII:C": epitope for monoclonal antibody (IgG1k) is present. For the present application, to test whether epitope for IgG1k is present, 96-well microtiter EIA plates, available from Corning Inc., Corning, N.Y., are coated overnight at 4° C. with 50 μl mouse monoclonal anti-Factor VIII:C antibody (i.e., IgG1k which is commercially available from Molecular Biochemicals (previously known as "Boehringer-Mannheim"), Indianapolis, Ind. (diluted 1:500) in 100 mM sodium carbonate buffer, pH 9.2. Blank wells are coated similarly with 0.25 μg of bovine serum albumin (BSA). The plates are washed three times 50 μl each wash with 50 mM Tris-HCl, pH 7.5 containing 150 mM NaCl and 0.5% (v/v) Tween-20 (TBST), available from Bio-Rad Laboratories, Richmond, Calif. and incubated at 37° C. for one hour with 50 μl conditioned media or cell lysates. The cell lysates were obtained by incubating for 20 minutes with 1 ml of ice-cold 20 mM TRIS-HCL, pH 8.0 buffer containing 150 mM NaCl, 1% (v/v) NP-40 and 1 μg/ml aprotinin. At the end of the incubation, the plates are washed three times with TBST, as above, and incubated at 37° C. for another hour with 50 μl of 1:500 diluted monoclonal anti-Factor VIII:C antibody. The plates are washed three times with TBST and incubated for one hour with alkaline phosphatase-conjugated goat anti-mouse IgG, available from Molecular Biochemicals, Indianapolis, Ind., (diluted 1:2,000 in 50 mM Tris-HCl, pH 7.5). After washing the plates three times with TBST, the plates are incubated with 50 μl of phosphatase substrate cocktail (50 mM p-nitrophenyl phosphate in 500 mM glycine-NaOH buffer, pH 10.0 containing 100 mM MgCl$_2$ and 100 mM ZnCl$_2$). The absorbance is read at approximately 405 nm after 30 minutes by using an EIA microplate reader, Model 2550 with a 405 nm filter, both available from Bio-Rad Laboratories, Richmond, Calif. If the sample has any absorbance above the absorbance level of the blanks, the sample is considered to be immunopositive.

Other terms employed herein not specifically defined immediately above are well known to those of ordinary skill in the art and/or are also further defined in the specification either expressly or indirectly.

As an overview, the present invention relates to methods of inhibiting angiogenesis, i.e., the growth of capillary endothelial cells which form new blood microvessels. Furthermore, the present invention is directed methods of treating disease states, e.g., tumors such as malignant and benign tumors, characterized by an abnormally high amount of angiogenesis.

The present invention includes inhibiting angiogenesis by administering a nucleoside in an therapeutically amount effective to inhibit angiogenesis, to a patient in need of such treatment, e.g., a patient having a disease state characterized by an abnormally high amount of angiogenesis. For instance, the present invention may inhibit neovascularization of a solid tumor tissue. The present invention is also directed to inhibiting endothelial cell proliferation by administering to an endothelial cell a proliferation inhibiting amount of the compounds of the present invention.

The nucleoside is preferably a uridine, a cytidine, or a deoxythymidine, and more preferably a uridine. The nucleoside is preferably a glucosamine containing pyrimidine nucleoside, and more preferably a N-acetylated glucosamine containing pyrimidine nucleoside. Preferred examples of the glucosamine containing pyrimidine nucleoside include homologues of tunicamycin. Tunicamycin, a 840 dalton glucosamine-containing pyrimidine nucleoside, exists in 16 different homologues, differing mostly in the fatty acid side chain, which can be synthesized by *Streptomyces lysosuperificus*, as disclosed in ELBEIN, "Inhibitors of the Biosynthesis and Processing of N-linked Oligosaccharide Chain", *Annu. Rev. Biochem.*, 56:497-534 (1987); and DUKSIN et al., "Relationship of the Structure and Biological Activity of the Natural Homologues of Tunicamycin", *J. Biol. Chem.*, 257:3105-3109 (1982), the disclosures of which are herein incorporated by reference in their entireties.

Of these homologues, the present invention includes those which are effective N-glycosylation inhibitors. In the present application, active homologues of tunicamycin are those which are N-acetylglucosaminyl-1-phosphate transferase inhibitors, and which block $Glc_3Man_9GlcNAc_2$-PP-Dol (OSL) assembly and consequently protein N-glycosylation, as generally disclosed in MAHESHWARI et al., "Interferon Treatment Inhibits Glycosylation of a Viral Protein", *Nature*, 287:454-456 (1980), the disclosure of which is herein incorporated by reference in its entirety. For instance, DUKSIN et al. (1982), cited above, the disclosure of which is herein incorporated by reference in its entirety, discloses that eight tunicamycin homologues ($A_1$, $A_2$, $B_1$, $B_2$, $C_1$, $C_2$, $D_1$, and $D_2$) which inhibit N-glycosylation.

The present invention is also directed to methods of administering derivatives of tunicamycin that function as angiogenesis inhibitors. It is expected that optimization of tunicamycin, e.g., by using combinatorial chemistry techniques, will yield additional compounds which are effective angiogenesis inhibitors. For instance, the present invention is directed to derivatives of tunicamycin that are at least as effective as tunicamycin with respect to inhibiting angiogenesis.

For example, tunicamycin derivatives which function as angiogenesis inhibitors are expected to include compounds of the following general structure (I):

(I)

where R may be:
$(CH_3)_2$—CH—$(CH_2)_n$—CH=CH—(CO)—
where: n may be 1-12, or 4-12, or 6-12, or 8-12
α β unsaturated may be trans or cis;
$CH_3$—$(CH_2)_w$—CH=CH—(CO)—
where: w may be 1-12, or 4-12, or 6-12, or 8-12
α β unsaturated may be trans or cis;
$C_xH_{2x+1}$—CH=CH—(CO)—
where: x may be 1-30, or 3-25, or 6-20, or 12-14
α β unsaturated may be trans or cis;
$(CH_3)_2$—CH—$(CH_2)_y$—(CO)—
where: y may be 1-12, or 4-12, or 6-12, or 8-12
α β unsaturated may be trans or cis; or
$CH_3$—$(CH_2)_z$—(CO)—
where: z may be 1-12, or 4-12, or 6-12, or 8-12
α β unsaturated may be trans or cis.

Regarding n, w, y, and z, it is noted that as these variables increase, the compound becomes more lipophilic and the solubility of the compound would decrease. Accordingly, the maximum value for n, w, y, and z is expected to be 12.

Although the pyrimidine nucleoside of formula (I) is a uridine, it may also be a cytidine or a deoxythymidine.

Taking into consideration the existence of several active homologues of tunicamycin and the expected functional derivatives of tunicamycin, it may be possible to use mixtures of homologues of tunicamycin and/or mixtures of tunicamycin derivatives. The use of such mixtures may reduce side effects and increase efficacy.

The compounds of the present invention, including tunicamycin and functional derivatives thereof, are expected to function via the following mechanisms.

In one aspect, the present invention is directed to methods of administering compounds which inhibit GlcNAc 1-P transferase. For instance, the N-glycosylation inhibiting homologues of tunicamycin are known to be GlcNAc 1-P transferase inhibitors. The mechanism for how these homologues of tunicamycin inhibit GlcNAc 1-P transferase is competitive inhibition. While not wishing to be bound by theory, it is believed that the substrate of GlcNAc 1-P transferase, UDP-N-acetylglucosamine, has a structural element which is similar to a structural element of tunicamycin. Thus, it is believed that binding takes place between tunicamycin and GlcNAc 1-P transferase, such that the GlcNAc 1-P transferase is unable to bind with UDP-N-acetylglucosamine.

In another aspect, the present invention is directed to methods of administering compounds which reduce Dol-P-Man synthase activity in vivo. As discussed above, Dol-P-Man synthase is a "key" glycosyltransferase in the Dol-P pathway. Dol-P-Man activity is regulated by cAMP phosphorylation.

The Examples of the present application show that availability of $Glc_3Man_9GlcNAc_2$-PP-Dol (OSL) is critical not only for the endothelial cell proliferation during angiogenesis but it may also act as an essential intermediate for cell proliferation and apoptosis signaling, as disclosed in MARTÍNEZ et al., "Tunicamycin Inhibits Capillary Endothelial Cell Proliferation by Inducing Apoptosis", *Angiogenesis: From the Molecular to Integrative Pharmacology*, pp. 197-208 (2000), the disclosure of which is herein incorporated by reference in its entirety. See also MACLAG et al. (1981), cited above, the disclosure of which is herein incorporated by reference in its entirety. The observations of WALKER et al. (1998), CARLBERG et al. (1996), and CHANG et al. (1996), the disclosures of which are herein incorporated by reference in their entireties, as discussed in the background of the present application, are consistent with the conclusion that a signal for endothelial cell proliferation lies in the assembly of $Glc_3Man_9GlcNAc_2$-PP-Dol (OSL).

In view of the above, by blocking GlcNAc 1-P transferase and reducing Dol-P-Man synthase activity, the methods of the present invention prevent synthesis of $Glc_3Man_9GlcNAc_2$-PP-Dol (OSL). As noted above, inhibition of OSL biosynthesis inhibits endothelial cell proliferation.

In this regard, blocking OSL synthesis leads to an accumulation of under- or unglycosylated Factor VIII:C in cells. Factor VIII:C is an asparagine-linked $M_r 270,000$ glycoprotein. As discussed in U.S. Pat. No. 4,670,394 to POLLARD et al., the disclosure of which is herein incorporated by reference in its entirety, Factor VIII:C is a blood clotting factor that corrects the blood coagulation abnormality in classic hemophilia (hemophilia A). Factor VIII:C is sometimes designated as Factor VIII:AHF.

Figure 12:
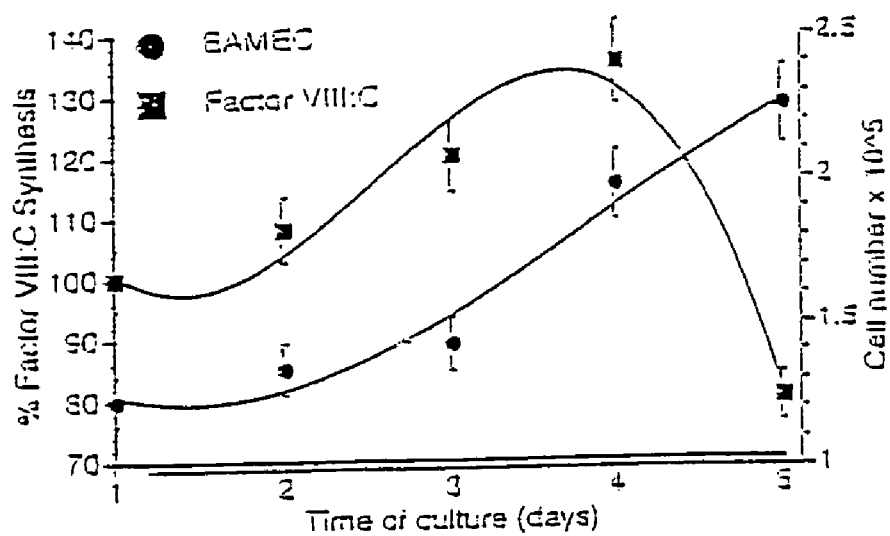
FIG. 12 shows the relationship between capillary endothelial cell proliferation and Factor VIII:C gene expression. Cells were cultured in 2% (v/v) heat-inactivated fetal bovine serum containing EMEM. At different times cells were withdrawn in duplicate. One part was processed for cell number determination by counting in a hemacytometer, and the other part was metabolically labeled with 40 μCi/ml of [$^{35}$]methionine (Sp. Act.>1,000 Ci/mmol) for one hour at 37° C. The cells were harvested, lysed, immunoprecipitated with anti-Factor VIII:C antibody, separated on a 10% (w/v) sodium dodecyl sulfate polyacrylamide gel electrophoresis (SDS-PAGE), autoradiographed, and quantitated in a densitometer scanner. (●) Cell number; each point represents the mean±SEM from three determinations (n=3) and, (■) Factor VIII:C expression.

Factor VIII:C is generally not synthesized in cells other than capillary endothelial cells, as generally discussed in POLLARD et al., the disclosure of which is herein incorporated by reference in its entirety. The exact reason why the gene for blood clotting antigen, Factor VIII:C is expressed in these capillary endothelial cells is currently unknown. It has, however, been suggested that the endothelial Factor VIII:C perhaps activates specific proteases as in the blood-coagulation cascade, which, during angiogenesis, helps the endothelial cells to migrate and to become invasive. Expressing a higher level of Factor VIII:C 24 hours prior to reaching optimum cellular proliferation, as shown in FIG. 12 which is discussed in more detail below, and also as discussed in BANERJEE, "Angiogenesis: Characterization of a Cellular Model", *Puerto Rico Hlth. Sci. J.*, 17:327-333 (publication date unknown), the disclosure of which is herein incorporated by reference in its entirety.

Under- or unglycosylated Factor VIII:C is immunopositive Factor VIII:C which is defined above. In this regard, Factor VIII:C needs to be glycosylated to be functional. While not wishing to be bound by theory, Factor VIII:C may be responsible for activating metalloproteases which assist in penetration of the cellular matrix during capillary invasion during angiogenesis. Thus, apart from its participation in the blood coagulation pathway, Factor VIII:C in capillary endothelial cells is believed to be involved in activating metalloproteases during endothelial cell migration and invasion.

The accumulation of immunopositive Factor VIII:C is associated with apoptosis. In particular, accumulation of immunopositive Factor VIII:C is associated with the cell cycle being arrested during G1 phase. Since the cell cycle in the methods of the present invention is arrested in G1 phase as opposed to a subsequent phase, the present invention is relatively efficient. In particular, the amount of the compounds of the present invention is relatively low so that side effects can be minimized.

Morphological evaluation has indicated that cell proliferation and differentiation are mutually exclusive events. Survival of cells in low-serum concentrations (i.e., 1% (v/v)) and without processing through the proliferative pathway, hypothesized that the low-proliferative response may either be mediated by a depletion in serum growth-factor(s) concentrations or due to an appearance of anti-metabolites during their growth. This may also be true for cultures exhibiting putative capillary-lumen formation when maintained in 2% (v/v) serum for a relatively long period of time. Earlier transmission electron microscopic studies established that these cells synthesize and secrete basal lamina structures and engage in transcytosis, a characteristic ultrastructural and functional combination of exocytosis and endocytosis across the thin endothelial cell processes, as discussed in BANERJEE et al., "Endothelial Cells from Bovine Adrenal Medulla Develop Capillary-like Growth Patterns in Culture", *Proc. Natl. Acad. Sci.* (*USA*), 82:4702-4706 (1985), the disclosure of which is herein incorporated by reference in its entirety. Scanning electron microscopy has now documented a distinct surface morphology during their proliferation as well as when they were undergoing differentiation into capillary-like structures.

Addition of the N-glycosylation inhibitor, tunicamycin in the culture medium, demonstrated a reduction in endothelial cell proliferation, and increased surface blebbing. Cell cycle analysis by flow cytometry indicated that apoptosis is the primary cause of the inhibitory response to tunicamycin. Cells cultured in the presence of 1 µg/ml tunicamycin reduced the cell proliferation. Scanning electron microscopy of the tunicamycin-treated cells detected considerable surface blebbing, a morphology not seen in controls even after prolonged culturing. This suggested that tunicamycin induces cellular suffering, as discussed in MAJNO et al., *Cells, Tissues, and Disease: Principle of General Pathology*, pp. 123-173 (1996), the disclosure of which is herein incorporated by reference in its entirety. Flow cytometric analysis revealed that in the presence of tunicamycin, the cells underwent apoptosis, i.e., programed cell death.

Nearly, 70% of the synchronous cell population entered into apoptosis after exposure to tunicamycin for 32 hours as indicated in FIGS. 13B-13D, discussed in more detail below. This was certainly not due to cell toxicity, because a similar growth reduction has been observed at a wide range of tunicamycin concentrations (i.e., 0.5 µg/ml-5.0 µg/ml), and the effect was reversible, as discussed in MARTINEZ et al., "N-glycosylation Inhibition on Endothelial Cell Proliferation and Viability", *FASEB J.*, 12:231a (1998), the disclosure of which is herein incorporated by reference in its entirety. In addition, more than 70% of total adherent cells were viable under such conditions. The presence of a large population of apoptotic cells may suggest a relationship between the onset of tunicamycin-induced apoptosis and the cell cycle, where the N-glycans play a critical role in cell cycle check points. These results indicate that induction of apoptosis is the primary cause for the inhibition of capillary endothelial cell proliferation by tunicamycin. High level of immunopositive Factor VIII:C in the conditioned media from cells treated with tunicamycin confirmed that intracellular accumulation of unglycosylated Factor VIII:C might serve as an apoptotic signal causing changes in cell permeability and consequently osmotic lysis. Deglycosylation of Factor VIII:C in fact, by N-glycanase digestion has been shown to eliminate the biological activity of Factor VIH:C, (data not shown).

To obtain apoptosis, it is important for endothelial capillary cells to be in the presence of the compounds of the present invention for at least about 12 hours, more preferably 16 hours, most preferably 32 hours, during G1 phase. The cells undergoing apoptosis are typically observed by light microscopy to have cell shrinkage, compaction of nuclei, membrane fragmentation, etc., typical of apoptotic response. Scanning electron microscopy also exhibits cell swelling and a considerable surface blebbing in cells undergoing apoptosis.

The apoptotic response observed during inhibition of capillary endothelial cells by tunicamycin was due to the inhibition of protein N-glycosylation process and not due to the inhibition of protein synthesis. Because replacing tunicamycin with a protein synthesis inhibitor cycloheximide though inhibited the cell proliferation in a time- and dose-dependent manner but did not induce apoptosis (data not shown). In addition, when both tunicamycin and cycloheximide were present, the inhibition of cellular proliferation was additive but not synergistic. This observation contradicts the possibility that tunicamycin action was dependent upon the inhibition of active protein synthesis. Any earlier claim on the inhibition of protein synthesis by tunicamycin therefore needs critical re-examination with a correct tunicamycin homologue, as disclosed in STRUCK et al., *The Biochemistry of Glycoproteins and Proteoglycans*, pp. 35-83 (1980), the disclosure of which is herein incorporated by reference in its entirety. This observation is extremely important because some homologues of tunicamycin have indeed been found to be protein synthesis inhibitor, as disclosed in DUKSIN et al. (1982), cited above, the disclosure of which is herein incorporated by reference in its entirety.

In view of the above mechanism, since cells other than capillary endothelial cells generally do not synthesize Factor VIII:C, other cells are less affected by administration of the compounds of the present invention. Accordingly, the side effects of the present invention are expected to be relatively low.

In view of the above mechanism, proliferating cells are more vulnerable to the compounds of the present invention because cell components duplicated during proliferation.

Accordingly, although the administration of the compound of the present invention is typically systemic, proliferating endothelial cells are affected more than non-proliferating cells.

While not wishing to be bound by theory, the compounds of the present invention may also cause unfolded protein response (UPR) in cells. In this regard, impairment of the dolichol-cycle by the compounds of the present invention may cause an unfolded protein response followed by G1 arrest and activation of caspases leading to programmed cell death of endothelial cells, and limits intratumoral microvascular density in breast carcinoma. As noted above, While not wishing to be bound by theory, the compounds of the present invention may activate caspase(s) due to unfolded protein response.

While not wishing to be bound by theory, the compounds of the present invention may also impair the expression of cyclins D, E and A during cell growth arrest.

While not wishing to be bound by theory, the compounds of the present invention may further down-regulate cyclin D-, E- and A-dependent kinase activities (cdks), and mitogen-dependent activities of the extracellular signal-activated protein kinases ERK1 and ERK2.

While not wishing to be bound by theory, the compounds of the present invention may limit disease tissue, e.g., tumors such as breast carcinoma, through limiting intratumoral microvascular density.

While not wishing to be bound by theory, the compounds of the present invention may also prevent integrin receptor glycosylation. As noted above, stimulation of some integrin receptors is involved in angiogenesis. By blocking integrin receptor glycosylation, the integrin receptors would not be functional. Since the integrin receptors would be nonfunctional, these receptors could not be stimulated to promote angiogenesis. Therefore, angiogenesis would be inhibited and the effect of the compounds of the present invention would be multiplied.

While not wishing to be bound by theory, the compounds of the present invention may also prevent VEGF receptor glycosylation. As noted above, stimulation of VEGF receptors is involved in angiogenesis. By blocking VEGF receptor glycosylation, the VEGF receptors would not be functional. Since the VEGF receptors would be nonfunctional, these receptors could not be stimulated to promote angiogenesis. Therefore, angiogenesis would be inhibited and the effect of the compounds of the present invention would be multiplied.

While not wishing to be bound by theory, the compounds of the present invention may block glycosylation of receptors which are involved in cell attachment. The receptors whose glycosylation might be blocked include β, integrin, and VEGF receptors. As a result, cell attachment would be minimized which would also lead to apoptosis.

While not wishing to be bound by theory, another mechanism of the present invention may involve activation of caspase(s). In particular, the addition of the compounds of the present invention could cause the ER to release $Ca^{+2}$ which would activate caspase(s). Activated caspases break down the cell and lead to apoptosis.

The following discussion of period of administration, dosages, and recovery time between periods of administration is intended to be a guideline. As discussed in more detail below, the appropriate period of administration, dosages, and recovery time between periods of administration are dependent upon several factors. Furthermore, the following discussion is based on cell culture results. Although no animal studies have been conducted to determine the optimal treatment protocol, it is expected that the optimal protocol will be similar to that indicated by the cell culture results. Additionally, it is expected that the present invention may be practiced on animals, such as mammals, such as humans.

While not wishing to be bound by theory, the period of administration of tunicamycin is expected to be dependent upon several factors, such as the stage of the disease tissue, e.g., tumor, endogenous factors, behavior of the disease tissue, e.g., tumor, dosage, and the patient's individual physiology. For later stage disease tissue, e.g., tumors, the period of administration should generally be longer. For example, if the tumor has metastasized, the period of administration should generally be longer. Endogenous factors include, e.g., the growth factor VEGF. For example, although the effect of VEGF can be overcome by the administration of the composition of the present invention, the presence of relatively high levels of VEGF should generally increase the period of administration. Of course, more resistant disease tissue, e.g., tumors, will generally lead to longer periods of administration. For smaller dosages, the period of administration will generally be longer. The period of administration should also be affected by the patients individual physiology. For instance, if the individual is healthy, the administration can be for a longer time period. Also, if the individual is tolerant to the composition of the present invention, the administration should generally be for a longer time period. Conversely, if an individual has adverse reactions, the treatment method of the present invention may not be appropriate or the period of administration may be reduced.

In this regard, during the period of administration, each individual patient should be examined to see how they are reacting to the treatment of the present invention. For instance, the patient should be examined for the above noted possible adverse reactions. The disease tissue, e.g., tumor, should also be examined, e.g., by biopsy or soft X-ray microscopy, to see whether the period of administration and/or dose should be modified.

In view of the above, the period of administration is typically about 1 week to 6 months, more typically about 1 week to 3 months, even more typically about 2 weeks to 1 month, and most typically about 2 to 3 weeks. If the period of administration is too long, the period of recovery between periods of administration is increased and adverse impacts on the patient's health are more likely. If the period of administration is too short, the disease tissue, e.g., tumor, may not be reduced.

During the period of administration, the administration should generally be at least daily. Although it is expected that the administration may be by intraperitoneal injection near the disease tissue, e.g., tumor mass, to minimize side effects, the preferred manner of injection is expected to be intravenous. The manner of administration may also be transdermal, intramuscular, topical, subcutaneous, intracavity, peristaltic. Regarding intraperitoneal injection near the disease tissue, e.g., tumor mass, it is expected that micropumps may be implanted in or near the disease tissue, e.g., tumor mass, to administer the dose in a manner similar to insulin pumps.

The composition of the present invention may comprise a pharmaceutical composition comprising the compounds of the present invention and pharmaceutically acceptable carrier or excipient. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutic composition contains an angiogenesis-inhibiting amount of an active compound of the present invention, typically formulated to contain an amount of at least 0.1 weight percent of active compound of the present invention per weight of total therapeutic composition. A weight percent is a ratio by weight of active compound to total composition. Thus, for example, 0.1 weight percent is 0.1 grams of active compound per 100 grams of total composition.

While not wishing to be bound by theory, the dosage is expected to depend upon factors such as period of administration, stage of disease tissue, e.g., tumor, endogenous factors, disease tissue, e.g., tumor, behavior, and the patient's individual physiology. For shorter periods of administration, higher dosages are generally used. For later stage disease tissue, e.g., tumors, the dosage should generally be higher. For example, if the tumor has metastasized, the dosage should generally be higher. Regarding endogenous factors, if, e.g., VEGF levels are high, the dosage should generally be higher. Dosages will generally be higher for more resistant and/or aggressive disease tissue, e.g., tumors. The dosage should also be affected by the patients individual physiology. For instance, if the individual is healthy, the dosage can be higher. Also, if the individual is tolerant to the composition of the present invention, the dosage should generally be higher. Conversely, if an individual has adverse reactions, the treatment method of the present invention may not be appropriate or the dosage should generally be reduced.

In this regard, during the initial period of administration, the dosage should generally be low and then can be gradually increased depending upon how the patient reacts to the treatment of the present invention. For instance, during the first week of administration the dosage should generally be small. After the first week, if there are no adverse reactions, the dosage may be increased during the second week. After the second week, if there are still no adverse reactions, the dosage may be increased even further during the third week.

In view of the above, the dosage will typically be about 5 to 20 mg/kg of body weight, more typically about 6 to 15 mg/kg of body weight, even more typically about 7 to 12 mg/kg of body weight, and most typically about 8 to 10 mg/kg of body weight. If the dosage is too high, the period of recovery between periods of administration is increased and adverse impacts on the patient's health are more likely. In this regard, if the dosage is too high, cell recovery may not be possible. If the dosage is too low, the disease tissue, e.g., tumor, may not be reduced.

Accordingly, examples of the dosage and period of administration are expected to typically include a dosage of about 5 to 20 mg/kg of body weight for about 1 week to 6 months, more typically a dosage of about 6 to 15 mg/kg of body weight for about 1 week to 3 months, even more typically a dosage of about 7 to 12 mg/kg of body weight for about 2 weeks to 1 month, and most typically a dosage of about 8 to 10 mg/kg of body weight for about 2 to 3 weeks. An advantage of the present invention is that side effects can be minimized in a dose dependent and time dependent manner.

The present invention is also directed to the observation that after an initial period of administration, a recovery period between periods of administration is an effective aspect of treatment. In this regard, it has surprisingly been found that the side effects of the methods of the present invention are reversible. For example, without data similar to that found in the examples of the present application, the mechanism of action for tunicamycin would not be clear and, therefore, the appropriate treatment protocol would also not be clear. For instance, it has been surprisingly found that tunicamycin is truly anti-angiogenic, as opposed to being cytotoxic.

In view of the above and in view of the data shown in the examples of the present application, after the initial period of administration, the patient should be allowed to recover during which time the composition of the present invention is not administered. The period of recovery between periods of administration is expected to depend upon factors such as the health of the patient. If the patient is generally healthy, the period of recovery between periods of administration may be less.

In view of the above, the period of recovery between periods of administration is expected to be typically about 1 week to 1 year, more typically about 2 weeks to 6 months, even more typically about 2 weeks to 3 months, and most typically about 2 to 4 weeks. In this regard, when treating early stage disease, e.g., tumors, with small doses and short periods of administration, the recovery time between periods of administration is expected to be about 1 to 3 weeks. When treating more advanced disease tissue, e.g., tumors, which require larger doses and larger periods of administration, the recovery time between periods of administration is expected to be about 3 to 5 weeks. Accordingly, the recovery time between periods of administration is typically at least about 1 week, or at least 2 weeks, or at least 3 weeks, or at least 4 weeks, or at least 5 weeks. If the recovery period between periods of administration is too short, adverse impacts on the patient's health are more likely. If the recovery period between periods of administration is too long, the disease tissue, e.g., tumor, may also recover if it has not already been eliminated.

After recovery, the administration may be resumed. The cycle of administration and recovery may be repeated until the disease tissue, e.g., tumor, has been eliminated. While not wishing to be bound by theory, it is expected that the number of rounds of administration necessary to eliminate disease tissue, e.g., tumor, is expected to typically be about 1 to 10, more typically about 2 to 8, and most typically about 3 to 5.

The compounds of the present invention may also be administered in combination with other angiogenesis inhibitors. For instance, if the compounds of the present invention and the other angiogenesis inhibitors have different targets, the effect is expected to be at least additive and side effects would be expected to decrease. In particular, the different targets may be different mechanisms and/or different cells.

In this regard, the compounds of the present invention target both disease tissue, e.g., tumor cells, and capillary endothelial cells. Thus, the compounds of the present invention target actively proliferating disease tissue, e.g., tumor cells. Accordingly, it is expected that the compounds of the present invention may be used with compositions which target endothelial cells or disease tissue cells.

While not wishing to be bound by theory, an advantage of the compounds of the present invention is that they are preferably cell permeable and freely diffuse into cells. As a result of this property, the administration of the compounds of the present invention is relatively simple and the dosages are relatively low. Since the dosages are relatively low, the side effects are expected to be relatively low.

Since the compounds of the present invention inhibit glucosaminyl-1-phosphate (GlcNAc 1-P) transferase which is involved in the first step of $Glc_3Man_9GlcNAc_2$-PP-Dol (OSL) biosynthesis, the compounds of the present invention are efficient inhibitors of angiogenesis.

Another advantage of the compounds of the present invention is that they are preferably lipophilic. For example, tunicamycin is lipophilic so that a carrier is not necessary. In this regard, while not wishing to be bound by theory, tunicamycin may be able to pass through cell walls because of its lipophilic nature.

Additionally, since the compounds of the present invention are not peptides, they are relatively easy to inject and administer.

It is expected that the types of diseases which may be treated by the present invention include diabetic retinopathy, atherosclerotic plaques, scleroderma, hypertrophic scarring, vascular adhesions, angiofibroma, trachoma and corneal graft neovascularization, neovascular glaucoma, thrombosis, restenosis, osteoporosis, macular degeneration, arthritis, hemangiomas, psoriasis, etc. The present invention may be used to treat any solid tumors, e.g., benign and malignant tumors. For instance, the present invention may be used to treat any cancer involving a massive growth of tissue, such as breast, prostate, cervical, lung, pancreas, colon, larynx, and uterine cancer.

An advantage of the present invention is that the compositions of the present invention will also affect secondary tumors. In this regard, many known treatments are only directed to the primary tumor.

The present invention will be further illustrated by way of the following Examples. These examples are non-limiting and do not restrict the scope of the invention.

Unless stated otherwise, all percentages, parts, etc. presented in the examples are by weight.

Cell Culture

The following examples involve bovine adrenal medullary microvascular endothelial cells which undergo cellular proliferation and differentiation upon culturing in vitro as observed by light and scanning electron microscopy. These cells are described in U.S. Pat. No. 4,670,394 to POLLARD et al., the disclosure of which is herein incorporated by reference in its entirety. A deposit of a line of these endothelial cells has been made in the American Type Culture Collection, Rockville, Md., and assigned accession number CRL 8659.

These cells have been characterized in BANERJEE, Angiogenesis: Characterization of a Cellular Model", *Puerto Rico Health Science Journal*, 17:327-333 (publication date unknown); BANERJEE et al., "Endothelial Cells from Bovine Adrenal Medulla Develop Capillary-like Growth Patterns in Culture", *Proc. Natl. Acad. Sci (USA)*, 82:4702-4706 (1985); BANERJEE et al., "Microvascular Endothelial Cells from Adrenal Medulla—a Model for in vitro Angiogenesis", *Models, Modulators, and Clinical Applications*, pp. 7-18 (1998); BANERJEE et al., "Is Asparagine-linked Protein Glycosylation an Obligatory Requirement for Angiogenesis?", *Indian J. Biochem. Biophys.*, 30:389-394 (1993); YOUDIM et al., "Isolated Chromaffin Cells from Adrenal Medulla Contain Primarily Monoamine Oxidase B", *Science*, 224:619-621 (1984); YOUDIM et al., "Steroid Regulation of Monoamine Oxidase Activity in the Adrenal Medulla", *FASEB J.*, 3:1753-1759 (1989); BANERJEE et al., "Expression of Blood Clotting Factor VIII:C Gene in Capillary Endothelial Cells", *FEBS Letts.*, 306:33-37 (1992); MARTÍNEZ et al., "Expression of $Glc_3Man_9GNAc_2$-PP-Dol is a Pre-requisite for Capillary Endothelial Cell Proliferation", *Cell Molec. Biol.*, 45:137-152 (1999); BANERJEE et al., "Biphasic Estrogen Response on Bovine Adrenal Medulla Capillary Endothelial Cell Adhesion, Proliferation and Tube Formation", *Mol. Cell Biol.*, 177:97-105 (1997); BANERJEE, "Microenvironment of Endothelial Cell Growth and Regulation of Protein N-glycosylation", *Indian J. Biochem. Biophys.*, 25:8-13 (1998), the disclosures of which are herein incorporated by reference in their entireties.

As an overview, these cells respond to the growth promoting activity of both serum and basic fibroblast growth factor (bFGF/FGF-2). A synchronization protocol arrested ~90% of the cell population in the $G0/G_1$ phase, and established that it requires 68 hours for the cell to divide in a growth medium containing 2% (v/v) of heat inactivated (56° C. for 30 minutes) fetal bovine serum. In particular, flow cytometric analysis of a synchronized culture indicates that cells take 68 hours to complete one cell cycle spending 36 hours in the G1 phase, 8 hours in the S phase, and 24 hours in the G2+M phase when cultured in EMEM containing 2% (v/v) heat-inactivated fetal bovine serum (FBS). At 10% (v/v) serum, or in the presence of bFGF/FGF-2 (10 ng/ml-100 ng/ml) time for the cell cycle is reduced to 56 hours due to shortening of the G1 phase by 12 hours. The duration of the cell cycle is affected by the presence of mitogens/agonists, or inhibitors, as discussed in the following examples.

Serum concentration below 2% (v/v) arrested cell proliferation and induced capillary lumen-like structure formation with 48 hours. The cells in 2% (v/v) serum were unable to complete two full cycles before differentiating. Thus, culture confluency was never reached. Cells cultured in 10% (v/v) serum were, however, able to reach confluency prior to differentiation (at least two complete cycles). Thus, 2% (v/v) serum containing medium was selected as the control, because under these minimal growth promoting conditions background compensation would be minimal. This control also allowed experimental growth promoting or inhibitory conditions to have a clearly distinguishable effect from the control (i.e., background).

Expression of the blood clotting antigen Factor VIII:C (a $M_r 270,000$ dalton N-linked glycoprotein and a marker of the endothelial cells) preceded the endothelial cell proliferation, and established a temporal relationship.

The above described capillary endothelial cells were maintained in EMEM containing 10% (v/v) heat-inactivated FBS (30 minutes @ 56° C.), glutamine (2 mM), penicillin (50 units/ml), streptomycin (50 µg/ml), and nystatin (100 units/ml), i.e., a complete EMEM at 37° C. in a humidified $CO_2$ incubator (5% (v/v) $CO_2$/95% (v/v) air) in tissue culture flasks or dishes without collagen underlay or other extracellular matrix components, as described before in BANERJEE et al., "Endothelial Cells from Bovine Adrenal Medulla Develop Capillary-like Growth Patterns in Culture", *Proc. Natl. Acad. Sci. (USA)*, 82:4702-4706 (1985), the disclosure of which is herein incorporated by reference in its entirety. Cells were subcultured once a week unless otherwise mentioned.

EXAMPLE 1

Alternation of Endothelial Cell Morphology

Cells in the amount of $2.0 \times 10^4$ were seeded per well in 24-well clusters in 1 ml complete EMEM containing 10% (v/v) serum and allowed to grow for 72 hours. Media were removed and the cells were washed twice with phosphate-buffer saline, pH 7.4 (PBS). Cells were synchronized by incubating for 48 hours in 2 mM hydroxyurea in serum-free EMEM with glutamine (2 mM) and one-third of penicillin-streptomycin used in a regular culture condition, followed by incubating 24 hours in serum-free EMEM, as discussed in CAO et al., "Modified Method of Mammalian Cell Synchronization Improves Yield and Degree of Synchronization", *Exp. Cell Res.*, 193:405-410 (1991), the disclosure of which is herein incorporated by reference in its entirety.

The synchronized population of the above described bovine capillary endothelial cells was exposed to tunicamycin (lot number 10922120-07 from Boehringer-Mannheim, Indianapolis, Ind.) with no history of protein synthesis inhibition, for different lengths of time at various concentrations, as shown, e.g., in FIG. 3, in a complete EMEM containing 2% (v/v) fetal bovine serum (FBS) (heat-inactivated) at 37° C. to evaluate the morphological changes. The cells were monitored by phase-contrast light microscopy as well as by scanning electron microscopy.

For scanning electron microscopy, $5 \times 10^3$ cells were cultured on 13 mm round Thermanox coverslips in 12 well clusters (COSTAR) in complete EMEM. Cells were synchronized as mentioned above and cultured in EMEM containing either 2% (v/v) FBS (control), 10% (v/v) FBS or 2% (v/v) FBS plus 1 µg/ml tunicamycin. The coverslips were removed at specified times and the cells were fixed in 2.5% (v/v) glutaraldehyde for 30 minutes. The cells were washed three times (10 minutes each) with Millonigs (1961) isotonic phosphate buffer, pH 7.3, and treated with 1% (w/v) osmium tetroxide for 15 minutes. See MILLONIG, "Advantages of a Phosphate Buffer for Osmium Tetroxide Solutions in Fixation", *J. Appl. Physics*, 32:1637 (1961), the disclosure of which is herein incorporated by reference in its entirety. After washing with isotonic phosphate buffer, pH 7.3 with three changes, the specimens were dehydrated with 30%, 60% and 90% (10 minutes each), and finally with 100% (v/v) acetone in three changes. In the final step, the specimens were treated with 1:1 mixture of 100% (v/v) acetone and Peldry II for 1 hour and then changed to 100% (v/v) Peldry II for 30 minutes. The specimens were cooled below 23° C. (18° to 20° C.), placed under low vacuum (over night), mounted on a sample mount, coated with metal in E5200 Auto Sputter (gold film thickness 200 nm) and examined in Autoscan ETEC Scanning Electron Microscope.

For proliferation assay, cells were trypsinized and counted in a hemacytometer. Viability of cells was determined by trypan blue (0.4% (v/v)) exclusion. Statistical analysis was carried out by StatView II software (Macintosh). Quantitation of cellular differentiation was carried out by observing under a Nikon AlphaShot inverted microscope, and counting the number of capillary lumen-like structures in five randomly selected fields per sample.

In controls, cellular proliferation and differentiation were mutually exclusive, but a complete differentiation was observed only after 5 days. Examination of surface morphology by scanning electron microscopy as a function of time established cellular growth, and differentiation into capillary-like structures. Higher serum concentration (i.e., 10% (v/v)) duplicated the observed morphological changes, but the timing was delayed. Cells cultured in the presence of tunicamycin (1 μg/ml) exhibited cell shrinkage, loss of membrane contact with neighboring cells, apparent compaction of nuclei showing condensed pyknotic appearance and membrane fragmentation when analyzed by light microscopy. Scanning electron microscopy detected a considerable surface blebbing in tunicamycin-treated cells, a morphological change which had never been observed in controls even after culturing for a longer period of time (FIG. 1).

EXAMPLE 2

Inhibition of Cell Growth and Proliferation

Synchronized cells, as described in Example 1, were cultured at 37° C. in complete EMEM containing fetal bovine serum (1% (v/v), 2% (v/v), or 10% (v/v), or complete EMEM with 2% (v/v) fetal bovine serum containing 1 ng/ml –100 ng/ml of bFGF/FGF-2, or containing 0.5 μg/ml to 5.0 μg/ml tunicamycin (lot number 10922120-07 from Boehringer-Mannheim, Indianapolis, Ind.). In each case, the cellular growth and proliferation was monitored by trypan blue exclusion, by counting the cell number, and by their ability to process through the cell cycle by flow cytometry.

Regarding flow cytometry, assessment of the cell cycle was determined by propidium iodide staining of fixed cell nuclei followed by flow cytometry in a FacSort (Beckton Dickinson) according to the method of Krishan (1975) as modified by Vindelov (1977), as discussed in KRISHAN, "Rapid Flow Cytofluorometric Analysis of Mammalian Cell Cycle by Propidium Iodide Staining", *J. Cell Biol.*, 66:188-193 (1975); and VINDELOV, "Flow Cytometric Analysis of Nuclear DNA in Cells from Solid Tumors and Cell Suspensions", *Virchows Arch* (*B*), 24:227-231(1977), the disclosures of which are herein incorporated by reference in their entireties. Briefly, cells were trypsinized, and pelleted by centrifugation at 900 rpm in a bench top centrifuge (Sorvall T6000B). After washing twice with PBS the cell pellet was resuspended in propidium iodide-buffer (PI-buffer; 10 mM Tris-HCl, pH 8.0 containing 10 mM NaCl, 0.7 μM PI, 700 units/liter RNase, and 0.1% (v/v) NP-40), kept in ice for 30 minutes and then fixed with 2% (v/v) paraformaldehyde. After FacSort calibration, 3000 events were counted per sample. Acquisition and analysis of data were carried out by using Cell Quest flow cytometry software (Macintosh-based). Gates: M1=G0/G1, M2=S, M3=G2+M, M4=apoptosis.

Cells maintained a status quo for the first 32 hours whether cultured in serum alone or in the presence of bFGF/FGF-2. Cells proliferated normally in media containing either 2% (v/v) or 10% (v/v) fetal bovine serum, but a maximum cell growth was observed at 10% (v/v) serum. Similarly, bFGF/FGF-2 at 10 ng/ml-100 ng/ml stimulated the endothelial cell proliferation by reducing the lag phase. When the progression of cells through the cell-cycle was evaluated by flow cytometry, cells cultured in 2% (v/v) serum needed approximately 68 hours to complete one cycle spending 36 hours in the G1 phase, 8 hours in the S phase and 24 hours in the G2+M phase. Presence of either 10% (v/v) serum, or 10 ng/ml-100 ng/ml bFGF/FGF-2 reduced the time to complete the cell cycle to 56 hours by decreasing the GI phase by 12 hours.

Cells cultured in the presence of tunicamycin (1 μg/ml) maintained the same level of growth as controls for 24 hours after which the number of cells started declining, and cells never completed the cell cycle. Flow cytometric evaluation revealed that 70% of the cell population entered into apoptosis (i.e., "programmed cell death") after an exposure to tunicamycin for 32 hours. This observation was also confirmed by the appearance of laddering in DNA samples when agarose gel electrophoresis was performed on DNA from tunicamycin-treated cells (FIG. 2). A similar reduction in cell growth has also been observed at all tunicamycin concentrations used in this study (i.e., 0.5 ng/ml-5.0 μg/ml) (not all data shown).

EXAMPLE 3

Isolation of a Highly Sensitive Cell Clone

If the behavior of tunicamycin observed here is truly anti-angiogenic and is not due to cytotoxicity then cells must recover following a tunicamycin treatment that is shorter in duration, and the concentrations are moderate. In fact, a full recovery was observed in 5 days when the above-described synchronized cells cultured at 37° C. were treated with 10 ng/ml tunicamycin for 48 hours; at 1 μg/ml tunicamycin concentration the recovery was approximately 40%, but it was only 12% when 10 μg/ml of tunicamycin was used (where the tunicamycin was from lot number 10922120-07 from Boehringer-Mannheim, Indianapolis, Ind.) (FIG. 3). Cells however, never recovered when the tunicamycin treatment was for 72 hours or longer at 1 μg/ml or 10 μg/ml, respectively (FIG. 3). On the other hand, the recovery was quantitative from a 24 hour exposure to tunicamycin at all concentrations (data not shown).

To understand the precise molecular mechanism of tunicamycin induced apoptosis of capillary endothelial cells, a cell clone was isolated from the parental culture that was maintained in a serum-free media for six weeks following synchronization. The morphology of these cells and their growth profile appear quite different. For example, the shapes are more spindle-like, resembling Kaposi's Sarcoma lesions endothelial cells, as disclosed in FIORELLI et al., "Cytokines from Activated T Cells Induce Normal Endothelial Cells to Acquire the Phenotypic and Functional Features of AIDS-Kaposi's Sarcoma Spindle Cells", *J. Clin. Invest.*, 95:1723-1734 (1995), the disclosure of which is herein incorporated by reference in its entirety. The cells undergo two-population doubling in 2% (v/v) fetal bovine serum, differentiate in 5 days, and complete one cell cycle in approximately 56 hours (FIG. 4).

Most striking however, is that the newly isolated cell clone is quite sensitive to tunicamycin and undergoes apoptosis (i.e., "programmed cell death") in 32 hours when exposed to tunicamycin at 10 ng/ml, a concentration 100-fold less than needed for the parental cells. Recovery from tunicamycin exposure suggested that approximately 60% of cells recovered in 5 days from an exposure to 10 ng/ml tunicamycin for 24 hours. Cells recovered similarly in 5 days from an exposure to 1 μg/ml tunicamycin for 48 hours, but less than 20% when exposed to 10 μg/ml tunicamycin for the same period of time. There was no recovery after exposing the cells to 1 μg/ml-10 μg/ml tunicamycin for 72 hours or more (not all data shown).

EXAMPLE 4

Accumulation of an Asparagine-linked Glycoprotein, Factor VII:C

To support the claim that inhibition of protein N-glycosylation is a primary event in tunicamycin-mediated apoptosis, Factor VIII:C expression during the growth and proliferation of capillary endothelial cells was analyzed. The above-noted bovine capillary endothelial cells express a $M_r 270,000$ dalton N-linked glycoprotein with a biological activity of that of a Factor VIII:C of the blood coagulation cascade, as disclosed in BANERJEE et al., "Expression of Blood Clotting Factor VIII:C Gene in Capillary Endothelial Cells", *FEBS Letts.*, 306:33-37 (1992), the disclosure of which is herein incorporated by reference in its entirety. In endothelial cells derived Factor VIII:C species, the heavy-chain ($M_r 215,00$ dalton) and the light-chain ($M_r 46,000$ dalton) are joined together by disulfide bridge(s). In addition, the light-chain contains approximately 20% N-linked glycans, as disclosed in BANERJEE et al. (1992), cited above, the disclosure of which is herein incorporated by reference in its entirety. The N-linked glycans are essential for the biological activity of Factor VIII:C. Removal of N-glycan chains from human plasma Factor VIII:C almost eliminated its ability to convert Factor X to Factor Xa (data not shown).

Figure 5:
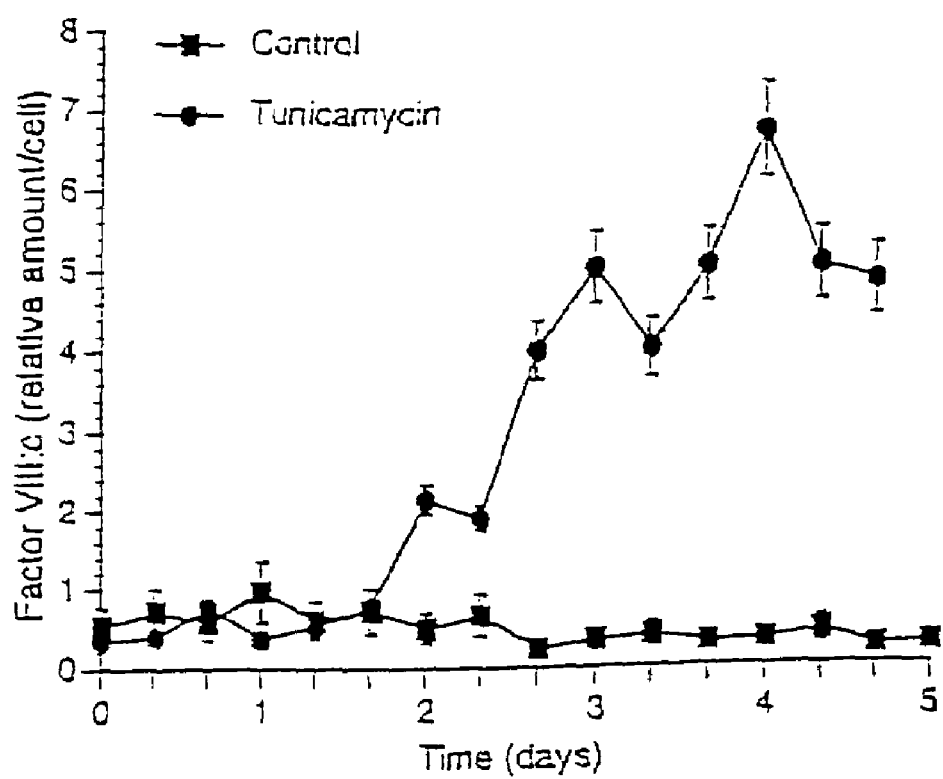
FIG. 5 shows Factor VIII:C level in tunicamycin treated cells. Factor VIII:C was quantitated by enzyme-linked immunoassay. Each point represents the mean±SEM (n=6). (■) Control; (●) tunicamycin (1 μg/ml) treated.

When the Factor VIII:C level was analyzed in control and in tunicamycin-treated (1 µg/ml tunicamycin from lot number 10922120-07 from Boehringer-Mannheim, Indianapolis, Ind.) cells by enzyme-linked immunoassay (ELISA), it was observed that the Factor VIII:C level started increasing from 32 hours onwards in tunicamycin treated cells (FIG. 5).

In conducting ELISA, 96-well microtiter EIA plates, available from Corning Inc., Corning, N.Y., were coated overnight at 4° C. with 50 µl mouse monoclonal anti-Factor VIII:C antibody (i.e., IgG1k which is commercially available from Molecular Biochemicals (previously known as "Boehringer-Mannheim"), Indianapolis, Ind. (diluted 1:500) in 100 mM sodium carbonate buffer, pH 9.2. Blank wells were coated similarly with 0.25 µg of bovine serum albumin (BSA). The plates were washed three times 50 µl each wash with 50 mM Tris-HCl, pH 7.5 containing 150 mM NaCl and 0.5% (v/v) Tween-20 (TBST), available from Bio-Rad Laboratories, Richmond, Calif. and incubated at 37° C. for one hour with 50 µl conditioned media or cell lysates. The cell lysates were obtained by incubating for 20 minutes with 1 ml of ice-cold 20 mM TRIS-HCL, pH 8.0 buffer containing 150 mM NaCl, 1% (v/v) NP-40 and 1 µg/ml aprotinin. At the end of the incubation, the plates were washed three times with TBST, as above, and incubated at 37° C. for another hour with 50 µl of 1:500 diluted monoclonal anti-Factor VIII:C antibody. The plates were washed three times with TBST and incubated for one hour with alkaline phosphatase-conjugated goat anti-mouse IgG, available from Molecular Biochemicals, Indianapolis, Ind., (diluted 1:2,000 in 50 mM Tris-HCl, pH 7.5). After washing the plates three times with TBST, the plates were incubated with 50 µl of phosphatase substrate cocktail (50 mM p-nitrophenyl phosphate in 500 mM glycine-NaOH buffer, pH 10.0 containing 100 mM $MgCl_2$ and 100 mM $ZnCl_2$). The absorbance was read at approximately 405 nm after 30 minutes by using an EIA microplate reader, Model 2550 with a 405 nm filter, both available from Bio-Rad Laboratories, Richmond, Calif.

The results of FIG. 5 indicated that either a reduced level or a complete absence of $Glc_3Man_9GlcNAc_2$-PP-Dol in the presence of tunicamycin makes under- or un-glycosylated Factor VIII:C and pushes the cells threshold to synthesize more biologically active Factor VIII:C. Thus, it is concluded that continuous accumulation of under- or un-glycosylated Factor VIII:C in tunicamycin-treated capillary endothelial cells may be responsible for the induction of apoptosis.

EXAMPLE 5

Materials and Methods

The capillary endothelial cell line from bovine adrenal medulla described above was utilized. Minimal essential medium with Earle's salt (EMEM), glutamine, penicillin-streptomycin, phosphate-buffered-saline, pH 7.4 (PBS), and trypsin-versene were purchased from BioFluids Inc., Rockville, Md. Thermanox coverslips were from Nunc, Inc., Napeville, Ill. Glutaraldehyde and osmium tetroxide were obtained from Electron Microscopy Sciences, Ft. Washington, Pa. Acetone and Peldry II were purchased from Ted Pella, Redding, Calif. Trypan Blue and Nystatin were from GIBCO-BRL, Gaithersberg, Md. Fetal bovine serum (FBS) was a product of HyClone Laboratories, Logan, Utah. Hydroxyurea, propidium iodide, RNase, paraformaldehyde, glutaraldehyde, dimethylsulfoxide, phenyl methyl sulfonyl fluoride (PMSF), N-Tosyl-L-phenylalanine chloromethyl ketone (TPCK), soybean trypsin inhibitor, aprotinin, and leupeptin were obtained from Sigma Chemical Co., St Louis, Mo. Acrylamide, bis-acrylamide, N,N,N',N'-tetramethylenediamine (TEMED), SDS, Tween 20, E5200 auto sputter coater, and β-mercaptoethanol were purchased from Bio-Rad Laboratories, Hercules, Calif. Monoclonal antibody (IgG1k) to human Factor VIII:C, alkaline-phosphatase conjugated mouse anti-rabbit IgG, and Tunicamycin (lot number 10922120-07) were obtained from Boehringer-Mannheim, Indianapolis, Ind. [$^{35}$S]Methionine, [$^{14}$C]methylated protein standards, and Protein A-Sepharose CL-4B were purchased from Amersham Pharmacia Biotech, Arlington Height, Ill. All chemicals were of the highest purity grade.

Culturing of capillary endothelial cells. The stock culture of capillary endothelial cells was maintained in EMEM containing 10% (v/v) heat-inactivated FBS (30 minutes @ 56° C.), glutamine (2 mM), penicillin (50 units/ml), streptomycin (50 µg/ml), and nystatin (100 units/ml), i.e., a complete EMEM at 37° C. in a humidified $CO_2$ incubator (5% (v/v) $CO_2$/95% (v/v) air) in tissue culture flasks or dishes without collagen underlay or other extracellular matrix components, as described before in BANERJEE et al., "Endothelial Cells from Bovine Adrenal Medulla Develop Capillary-like Growth Patterns in Culture", *Proc. Natl. Acad. Sci.* (*USA*), 82:4702-4706 (1985), the disclosure of which is herein incorporated by reference in its entirety. Cells were subcultured once a week unless otherwise mentioned.

Proliferation and Differentiation of Capillary Endothelial Cells: $2.0 \times 10^4$ cells were seeded per well in 24-well clusters in 1 ml complete EMEM containing 10% (v/v) serum and allowed to grow for 72 hours. Media were removed and the cells were washed twice with phosphate-buffer saline, pH 7.4 (PBS). Cells were synchronized by incubating for 48 hours in 2 mM hydroxyurea in serum-free EMEM with glutamine (2 mM) and one-third of penicillin-streptomycin used in a regular culture condition, followed by incubating 24 hours in serum-free EMEM, as discussed in CAO et al., "Modified Method of Mammalian Cell Synchronization Improves Yield and Degree of Synchronization", *Exp. Cell Res.*, 193:405-410 (1991), the disclosure of which is herein incorporated by reference in its entirety. Cells were routinely monitored by light microscopy. For proliferation assay, cells were trypsinized and counted in a hemacytometer. Viability of cells was determined by trypan blue (0.4% (v/v)) exclusion. Statistical analysis was carried out by StatView II software (Macintosh). Quantitation of cellular differentiation was carried out by observing under a Nikon AlphaShot inverted microscope, and counting the number of capillary lumen-like structures in five randomly selected fields per sample. The results were expressed as percent of its corresponding control after normalization of cell numbers. Analysis of Cell Cycle by Flow Cytometry: Assessment of the cell cycle was determined by propidium iodide staining of fixed cell nuclei followed by flow cytometry in a FacSort (Beckton Dickinson) according to the method of Krishan (1975) as modified by Vindelov (1977), as discussed in KRISHAN, "Rapid Flow Cytometric Analysis of Mammalian Cell Cycle by Propidium Iodide Staining", *J. Cell Biol.* 66:188-195 (1975); and VINDELOV, "Flow Cytometric Analysis of Nuclear DNA in Cells from Solid Tumors and Cell Suspensions", *Virchows Arch (B)*, 24:227-231 (1977), the disclosures of which are herein incorporated by reference in their entireties. Briefly, cells were trypsinized, and pelleted by centrifugation at 900 rpm in a bench top centrifuge (Sorvall T6000B). After washing twice with PBS the cell pellet was resuspended in propidium iodide-buffer (PI-buffer; 10 mM Tris-HCl, pH 8.0 containing 10 mM NaCl, 0.7 µM PI, 700 units/liter RNase, and 0.1% (v/v) NP-40), kept in ice for 30 minutes and then fixed with 2% (v/v) paraformaldehyde. After FacSort calibration, 3000 events were counted per sample. Acquisition and analysis of data were carried out by using Cell Quest flow cytometry software (Macintosh-based). Gates: M1 G0/G1, M2=S, M3=G2+M, M4=apoptosis.

Scanning Electron Microscopy of Capillary Endothelial Cells: $5 \times 10^3$ cells were cultured on 13 mm round Thermanox coverslips in 12 well clusters (COSTAR) in complete EMEM. Cells were synchronized as mentioned above and cultured in EMEM containing either 2% (v/v) FBS (control), 10% (v/v) FBS or 2% (v/v) FBS plus 1 µg/ml tunicamycin. The coverslips were removed at specified times and the cells were fixed in 2.5% (v/v) glutaraldehyde for 30 minutes. The cells were washed three times (10 minutes each) with Millonig (1961) isotonic phosphate buffer, pH 7.3 , and treated with 1% (w/v) osmium tetroxide for 15 minutes. See MILLONIG, "Advantages of a Phosphate Buffer for Osmium Tetroxide Solutions in Fixation", *J. Appl. Physics,* 32:1637 (1961), the disclosure of which is herein incorporated by reference in its entirety. After washing with isotonic phosphate buffer, pH 7.3 with three changes, the specimens were dehydrated with 30%, 60% and 90% (10 minutes each), and finally with 100% (v/v) acetone in three changes. In the final step, the specimens were treated with 1:1 mixture of 100% (v/v) acetone and Peidry II for 1 hour and then changed to 100% (v/v) Peldry II for 30 minutes. The specimens were cooled below 23° C. (18° to 20° C.), placed under low vacuum (over night), mounted on a sample mount, coated with metal in E5200 Auto Sputter (gold film thickness 200 nm) and examined in Autoscan ETEC Scanning Electron Microscope.

Monitoring the Expression of Factor VIII:C: (a) By in situ labeling with radioisotope: The cells were seeded in 100 mm culture dish. After every 24 hours, cells were washed with methionine-free/serum-free media and labeled with [$^{35}$S] methionine (40 µCi/ml; Sp. Act.>1,000 Ci/mmol) in the same media containing 1 µg/ml aprotinin at 37° C. for one hour. The medium was removed and the cells lysed for 20 minutes by incubating with 1 ml of ice-cold 20 mM Tris-HCl, pH 8.0 buffer containing 150 mM NaCl, 1% (v/v) NP-40 and 1 µg/ml aprotinin. Cell lysates were clarified by centrifugation at 100,000×g for 30 minutes. Equal aliquots of conditioned media and cell extracts were immunoprecipitated with IgG1k, the above-noted mouse monoclonal antibody to FVIII:C, (1:40 dilution) for 3 hours at 4° C., followed by 12 hours with 50 µg/ml of Protein A-Sepharose CL-4B (30 mg/ml) in the presence of PMSF (1 mM), TPCK (200 µM), soybean trypsin inhibitor (1 µg/ml) and leupeptin (1 µM). The Protein A-Sepharose:antigen-antibody complexes were washed twice with NET buffer (50 mM Tris-HCl, pH 7.4 containing 150 mM NaCl, 5 mM EDTA, β-mercaptoethanol, 0.02% (w/v) NaN$_3$, and 0.2% (w/v) BSA). This was followed by washing twice with the washing buffer (100 mM Tris-HCl, pH 7.5 containing 50 mM LiCl, and 1% (v/v) β-mercaptoethanol), and once with PBS, pH 7.4, as described earlier (BANERJEE et al. (1992), cited above). The immune complexes were separated on 10% (w/v) SDS-PAGE. Factor VIII:C protein bands were detected by autoradiography, and quantitated in a BioRad Imaging Densitometer, Model GS-670 using Molecular Analyst software (Macintosh-based).

(b) By enzyme-linked immuno assay: 96-well microtiter EIA plates, available from Corning Inc., Corning, N.Y., were coated overnight at 4° C. with 50 µl mouse monoclonal anti-Factor VIII:C antibody (i.e., IgG1k which is commercially available from Molecular Biochemicals (previously known as "Boehringer-Mannheim"), Indianapolis, Ind. (diluted 1:500) in 100 mM sodium carbonate buffer, pH 9.2. Blank wells were coated similarly with 0.25 µg of bovine serum albumin (BSA). The plates were washed three times 50 µl each wash with 50 mM Tris-HCl, pH 7.5 containing 150 mM NaCl and 0.5% (v/v) Tween-20 (TBST), available from Bio-Rad Laboratories, Richmond, Calif. and incubated at 37° C. for one hour with 50 µl conditioned media or cell lysates. The cell lysates were obtained by incubating for 20 minutes with 1 ml of ice-cold 20 mM TRIS-HCL, pH 8.0 buffer containing 150 mM NaCl, 1% (v/v) NP-40 and 1 µg/ml aprotinin. At the end of the incubation, the plates were washed three times with TBST, as above, and incubated at 37° C. for another hour with 50 µl of 1:500 diluted monoclonal anti-Factor VIII:C antibody. The plates were washed three times with TBST and incubated for one hour with alkaline phosphatase-conjugated goat anti-mouse IgG, available from Molecular Biochemicals, Indianapolis, Ind., (diluted 1:2,000 in 50 mM Tris-HCl, pH 7.5). After washing the plates three times with TBST, the plates were incubated with 50 µl of phosphatase substrate cocktail (50 mM p-nitrophenyl phosphate in 500 mM glycine-NaOH buffer, pH 10.0 containing 100 mM MgC$_2$ and 100 mM ZnCl$_2$). The absorbance was read at approximately 405 nm after 30 minutes by using an EIA microplate reader, Model 2550 with a 405 nm filter, both available from Bio-Rad Laboratories, Richmond, Calif.

Results

Serum and bFGF/FGF-2 Stimulated Growth and Proliferation of Capillary Endothelial Cells: Synchronized cells were cultured in complete EMEM containing either 1% (v/v), 2% (v/v), or 10% (v/v) fetal bovine serum and monitored for 5 days. For light microscopy, cell number determination, and flow cytometry, cells were sampled at eight-hour intervals. Results in FIG. 6 showed that cells maintained a status quo for first 32 hours after synchronization. Cells proliferated normally in media containing either 2% (v/v) or 10% (v/v) fetal bovine serum, but maximum cellular growth was observed at 10% (v/v) serum. At 1% (v/v) serum, cells survived but did not proliferate (FIG. 6A). All cultures containing 2% (v/v) fetal bovine serum were referred to as controls in this study. bFGF/FGF-2 at 10 ng/ml to 100 ng/ml similarly stimulated the endothelial cell proliferation over the controls (FIG. 6B). It is also to noted that at stimulatory concentrations bFGF/FGF-2 reduced the lag phase by almost 24 hours.

Figure 8:
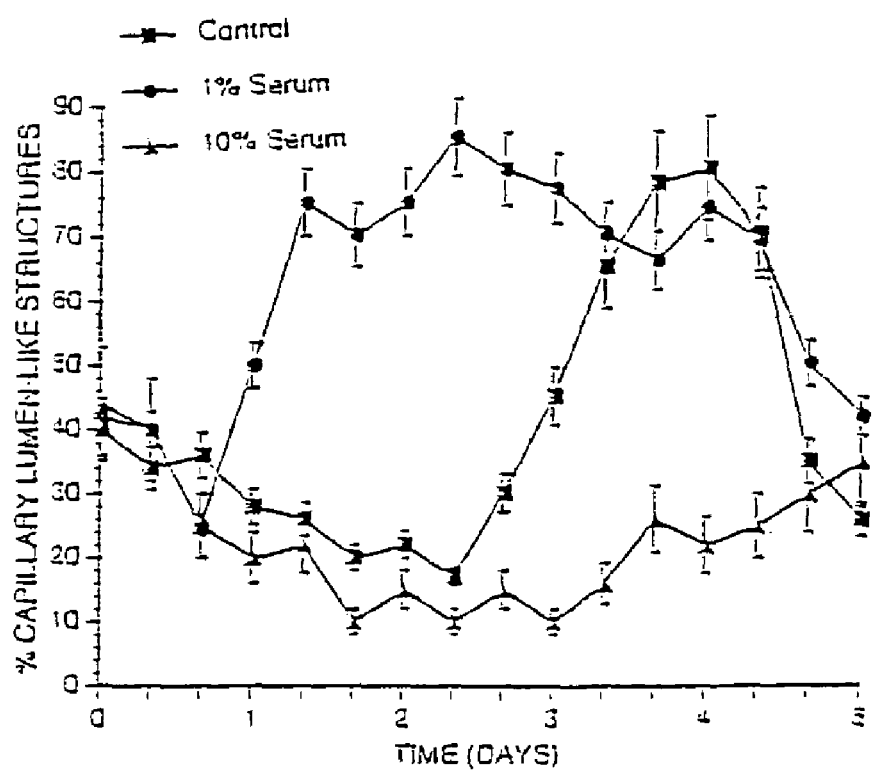
FIG. 8 shows quantitative analysis of capillary endothelial cell differentiation in vitro. Synchronized cells were cultured in 1% (v/v), 2% (v/v), or 10% (v/v) heat-inactivated fetal bovine serum containing EMEM for 5 days. Cells were examined under a light microscope and scored for lumen-like structure formation at eight-hour intervals. Results were normalized for cell numbers. Each point represents the mean±SEM from five randomly selected fields(n=15). (●) 1% (v/v) heat-inactivated fetal bovine serum, (■) 2% (v/v) heat-inactivated fetal bovine serum, and (▲) 10% (v/v) heat-inactivated fetal bovine serum.

Light microscopic examination of cells immediately after terminating the synchronization process as well as after culturing in media containing different concentrations of serum, exhibited distinct morphology (FIG. 7). When cultured in 2% (v/v) serum, cells proliferated and also attended a same degree of differentiation (FIG. 7B) as observed at time 'zero' (i.e., immediately after synchronization; FIG. 7A). Under this culture condition complete differentiation was observed only after 5 days (FIG. 7C). When the synchronized cultures were stimulated with 10% (v/v) serum, a morphology different from those at 2% (v/v) serum was observed. Cells proliferated for the first 72 hours, reaching a confluency in 5 days (FIGS. 8D and 8E). Cells, however, began to differentiate around day 10 (FIG. 7F). Quantitative analysis of the cellular differentiation is summarized in FIG. 8. The behavior of the capillary endothelial cells cultured in the presence of bFGF/FGF-2 appeared similar to those cultured in 10% (v/v) serum (data not shown).

Figure 10A:
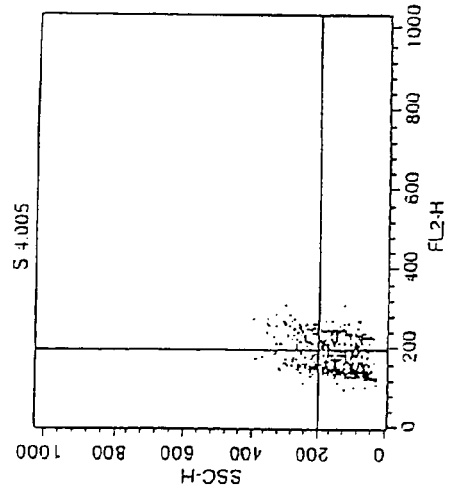
FIGS. 10A-10D shows analysis of cell cycle by flow cytometry. Synchronized cultures of capillary endothelial cells were grown in 2% (v/v) heat-inactivated fetal bovine serum containing EMEM. At different time intervals, cells were removed, processed and their DNA content was measured by flow cytometry after propidium iodide staining. Each histogram represents the distribution of 3,000 cells. Cell cycle gates: M1=G0/G1 phase, M2=S phase, M3=G2+M phase, M4=apoptosis.
Figure 10B:
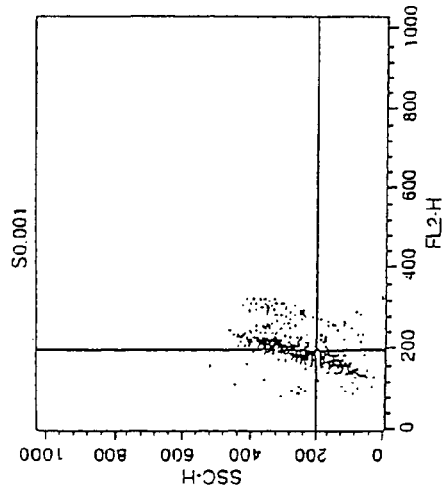
Figure 10:
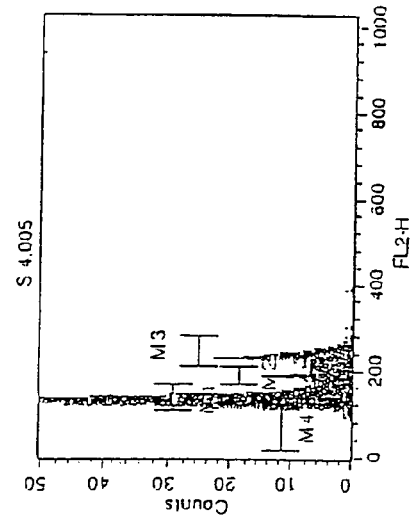

To examine the surface characteristics of these capillary endothelial cells, synchronized cultures in Thermanox coverslips were placed in 2% (v/v) or 10% (v/v) serum containing EMEM. At specified times, the cells were fixed and processed for scanning electron microscopy. The results from such experiments indicated that cells cultured for 96 hours in 2% (v/v) serum exhibited a distinct surface morphology with no blebbing. Cells cultured in 10% (v/v) serum grew substantially larger in size than those cultured in 2% (v/v) serum for the same period of time (FIGS. 10A and 10B). A dramatic shift in morphology towards a capillary tube was observed after seven days in culture in medium containing 2% (v/v) serum (FIG. 9C).

Capillary Endothelial Cell Progression through the Cell Cycle: Synchronized cultures of capillary endothelial cells were examined at eight-hour intervals by flow cytometry after culturing in media containing 2% (v/v), or 10% (v/v) serum. In each case 3,000 events of propidium iodide-stained nuclei were analyzed. The synchronization protocol established in this study arrested ~90% of the cell population in the G0/G1 phase (FIG. 10A). Progression through the cell cycle was analyzed by evaluating the distribution of cells in the G0/G1 phase, S-phase and in the G2+M phase. Results from experiments carried out with cells in 32 hours, 40 hours, and 48 hours in culture are summarized in FIGS. 11B-11D. At 24 hours, the distribution of cells in G0/G1 phase, S-phase, and in the G2+M phase appeared to be the same. However, after monitoring the cells for 5 days, it was concluded that these capillary endothelial cells needed approximately 68 hours to complete one cycle (i.e., doubling the cell population). Further analysis indicated that during progression through the cell cycle, the cell population spent nearly 36 hours in the GI phase, 8 hours in the S phase, and 24 hours in the G2+M phase when cultured in 2% (v/v) serum. Cells cultured in 10% (v/v) serum, however, shortened the cell cycle by 12 hours of which the G1 phase was shortened at least by 8 hours (FIGS. 12A and 12B). Cell doubling time in the presence of bFGF/FGF-2 was similar to that of 10% (v/v) serum (data not shown).

Expression of Factor VIII:C During Capillary Endothelial Cell Proliferation: Expression of a $M_r$270,000 dalton asparagine-linked (N-linked) glycoprotein with a biological function of Factor VIII:C of the blood coagulation-cascade had been detected in these capillary endothelial cells, as discussed in BANERJEE et al., "Microvascular Endothelial Cells from Adrenal Medulla—A Model for in vitro Angiogenesis", *Angiogenesis: Models, Modulators, and Clinical Applications*, pp. 7-18 (1998); and BANERJEE et al., "Expression of Blood Clotting Factor VIII:C Gene in Capillary Endothelial Cells", *FEBS Letts.* 306:33-37 (1992), the disclosures of which are herein incorporated by reference in their entireties. To examine a direct link between the cellular proliferation and the expression of Factor VIII:C, cells were harvested after every 24 hours, washed and labeled with [$^{35}$S]methionine for one hour in a methionine-free/serum-free medium. An aliquot from these cell suspensions was counted and the rest were lysed. Factor VIII:C from equal amount of cell lysates was immunoprecipitated, separated on a 10% (w/v) SDS-PAGE, autoradiographed and analyzed in a Scanning Densitometer. The results indicated a temporal relationship between the cell proliferation and the Factor VIII:C expression (FIG. 12). Furthermore, it was also observed that the expression of Factor VIII:C preceded the cellular proliferation by 24 hours.

Effect of Tunicamycin on Capillary Endothelial Cell Proliferation: Tunicamycin inhibits protein glycosylation by blocking the activity of N-acetylglucosaminyl-1-phosphate transferase activity and consequently the assembly of Glc$_3$Man$_9$GlcNAc$_2$-PP-Dol (OSL), which assembly is discussed in ELBEIN, "Inhibitors of the Biosynthesis and Processing of N-linked Oligosaccharide Chain", *Annu. Rev. Biochem.* 56:497-534 (1987), the disclosure of which is herein incorporated by reference in its entirety. To address whether OSL plays any significant role during capillary endothelial cell growth and proliferation, the synchronized cultures were placed in EMEM containing either 2% (v/v) serum (i.e., control), or 2% (v/v) serum plus 1 μg/ml of tunicamycin and monitored for 5 days. Cells were removed at eight-hour intervals and processed for total cell counts, morphological characterization, and flow cytometry. The results in FIG. 13A indicated that the cell growth rate in the controls and in the presence of tunicamycin were indistinguishable during the first 48 hours. After that time point, the cell population in tunicamycin-treated culture started declining, and almost disappeared. Morphology by light microscopy indicated cell shrinkage, loss of membrane contact with neighboring cells, apparent compaction of nuclei showing condensed pyknotic appearance, and membrane fragmentation (FIG. 13B). All these features are characteristics of apoptosis, as discussed in GRANVILLE et al., "Apoptosis: Molecular Aspects of Cell Death and Disease", *Lab. Invest.*, 78:893-913 (1998), the disclosure of which is herein incorporated by reference in its entirety. Scanning electron microscopy exhibited enormous surface blebbing after culturing in the presence of tunicamycin (1 μg/ml) for 96 hours (FIG. 13C).

Flow cytometric analysis revealed that 70% of the cell population went into apoptosis after 32 hours treatment with 1 μg/ml of tunicamycin (FIG. 13D). This strongly suggested that synthesis of Glc$_3$Man$_9$GlcNAc$_2$-PP-Dol is intricately connected with endothelial cell proliferation.

Figure 14:
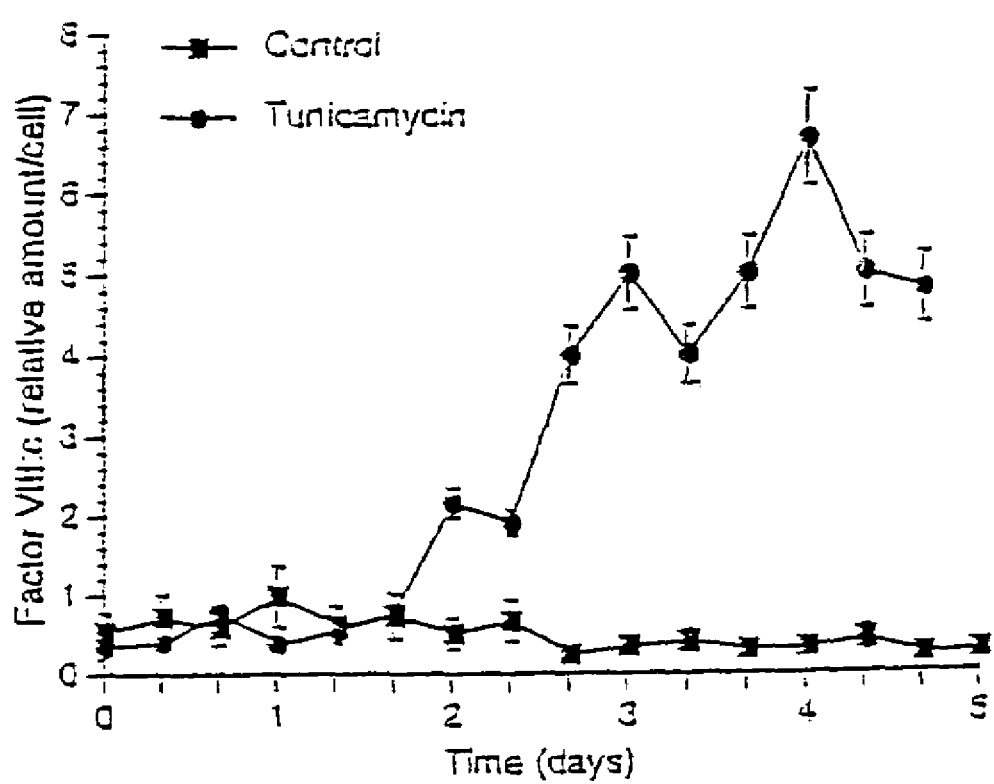
FIG. 14 shows the concentration of Factor VIII:C in cells cultured in the presence or absence of tunicamycin. Synchronized cells were cultured in 2% (v/v) heat-inactivated fetal bovine serum containing EMEM in the absence (control) or presence of 1 μg/ml of tunicamycin. At different times cultures were withdrawn and Factor VIII:C was quantitated by enzyme-linked immunoassay (ELISA) in the conditioned media as well as in the cell lysate. The results were normalized for cell numbers. Each point represents the mean±SEM (n=6), where (■) control; (●) tunicamycin treated (1 μg/ml).

If the cellular proliferation is mediated by the N-glycosylation event, then it is expected that during tunicamycin inhibition of the actively proliferating culture, the level of unglycosylated glycoprotein would increase. To address this issue, the expression of the capillary endothelial cell marker glycoprotein Factor VIII:C was observed in both conditioned media and in the cell lysates by enzyme-linked immunoassay (ELISA). The results in FIG. 14 indicated a high level of anti-Factor VIII:C immunopositive material in tunicamycin-treated cells over the controls.

While the invention has been described in connection with certain preferred embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

What is claimed is:

1. A method for inhibiting angiogenesis, comprising:
administering a nucleoside in an amount effective to inhibit angiogenesis, to a patient in need of such treatment, the nucleoside comprising glucosamine, and wherein the glucosamine comprises at least one tunicamycin and functional derivatives thereof, and wherein the at least one of tunicamycin and functional derivatives thereof is administered for a period of time, subsequently the administration of the at least one of tuniumycin and functional derivatives thereof is suspended for a period of time of at least about 1 week, and subsequently the administration of the at least one of tunicamycin and functional derivatives thereof is resumed.

2. A method for inhibiting angiogenesis, comprising:
administering a nucleoside in an amount effective to inhibit angiogenesis, to a patient in need of such treatment, the nucleoside comprising glucosamine, wherein the glucosamine comprises at least one of tunicamycin and functional derivatives thereof, and wherein the glucosamine is administered for a period of about 1 week to 6 months at a daily dosage of about 5 to 20 mg/kg of body weight, subsequently the administration of the glucosamine is suspended for a period of about 1 week to 6 months, and subsequently the glucosamine is administered for a period of about 1 week to 6 months at a daily dose of about 5 to 20 mg/kg of body weight.

3. A method for inhibiting angiogenesis, comprising:
administering tunicamycin in an amount effective to inhibit angiogenesis, to a patient in need of such treatment;
wherein the tunicamycin is administered for a period of about 1 week to 6 months at a daily dosage of about 5 to 20 mg/kg of body weight, subsequently the administration of the tunicamycin is suspended for a period of about 1 week to 6 months, and subsequently the tunicamycin is administered for a period of about 1 week to 6 months at a daily dosage of about 5 to 20 mg/kg of body weight.

* * * * *